(12) United States Patent
Ramaen et al.

(10) Patent No.: US 12,275,976 B2
(45) Date of Patent: Apr. 15, 2025

US012275976B2

(54) PHLOROGLUCINOL-RESISTANT CELL, IN PARTICULAR YEAST

(71) Applicant: COMPAGNIE GENERALE DES ETABLISSEMENTS MICHELIN, Clermont-Ferrand (FR)

(72) Inventors: Odile Ramaen, Ablis (FR); Vincent Lafaquiere, Clermont-Ferrand (FR); Dominique Louis, Forges les Bains (FR)

(73) Assignee: COMPAGNIE GENERALE DES ETABLISSEMENTS MICHELIN, Clermont-Ferrand (FR)

( * ) Notice: Subject to any disclaimer, the term of this patent is extended or adjusted under 35 U.S.C. 154(b) by 836 days.

(21) Appl. No.: 17/428,827

(22) PCT Filed: Feb. 5, 2020

(86) PCT No.: PCT/FR2020/050189
§ 371 (c)(1),
(2) Date: Aug. 5, 2021

(87) PCT Pub. No.: WO2020/161436
PCT Pub. Date: Aug. 13, 2020

(65) Prior Publication Data
US 2022/0098626 A1 Mar. 31, 2022

(30) Foreign Application Priority Data
Feb. 5, 2019 (FR) ...................................... 1901115

(51) Int. Cl.
*C12N 9/10* (2006.01)
*C12N 15/52* (2006.01)
*C12P 7/22* (2006.01)

(52) U.S. Cl.
CPC .............. *C12P 7/22* (2013.01); *C12N 9/1029* (2013.01); *C12N 15/52* (2013.01)

(58) Field of Classification Search
CPC ...................................................... C12N 9/10
See application file for complete search history.

(56) References Cited

U.S. PATENT DOCUMENTS

| 2007/0178571 | A1 | 2/2007 | Frost |
| 2011/0183391 | A1 | 7/2011 | Frost |
| 2020/0123508 | A1 | 4/2020 | Lafaquiere et al. |
| 2021/0147884 | A1 | 5/2021 | Lafaquiere et al. |

FOREIGN PATENT DOCUMENTS

| CN | 101084311 A | 12/2007 |
| CN | 101724662 A | 6/2010 |
| CN | 102787135 A | 11/2012 |
| WO | 2006/044290 A2 | 4/2006 |
| WO | 2012/006244 A1 | 1/2012 |
| WO | 2018/211032 A1 | 11/2018 |
| WO | 2019/002798 A1 | 1/2019 |
| WO | 2019/002799 A1 | 1/2019 |

OTHER PUBLICATIONS

International Search Report dated Jun. 4, 2020, in corresponding PCT/FR2020/050189 (8 pages).
Y. Cao, et al., "Improved phloroglucinol production by metabolically engineered *Escherichia coli*", Appl. Microbiol. Biotechnol. vol. 91, No. 6, pp. 1545-1552 (2011).
A. Decottignies, et al., "Complete inventory of the yeast ABC proteins", Nat. Genet., vol. 15, pp. 137-145 (1997).
G. Del Sorbo, et al., "Fungal Transporters Involved in Efflux of Natural Toxic Compounds and Fungicides", Fungal Genet. Biol., vol. 30, pp. 1-15 (2000).
C. Schuller, et al., "Inventory and Evolution of Fungal ABC Protein Genes", ABC Proteins: From Bacteria to Man, Elsevier Science Ltd., chapter 14, pp. 279-293 (2003).
E. Balzi, et al., "Yeast Multidrug Resistance: The PDR Network", J. Bioenerg. Biomembranes, vol. 27, pp. 71-76 (1995).
M. Kolaczkowski, et al., "In Vivo Characterization of the Drug Resistance Profile of the Major ABC Transporters and Other Components of the Yeast Pleiotropic Drug Resistance Network", Microb. Drug Resist., vol. 4, No. 3, pp. 143-158 (1998).
Y. Mahé, et al., "The ATP Binding Cassette Transporters Pdr5 and Snq2 of *Saccharomyces cerevisiae* Can Mediate Transport of Steroids in Vivo", J. Biol. Chem., vol. 271, No. 41, pp. 25167-25172 (1996).
H. Wolfger, et al., "The Yeast Pdr15p ATP-binding Cassette (ABC) Protein Is a General Stress Response Factor Implicated in Cellular Detoxification", J. Biol. Chem., vol. 279, No. 12, pp. 11593-11599 (2004).
P. Piper, et al., "The Pdr12 ABC transporter is required for the development of weak organic acid resistance in yeast", EMBO J., vol. 17, No. 15, pp. 4257-4265 (1998).
M. D. Marger, et al., "A major superfamily of transmembrane facilitators that catalyse uniport, symport and antiport", Trends Biochem. Sci., vol. 18, pp. 13-20 (1993).
L. R. Forrest, et al., "The structural basis of secondary active transport mechanisms", Biochim. Biophys. Acta, vol. 1807, pp. 167-188 (2011).
N. Yan, "Structural advances for the major facilitator superfamily (MFS) transporters", Trends Biochem. Sci., vol. 38, No 3, p. 151-159 (2013).
J. Achkar, et al., "Biosynthesis of Phloroglucinol", J. Am. Chem. Soc., vol. 127, pp. 5332-5333 (2005).
W. Zha, et al., "Characterization of the Substrate Specificity of PHLD, a Type III Polyketide Synthase from Pseudomonas fluorescens", J. Biol. Chem., vol. 281, pp. 32036-32047 (2006).
L. Meslet-Cladière, et al., "Structure/Function Analysis of a Type III Polyketide Synthase in the Brown Alga Ectocarpus siliculosus Reveals a Biochemical Pathway in Phlorotannin Monomer Biosynthesis", Plant Cell, vol. 25, pp. 3089-3103 (2013).

(Continued)

*Primary Examiner* — Tekchand Saidha
(74) *Attorney, Agent, or Firm* — VENABLE LLP

(57) ABSTRACT

The present invention relates to a living cell, preferably a host cell, that is phloroglucinol resistant. The present invention also relates to a method for producing a phloroglucinol-resistant recombinant host cell. The present invention also relates to a method for producing phloroglucinol.

17 Claims, 6 Drawing Sheets

Figure 1:
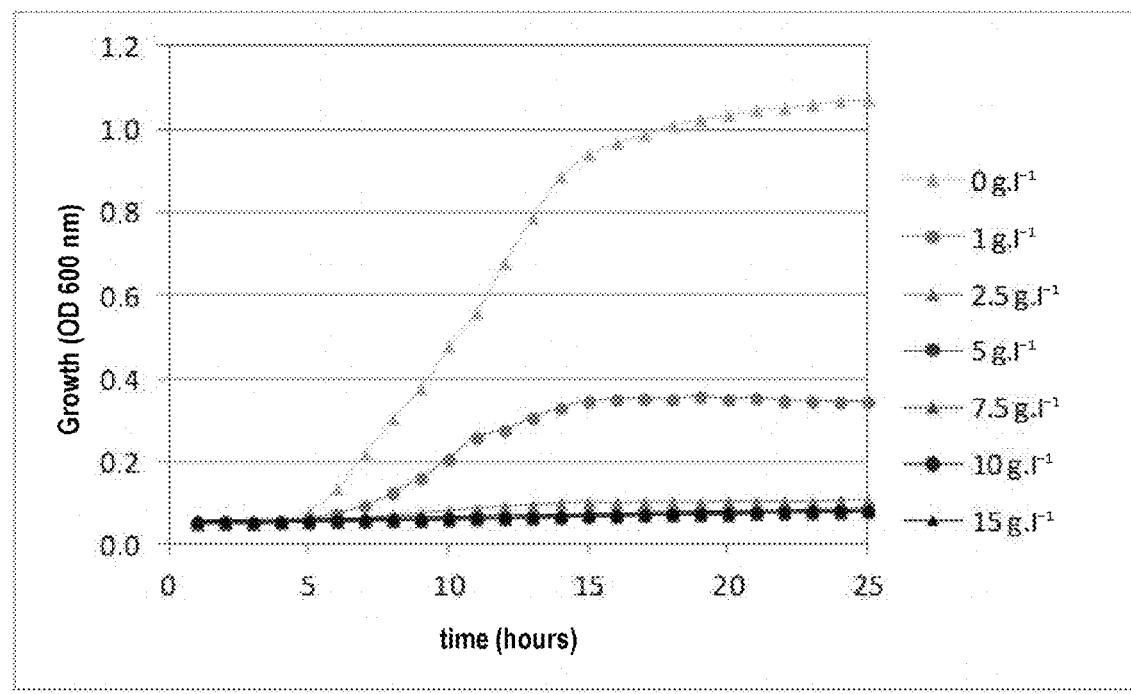

Specification includes a Sequence Listing.

(56) References Cited

OTHER PUBLICATIONS

F. Yang, et al., "Biosynthesis of phloroglucinol compounds in microorganisms—review", Appl. Microbiol Biotech, vol. 93, pp. 487-495 (2012).
S. E. Abdel-Ghany, et al., "Production of Phloroglucinol, a Platform Chemical, in *Arabidopsis* using a Bacterial Gene", Sci. Reports, vol. 6, No. 1, pp. 1-14 (2016).
K. Y. Hara, et al., "Transporter engineering in biomass utilization by yeast", FEMS Yeast Res., vol. 17, No. 7, pp. 1-14 (2017).
C. P. Godinha, et al., "The Paralogous Genes PDR 18 and SNQ2, Encoding Multidrug Resistance ABC Transporters, Derive From a Recent Duplication Event, PDR18 Being Specific to the *Saccharomyces* Genus", Frontiers in Genetics, vol. 9, pp. 1-17 (2018).
M. Dayhoff, ed., "Atlas of Protein Sequence and Structure", National Biomedical Research Foundation, vol. 5, supp. 3, Table of Contents (1978).
M. Dayhoff, ed., "Atlas of Protein Sequence and Structure", National Biomedical Research Foundation, vol. 5, supp. 3, chapter 1 (1978).
M. Dayhoff, ed., "Atlas of Protein Sequence and Structure", National Biomedical Research Foundation, vol. 5, supp. 3, chapter 23 (1978).
R. Zhang, et al., "Improving phloroglucinol tolerance and production in *Escherichia coli* by GroESL overexpression", Microb Cell Fact (2017) 16:227.

| pJLP1 | loxP1 | HIS5.Sp-loxP | loxP2 | pCCW12 | PDR | tRPL15A | uLP1 |

Fig. 4A

| gene expressed | Name of the strain obtained | |
|---|---|---|
| PDR1 | YA2784-1 | YA2784-3 |
| PDR3 | YA2785-1 | YA2785-2 |
| PDR5 | YA2791-3 | YA2791-5 |
| SNQ2 | YA2786-1 | YA2786-2 |
| PDR10 | YA2792-3 | YA2792-5 |
| PDR11 | YA2814-1 | YA2814-2 |
| PDR15 | YA2793-1 | YA2793-4 |
| PDR18 | YA3277-2 | YA3277-3 |
| ADP1 | YA3086-1 | YA3086-2 |
| AUS1 | YA3087-1 | YA3087-2 |
| STE6 | YA3085-1 | YA3085-3 |
| YOL075C | YA3274-1 | YA3274-2 |
| YOR1 | YA3275-2 | YA3275-3 |
| PDR12 | YA3276-5 | YA3276-6 |

Fig. 4B

| pJLP1 | loxP1 | HIS5.Sp-loxP | loxP2 | pCCW12 | MFS gene | tRPL15A | tJLP1 |

Fig. 6A

| gene expressed | Name of the strain obtained | |
|---|---|---|
| AQR1 | YA3014-3 | YA3014-4 |
| DTR1 | YA3015-1 | YA3015-2 |
| FLR1 | YA3051-1 | YA3051-2 |
| HOL1 | YA3052-1 | YA3052-6 |
| QDR1 | YA3016-1 | YA3016-2 |
| QDR2 | YA3017-1 | YA3017-2 |
| QDR3 | YA3018-1 | YA3018-2 |
| TPO1 | YA3019-1 | YA3019-2 |
| TPO2 | YA3020-1 | YA3020-2 |
| TPO3 | YA3053-1 | YA3053-6 |
| TPO4 | YA3021-1 | YA3021-2 |
| YHK8 | YA3022-1 | YA3022-3 |
| ATR1 | YA3054-2 | YA3054-6 |
| AZR1 | YA3055-1 | YA3055-2 |
| SGE1 | YA3056-1 | YA3056-2 |
| SIT1 | YA3057-1 | YA3057-2 |
| ENB1 | YA30578-1 | YA3058-2 |
| GEX1 | YA3059-1 | YA3059-3 |
| GEX2 | YA3060-1 | YA3060-2 |

Fig. 6B

SEQUENCE LISTING

<160> NUMBER OF SEQ ID NOS: 35

<210> SEQ ID NO 1
<211> LENGTH: 1511
<212> TYPE: PRT
<213> ORGANISM: Saccharomyces cerevisiae

<400> SEQUENCE: 1

Met Pro Glu Ala Lys Leu Asn Asn Asn Val Asn Asp Val Thr Ser Tyr

```
  1               5                   10                  15
Ser Ser Ala Ser Ser Thr Glu Asn Ala Ala Asp Leu His Asn Tyr
            20                  25                  30
Asn Gly Phe Asp Glu His Thr Glu Ala Arg Ile Gln Lys Leu Ala Arg
            35                  40                  45
Thr Leu Thr Ala Gln Ser Met Gln Asn Ser Thr Gln Ser Ala Pro Asn
        50                  55                  60
Lys Ser Asp Ala Gln Ser Ile Phe Ser Ser Gly Val Glu Gly Val Asn
65                  70                  75                  80
Pro Ile Phe Ser Asp Pro Glu Ala Pro Gly Tyr Asp Pro Lys Leu Asp
                85                  90                  95
Pro Asn Ser Glu Asn Phe Ser Ala Ala Trp Val Lys Asn Met Ala
                100                 105                 110
His Leu Ser Ala Ala Asp Pro Asp Phe Tyr Lys Pro Tyr Ser Leu Gly
                115                 120                 125
Cys Ala Trp Lys Asn Leu Ser Ala Ser Gly Ala Ser Ala Asp Val Ala
            130                 135                 140
Tyr Gln Ser Thr Val Val Asn Ile Pro Tyr Lys Ile Leu Lys Ser Gly
145                 150                 155                 160
Leu Arg Lys Phe Gln Arg Ser Lys Glu Thr Asn Thr Phe Gln Ile Leu
                165                 170                 175
Lys Pro Met Asp Gly Cys Leu Asn Pro Gly Glu Leu Val Val Leu
            180                 185                 190
Gly Arg Pro Gly Ser Gly Cys Thr Thr Leu Leu Lys Ser Ile Ser Ser
                195                 200                 205
Asn Thr His Gly Phe Asp Leu Gly Ala Asp Thr Lys Ile Ser Tyr Ser
    210                 215                 220
Gly Tyr Ser Gly Asp Asp Ile Lys Lys His Phe Arg Gly Glu Val Val
225                 230                 235                 240
Tyr Asn Ala Glu Ala Asp Val His Leu Pro His Leu Thr Val Phe Glu
                245                 250                 255
Thr Leu Val Thr Val Ala Arg Leu Lys Thr Pro Gln Asn Arg Ile Lys
            260                 265                 270
Gly Val Asp Arg Glu Ser Tyr Ala Asn His Leu Ala Glu Val Ala Met
            275                 280                 285
Ala Thr Tyr Gly Leu Ser His Thr Arg Asn Thr Lys Val Gly Asn Asp
        290                 295                 300
Ile Val Arg Gly Val Ser Gly Gly Glu Arg Lys Arg Val Ser Ile Ala
305                 310                 315                 320
Glu Val Ser Ile Cys Gly Ser Lys Phe Gln Cys Trp Asp Asn Ala Thr
                325                 330                 335
Arg Gly Leu Asp Ser Ala Thr Ala Leu Glu Phe Ile Arg Ala Leu Lys
            340                 345                 350
Thr Gln Ala Asp Ile Ser Asn Thr Ser Ala Thr Val Ala Ile Tyr Gln
            355                 360                 365
Cys Ser Gln Asp Ala Tyr Asp Leu Phe Asn Lys Val Cys Val Leu Asp
    370                 375                 380
Asp Gly Tyr Gln Ile Tyr Tyr Gly Pro Ala Asp Lys Ala Lys Lys Tyr
385                 390                 395                 400
Phe Glu Asp Met Gly Tyr Val Cys Pro Ser Arg Gln Thr Thr Ala Asp
                405                 410                 415
Phe Leu Thr Ser Val Thr Ser Pro Ser Glu Arg Thr Leu Asn Lys Asp
            420                 425                 430
```

```
Met Leu Lys Lys Gly Ile His Ile Pro Gln Thr Pro Lys Glu Met Asn
            435                 440                 445

Asp Tyr Trp Val Lys Ser Pro Asn Tyr Lys Glu Leu Met Lys Glu Val
        450                 455                 460

Asp Gln Arg Leu Leu Asn Asp Asp Glu Ala Ser Arg Glu Ala Ile Lys
465                 470                 475                 480

Glu Ala His Ile Ala Lys Gln Ser Lys Arg Ala Arg Pro Ser Ser Pro
                485                 490                 495

Tyr Thr Val Ser Tyr Met Met Gln Val Lys Tyr Leu Leu Ile Arg Asn
                500                 505                 510

Met Trp Arg Leu Arg Asn Asn Ile Gly Phe Thr Leu Phe Met Ile Leu
            515                 520                 525

Gly Asn Cys Ser Met Ala Leu Ile Leu Gly Ser Met Phe Phe Lys Ile
            530                 535                 540

Met Lys Lys Gly Asp Thr Ser Thr Phe Tyr Phe Arg Gly Ser Ala Met
545                 550                 555                 560

Phe Phe Ala Ile Leu Phe Asn Ala Phe Ser Ser Leu Leu Glu Ile Phe
                565                 570                 575

Ser Leu Tyr Glu Ala Arg Pro Ile Thr Glu Lys His Arg Thr Tyr Ser
            580                 585                 590

Leu Tyr His Pro Ser Ala Asp Ala Phe Ala Ser Val Leu Ser Glu Ile
            595                 600                 605

Pro Ser Lys Leu Ile Ile Ala Val Cys Phe Asn Ile Ile Phe Tyr Phe
            610                 615                 620

Leu Val Asp Phe Arg Arg Asn Gly Gly Val Phe Phe Phe Tyr Leu Leu
625                 630                 635                 640

Ile Asn Ile Val Ala Val Phe Ser Met Ser His Leu Phe Arg Cys Val
                645                 650                 655

Gly Ser Leu Thr Lys Thr Leu Ser Glu Ala Met Val Pro Ala Ser Met
            660                 665                 670

Leu Leu Leu Ala Leu Ser Met Tyr Thr Gly Phe Ala Ile Pro Lys Lys
            675                 680                 685

Lys Ile Leu Arg Trp Ser Lys Trp Ile Trp Tyr Ile Asn Pro Leu Ala
            690                 695                 700

Tyr Leu Phe Glu Ser Leu Leu Ile Asn Glu Phe His Gly Ile Lys Phe
705                 710                 715                 720

Pro Cys Ala Glu Tyr Val Pro Arg Gly Pro Ala Tyr Ala Asn Ile Ser
                725                 730                 735

Ser Thr Glu Ser Val Cys Thr Val Val Gly Ala Val Pro Gly Gln Asp
            740                 745                 750

Tyr Val Leu Gly Asp Asp Phe Ile Arg Gly Thr Tyr Gln Tyr Tyr His
            755                 760                 765

Lys Asp Lys Trp Arg Gly Phe Gly Ile Gly Met Ala Tyr Val Val Phe
            770                 775                 780

Phe Phe Phe Val Tyr Leu Phe Leu Cys Glu Tyr Asn Glu Gly Ala Lys
785                 790                 795                 800

Gln Lys Gly Glu Ile Leu Val Phe Pro Arg Ser Ile Val Lys Arg Met
                805                 810                 815

Lys Lys Arg Gly Val Leu Thr Glu Lys Asn Ala Asn Asp Pro Glu Asn
            820                 825                 830

Val Gly Glu Arg Ser Asp Leu Ser Ser Asp Arg Lys Met Leu Gln Glu
            835                 840                 845
```

```
Ser Ser Glu Glu Glu Ser Asp Thr Tyr Gly Glu Ile Gly Leu Ser Lys
850                 855                 860

Ser Glu Ala Ile Phe His Trp Arg Asn Leu Cys Tyr Glu Val Gln Ile
865                 870                 875                 880

Lys Ala Glu Thr Arg Arg Ile Leu Asn Asn Val Asp Gly Trp Val Lys
                885                 890                 895

Pro Gly Thr Leu Thr Ala Leu Met Gly Ala Ser Gly Ala Gly Lys Thr
                900                 905                 910

Thr Leu Leu Asp Cys Leu Ala Glu Arg Val Thr Met Gly Val Ile Thr
            915                 920                 925

Gly Asp Ile Leu Val Asn Gly Ile Pro Arg Asp Lys Ser Phe Pro Arg
    930                 935                 940

Ser Ile Gly Tyr Cys Gln Gln Asp Leu His Leu Lys Thr Ala Thr
945                 950                 955                 960

Val Arg Glu Ser Leu Arg Phe Ser Ala Tyr Leu Arg Gln Pro Ala Glu
                965                 970                 975

Val Ser Ile Glu Glu Lys Asn Arg Tyr Val Glu Glu Val Ile Lys Ile
            980                 985                 990

Leu Glu Met Glu Lys Tyr Ala Asp  Ala Val Val Gly Val Ala Gly Glu
        995                 1000                1005

Gly Leu  Asn Val Glu Gln Arg  Lys Arg Leu Thr Ile  Gly Val Glu
    1010                1015                1020

Leu Thr  Ala Lys Pro Lys Leu  Leu Val Phe Leu Asp  Glu Pro Thr
    1025                1030                1035

Ser Gly  Leu Asp Ser Gln Thr  Ala Trp Ser Ile Cys  Gln Leu Met
    1040                1045                1050

Lys Lys  Leu Ala Asn His Gly  Gln Ala Ile Leu Cys  Thr Ile His
    1055                1060                1065

Gln Pro  Ser Ala Ile Leu Met  Gln Glu Phe Asp Arg  Leu Leu Phe
    1070                1075                1080

Met Gln  Arg Gly Gly Lys Thr  Val Tyr Phe Gly Asp  Leu Gly Glu
    1085                1090                1095

Gly Cys  Lys Thr Met Ile Asp  Tyr Phe Glu Ser His  Gly Ala His
    1100                1105                1110

Lys Cys  Pro Ala Asp Ala Asn  Pro Ala Glu Trp Met  Leu Glu Val
    1115                1120                1125

Val Gly  Ala Ala Pro Gly Ser  His Ala Asn Gln Asp  Tyr Tyr Glu
    1130                1135                1140

Val Trp  Arg Asn Ser Glu Glu  Tyr Arg Ala Val Gln  Ser Glu Leu
    1145                1150                1155

Asp Trp  Met Glu Arg Glu Leu  Pro Lys Lys Gly Ser  Ile Thr Ala
    1160                1165                1170

Ala Glu  Asp Lys His Glu Phe  Ser Gln Ser Ile Ile  Tyr Gln Thr
    1175                1180                1185

Lys Leu  Val Ser Ile Arg Leu  Phe Gln Gln Tyr Trp  Arg Ser Pro
    1190                1195                1200

Asp Tyr  Leu Trp Ser Lys Phe  Ile Leu Thr Ile Phe  Asn Gln Leu
    1205                1210                1215

Phe Ile  Gly Phe Thr Phe Phe  Lys Ala Gly Thr Ser  Leu Gln Gly
    1220                1225                1230

Leu Gln  Asn Gln Met Leu Ala  Val Phe Met Phe Thr  Val Ile Phe
    1235                1240                1245

Asn Pro  Ile Leu Gln Gln Tyr  Leu Pro Ser Phe Val  Gln Gln Arg
```

```
            1250                1255                1260
Asp Leu Tyr Glu Ala Arg Glu Arg Pro Ser Arg Thr Phe Ser Trp
    1265                1270                1275

Ile Ser Phe Ile Phe Ala Gln Ile Phe Val Glu Val Pro Trp Asn
    1280                1285                1290

Ile Leu Ala Gly Thr Ile Ala Tyr Phe Ile Tyr Tyr Tyr Pro Ile
    1295                1300                1305

Gly Phe Tyr Ser Asn Ala Ser Ala Ala Gly Gln Leu His Glu Arg
    1310                1315                1320

Gly Ala Leu Phe Trp Leu Phe Ser Cys Ala Phe Tyr Val Tyr Val
    1325                1330                1335

Gly Ser Met Gly Leu Leu Val Ile Ser Phe Asn Gln Val Ala Glu
    1340                1345                1350

Ser Ala Ala Asn Leu Ala Ser Leu Leu Phe Thr Met Ser Leu Ser
    1355                1360                1365

Phe Cys Gly Val Met Thr Thr Pro Ser Ala Met Pro Arg Phe Trp
    1370                1375                1380

Ile Phe Met Tyr Arg Val Ser Pro Leu Thr Tyr Phe Ile Gln Ala
    1385                1390                1395

Leu Leu Ala Val Gly Val Ala Asn Val Asp Val Lys Cys Ala Asp
    1400                1405                1410

Tyr Glu Leu Leu Glu Phe Thr Pro Pro Ser Gly Met Thr Cys Gly
    1415                1420                1425

Gln Tyr Met Glu Pro Tyr Leu Gln Leu Ala Lys Thr Gly Tyr Leu
    1430                1435                1440

Thr Asp Glu Asn Ala Thr Asp Thr Cys Ser Phe Cys Gln Ile Ser
    1445                1450                1455

Thr Thr Asn Asp Tyr Leu Ala Asn Val Asn Ser Phe Tyr Ser Glu
    1460                1465                1470

Arg Trp Arg Asn Tyr Gly Ile Phe Ile Cys Tyr Ile Ala Phe Asn
    1475                1480                1485

Tyr Ile Ala Gly Val Phe Tyr Trp Leu Ala Arg Val Pro Lys
    1490                1495                1500

Lys Asn Gly Lys Leu Ser Lys Lys
    1505                1510

<210> SEQ ID NO 2
<211> LENGTH: 1501
<212> TYPE: PRT
<213> ORGANISM: Saccharomyces cerevisiae

<400> SEQUENCE: 2

Met Ser Asn Ile Lys Ser Thr Gln Asp Ser Ser His Asn Ala Val Ala
1               5                   10                  15

Arg Ser Ser Ser Ala Ser Phe Ala Ala Ser Glu Glu Ser Phe Thr Gly
                20                  25                  30

Ile Thr His Asp Lys Asp Glu Gln Ser Asp Thr Pro Ala Asp Lys Leu
            35                  40                  45

Thr Lys Met Leu Thr Gly Pro Ala Arg Asp Thr Ala Ser Gln Ile Ser
        50                  55                  60

Ala Thr Val Ser Glu Met Ala Pro Asp Val Val Ser Lys Val Glu Ser
65                  70                  75                  80

Phe Ala Asp Ala Leu Ser Arg His Thr Thr Arg Ser Gly Ala Phe Asn
                85                  90                  95
```

```
Met Asp Ser Asp Ser Asp Gly Phe Asp Ala His Ala Ile Phe Glu
             100                 105                 110
Ser Phe Val Arg Asp Ala Asp Glu Gln Gly Ile His Ile Arg Lys Ala
             115                 120                 125
Gly Val Thr Ile Glu Asp Val Ser Ala Lys Gly Val Asp Ala Ser Ala
         130                 135                 140
Leu Glu Gly Ala Thr Phe Gly Asn Ile Leu Cys Leu Pro Leu Thr Ile
145                 150                 155                 160
Phe Lys Gly Ile Lys Ala Lys Arg His Gln Lys Met Arg Gln Ile Ile
                 165                 170                 175
Ser Asn Val Asn Ala Leu Ala Glu Ala Gly Glu Met Ile Leu Val Leu
             180                 185                 190
Gly Arg Pro Gly Ala Gly Cys Ser Ser Phe Leu Lys Val Thr Ala Gly
         195                 200                 205
Glu Ile Asp Gln Phe Ala Gly Gly Val Ser Gly Glu Val Ala Tyr Asp
         210                 215                 220
Gly Ile Pro Gln Glu Glu Met Met Lys Arg Tyr Lys Ala Asp Val Ile
225                 230                 235                 240
Tyr Asn Gly Glu Leu Asp Val His Phe Pro Tyr Leu Thr Val Lys Gln
                 245                 250                 255
Thr Leu Asp Phe Ala Ile Ala Cys Lys Thr Pro Ala Leu Arg Val Asn
             260                 265                 270
Asn Val Ser Lys Lys Glu Tyr Ile Ala Ser Arg Arg Asp Leu Tyr Ala
             275                 280                 285
Thr Ile Phe Gly Leu Arg His Thr Tyr Asn Thr Lys Val Gly Asn Asp
         290                 295                 300
Phe Val Arg Gly Val Ser Gly Gly Glu Arg Lys Arg Val Ser Ile Ala
305                 310                 315                 320
Glu Ala Leu Ala Ala Lys Gly Ser Ile Tyr Cys Trp Asp Asn Ala Thr
                 325                 330                 335
Arg Gly Leu Asp Ala Ser Thr Ala Leu Glu Tyr Ala Lys Ala Ile Arg
             340                 345                 350
Ile Met Thr Asn Leu Leu Lys Ser Thr Ala Phe Val Thr Ile Tyr Gln
             355                 360                 365
Ala Ser Glu Asn Ile Tyr Glu Thr Phe Asp Lys Val Thr Val Leu Tyr
370                 375                 380
Ser Gly Lys Gln Ile Tyr Phe Gly Leu Ile His Glu Ala Lys Pro Tyr
385                 390                 395                 400
Phe Ala Lys Met Gly Tyr Leu Cys Pro Pro Arg Gln Ala Thr Ala Glu
                 405                 410                 415
Phe Leu Thr Ala Leu Thr Asp Pro Asn Gly Phe His Leu Ile Lys Pro
             420                 425                 430
Gly Tyr Glu Asn Lys Val Pro Arg Thr Ala Glu Glu Phe Glu Thr Tyr
         435                 440                 445
Trp Leu Asn Ser Pro Glu Phe Ala Gln Met Lys Lys Asp Ile Ala Ala
             450                 455                 460
Tyr Lys Glu Lys Val Asn Thr Glu Lys Thr Lys Glu Val Tyr Asp Glu
465                 470                 475                 480
Ser Met Ala Gln Glu Lys Ser Lys Tyr Thr Arg Lys Lys Ser Tyr Tyr
                 485                 490                 495
Thr Val Ser Tyr Trp Glu Gln Val Lys Leu Cys Thr Gln Arg Gly Phe
             500                 505                 510
Gln Arg Ile Tyr Gly Asn Lys Ser Tyr Thr Val Ile Asn Val Cys Ser
```

```
                515                 520                 525
Ala Ile Ile Gln Ser Phe Ile Thr Gly Ser Leu Phe Tyr Asn Thr Pro
    530                 535                 540

Ser Ser Thr Ser Gly Ala Phe Ser Arg Gly Gly Val Leu Tyr Phe Ala
545                 550                 555                 560

Leu Leu Tyr Tyr Ser Leu Met Gly Leu Ala Asn Ile Ser Phe Glu His
                565                 570                 575

Arg Pro Ile Leu Gln Lys His Lys Gly Tyr Ser Leu Tyr His Pro Ser
            580                 585                 590

Ala Glu Ala Ile Gly Ser Thr Leu Ala Ser Phe Pro Phe Arg Met Ile
        595                 600                 605

Gly Leu Thr Cys Phe Phe Ile Ile Leu Phe Phe Leu Ser Gly Leu His
    610                 615                 620

Arg Thr Ala Gly Ser Phe Phe Thr Ile Tyr Leu Phe Leu Thr Met Cys
625                 630                 635                 640

Ser Glu Ala Ile Asn Gly Leu Phe Glu Met Val Ser Ser Val Cys Asp
                645                 650                 655

Thr Leu Ser Gln Ala Asn Ser Ile Ser Gly Ile Leu Met Met Ser Ile
            660                 665                 670

Ser Met Tyr Ser Thr Tyr Met Ile Gln Leu Pro Ser Met His Pro Trp
        675                 680                 685

Phe Lys Trp Ile Ser Tyr Val Leu Pro Ile Arg Tyr Ala Phe Glu Ser
    690                 695                 700

Met Leu Asn Ala Glu Phe His Gly Arg His Met Asp Cys Ala Asn Thr
705                 710                 715                 720

Leu Val Pro Ser Gly Gly Asp Tyr Asp Asn Leu Ser Asp Asp Tyr Lys
                725                 730                 735

Val Cys Ala Phe Val Gly Ser Lys Pro Gly Gln Ser Tyr Val Leu Gly
            740                 745                 750

Asp Asp Tyr Leu Lys Asn Gln Phe Gln Tyr Val Tyr Lys His Thr Trp
        755                 760                 765

Arg Asn Phe Gly Ile Leu Trp Cys Phe Leu Leu Gly Tyr Val Val Leu
    770                 775                 780

Lys Val Ile Phe Thr Glu Tyr Lys Arg Pro Val Lys Gly Gly Gly Asp
785                 790                 795                 800

Ala Leu Ile Phe Lys Lys Gly Ser Lys Arg Phe Ile Ala His Ala Asp
                805                 810                 815

Glu Glu Ser Pro Asp Asn Val Asn Asp Ile Asp Ala Lys Glu Gln Phe
            820                 825                 830

Ser Ser Glu Ser Ser Gly Ala Asn Asp Glu Val Phe Asp Asp Leu Glu
        835                 840                 845

Ala Lys Gly Val Phe Ile Trp Lys Asp Val Cys Phe Thr Ile Pro Tyr
    850                 855                 860

Glu Gly Gly Lys Arg Met Leu Leu Asp Asn Val Ser Gly Tyr Cys Ile
865                 870                 875                 880

Pro Gly Thr Met Thr Ala Leu Met Gly Glu Ser Gly Ala Gly Lys Thr
                885                 890                 895

Thr Leu Leu Asn Thr Leu Ala Gln Arg Asn Val Gly Ile Ile Thr Gly
            900                 905                 910

Asp Met Leu Val Asn Gly Arg Pro Ile Asp Ala Ser Phe Glu Arg Arg
        915                 920                 925

Thr Gly Tyr Val Gln Gln Gln Asp Ile His Ile Ala Glu Leu Thr Val
    930                 935                 940
```

-continued

```
Arg Glu Ser Leu Gln Phe Ser Ala Arg Met Arg Arg Pro Gln His Leu
945                 950                 955                 960

Pro Asp Ser Glu Lys Met Asp Tyr Val Glu Lys Ile Ile Arg Val Leu
            965                 970                 975

Gly Met Glu Glu Tyr Ala Glu Ala Leu Val Gly Glu Val Gly Cys Gly
                980                 985                 990

Leu Asn Val Glu Gln Arg Lys Lys Leu Ser Ile Gly Val Glu Leu Val
            995                 1000                1005

Ala Lys Pro Asp Leu Leu Phe Leu Asp Glu Pro Thr Ser Gly
    1010                1015                1020

Leu Asp Ser Gln Ser Ser Trp Ala Ile Ile Gln Leu Leu Arg Lys
    1025                1030                1035

Leu Ser Lys Ala Gly Gln Ser Ile Leu Cys Thr Ile His Gln Pro
    1040                1045                1050

Ser Ala Thr Leu Phe Glu Glu Phe Asp Arg Leu Leu Leu Leu Arg
    1055                1060                1065

Lys Gly Gly Gln Thr Val Tyr Phe Gly Asp Ile Gly Lys Asn Ser
    1070                1075                1080

Ala Thr Ile Leu Asn Tyr Phe Glu Arg Asn Gly Ala Arg Lys Cys
    1085                1090                1095

Asp Ser Ser Glu Asn Pro Ala Glu Tyr Ile Leu Glu Ala Ile Gly
    1100                1105                1110

Ala Gly Ala Thr Ala Ser Val Lys Glu Asp Trp His Glu Lys Trp
    1115                1120                1125

Leu Asn Ser Val Glu Phe Glu Gln Thr Lys Glu Lys Val Gln Asp
    1130                1135                1140

Leu Ile Asn Asp Leu Ser Lys Gln Glu Thr Lys Ser Glu Val Gly
    1145                1150                1155

Asp Lys Pro Ser Lys Tyr Ala Thr Ser Tyr Ala Tyr Gln Phe Arg
    1160                1165                1170

Tyr Val Leu Ile Arg Thr Ser Thr Ser Phe Trp Arg Ser Leu Asn
    1175                1180                1185

Tyr Ile Met Ser Lys Met Met Leu Met Leu Val Gly Gly Leu Tyr
    1190                1195                1200

Ile Gly Phe Thr Phe Phe Asn Val Gly Lys Ser Tyr Val Gly Leu
    1205                1210                1215

Gln Asn Ala Met Phe Ala Ala Phe Ile Ser Ile Leu Ser Ala
    1220                1225                1230

Pro Ala Met Asn Gln Ile Gln Gly Arg Ala Ile Ala Ser Arg Glu
    1235                1240                1245

Leu Phe Glu Val Arg Glu Ser Gln Ser Asn Met Phe His Trp Ser
    1250                1255                1260

Leu Val Leu Ile Thr Gln Tyr Leu Ser Glu Leu Pro Tyr His Leu
    1265                1270                1275

Phe Phe Ser Thr Ile Phe Phe Val Ser Ser Tyr Phe Pro Leu Arg
    1280                1285                1290

Ile Phe Phe Glu Ala Ser Arg Ser Ala Val Tyr Phe Leu Asn Tyr
    1295                1300                1305

Cys Ile Met Phe Gln Leu Tyr Tyr Val Gly Leu Gly Leu Met Ile
    1310                1315                1320

Leu Tyr Met Ser Pro Asn Leu Pro Ser Ala Asn Val Ile Leu Gly
    1325                1330                1335
```

```
Leu Cys Leu Ser Phe Met Leu Ser Phe Cys Gly Val Thr Gln Pro
    1340                1345                1350

Val Ser Leu Met Pro Gly Phe Trp Thr Phe Met Trp Lys Ala Ser
    1355                1360                1365

Pro Tyr Thr Tyr Phe Val Gln Asn Leu Val Gly Ile Met Leu His
    1370                1375                1380

Lys Lys Pro Val Val Cys Lys Lys Glu Leu Asn Tyr Phe Asn
    1385                1390                1395

Pro Pro Asn Gly Ser Thr Cys Gly Glu Tyr Met Lys Pro Phe Leu
    1400                1405                1410

Glu Lys Ala Thr Gly Tyr Ile Glu Asn Pro Asp Ala Thr Ser Asp
    1415                1420                1425

Cys Ala Tyr Cys Ile Tyr Glu Val Gly Asp Asn Tyr Leu Thr His
    1430                1435                1440

Ile Ser Ser Lys Tyr Ser Tyr Leu Trp Arg Asn Phe Gly Ile Phe
    1445                1450                1455

Trp Ile Tyr Ile Phe Phe Asn Ile Ile Ala Met Val Cys Val Tyr
    1460                1465                1470

Tyr Leu Phe His Val Arg Gln Ser Ser Phe Leu Ser Pro Val Ser
    1475                1480                1485

Ile Leu Asn Lys Ile Lys Asn Ile Arg Lys Lys Lys Gln
    1490                1495                1500

<210> SEQ ID NO 3
<211> LENGTH: 1564
<212> TYPE: PRT
<213> ORGANISM: Saccharomyces cerevisiae

<400> SEQUENCE: 3

Met Leu Gln Ala Pro Ser Ser Asn Ser Gly Leu Asn Gln Gly Asn
1               5                   10                  15

Ala Ala Pro Asp Gly Pro Pro Asn Glu Thr Gln Pro Tyr Glu Gly Leu
                20                  25                  30

Asp Ala Ala Ala Gln Glu Glu Ile Lys Glu Leu Ala Arg Thr Leu Thr
                35                  40                  45

Ser Gln Ser Ser Leu Leu Ser Gln Glu Lys Arg Ile Ile Gly Thr Gly
    50                  55                  60

Asp Pro Asn Thr Leu Thr Ala Ala Ser Ser Ser Leu Ser Arg Ser
65                  70                  75                  80

Ile Phe Ala Ser Asp Ile Lys Gly Val Asn Pro Ile Leu Leu Asp Val
                85                  90                  95

Asn Asp Pro Asp Tyr Asp Glu Thr Leu Asp Pro Arg Ser Glu Asn Phe
                100                 105                 110

Ser Ser Val Arg Trp Val Arg Asn Met Ala Gln Ile Cys Glu Asn Asp
                115                 120                 125

Ser Asp Phe Tyr Lys Pro Phe Ser Leu Gly Cys Ala Trp Lys Asp Leu
                130                 135                 140

Ser Ala Ser Gly Asp Ser Ala Asp Ile Thr Tyr Gln Gly Thr Phe Gly
145                 150                 155                 160

Asn Met Pro Ile Lys Tyr Leu Lys Met Ser Trp Arg Cys Ile Ser Arg
                165                 170                 175

Arg Leu Phe His Arg Thr His Gly Lys Ser Glu Asp Asn Asp Ser Gly
                180                 185                 190

Phe Gln Ile Leu Lys Pro Met Asp Gly Cys Ile Asn Pro Gly Glu Leu
                195                 200                 205
```

```
Leu Val Val Leu Gly Arg Pro Gly Ala Gly Cys Thr Thr Leu Leu Lys
            210                 215                 220

Ser Ile Ser Val Asn Thr His Gly Phe Lys Ile Ser Pro Asp Thr Ile
225                 230                 235                 240

Ile Thr Tyr Asn Gly Phe Ser Asn Lys Glu Ile Lys Asn His Tyr Arg
                245                 250                 255

Gly Glu Val Val Tyr Asn Ala Glu Ser Asp Ile His Ile Pro His Leu
            260                 265                 270

Thr Val Phe Gln Thr Leu Tyr Thr Val Ala Arg Leu Lys Thr Pro Arg
            275                 280                 285

Asn Arg Ile Lys Gly Val Asp Arg Asp Thr Phe Ala Lys His Met Thr
            290                 295                 300

Glu Val Ala Met Ala Thr Tyr Gly Leu Ser His Thr Ala Asp Thr Lys
305                 310                 315                 320

Val Gly Asn Asp Phe Val Arg Gly Val Ser Gly Glu Arg Lys Arg
            325                 330                 335

Val Ser Ile Ala Glu Val Ser Ile Cys Gly Ser Lys Phe Gln Cys Trp
            340                 345                 350

Asp Asn Ala Thr Arg Gly Leu Asp Ser Ala Thr Ala Leu Glu Phe Ile
            355                 360                 365

Lys Ala Leu Lys Thr Gln Ala Thr Ile Thr Lys Ser Ala Ala Thr Val
370                 375                 380

Ala Ile Tyr Gln Cys Ser Lys Asp Ala Tyr Asp Leu Phe Asp Lys Val
385                 390                 395                 400

Cys Val Leu Tyr Asp Gly Tyr Gln Ile Phe Phe Gly Pro Ser Lys Gln
                405                 410                 415

Ala Lys Lys Tyr Phe Gln Arg Met Gly Tyr Val Cys Pro Glu Arg Gln
            420                 425                 430

Thr Thr Ala Asp Tyr Leu Thr Ser Ile Thr Ser Pro Ser Glu Arg Ile
            435                 440                 445

Lys Asp Lys Asp Met Val Lys His Gly Ile Met Ile Pro Gln Thr Ala
450                 455                 460

Tyr Glu Met Asn Gln Tyr Trp Ile Gln Ser Glu Glu Tyr Lys Gln Leu
465                 470                 475                 480

Gln Val Gln Val Asn Lys His Leu Asp Thr Asp Ser Ser Gln Gln Arg
            485                 490                 495

Glu Gln Ile Lys Asn Ala His Ile Ala Lys Gln Ser Lys Arg Ala Arg
            500                 505                 510

Pro Ser Ser Pro Tyr Thr Val Ser Phe Phe Leu Gln Val Lys Tyr Ile
            515                 520                 525

Leu Ile Arg Asp Ile Trp Arg Ile Lys Asn Asp Pro Ser Ile Gln Leu
            530                 535                 540

Phe Thr Val Leu Ser His Ala Ala Met Ala Leu Ile Leu Gly Ser Met
545                 550                 555                 560

Phe Tyr Glu Val Met Leu Ser Thr Thr Thr Thr Phe Tyr Tyr Arg
                565                 570                 575

Gly Ala Ala Ile Phe Phe Ala Ile Leu Phe Asn Ala Phe Ser Ser Leu
            580                 585                 590

Leu Glu Ile Phe Ser Leu Tyr Glu Thr Arg Pro Ile Thr Glu Lys His
            595                 600                 605

Lys Thr Tyr Ser Leu Tyr Arg Pro Ser Ala Asp Ala Phe Ala Ser Thr
610                 615                 620
```

-continued

```
Phe Ser Asp Val Pro Thr Lys Leu Ala Thr Ala Val Thr Phe Asn Ile
625                 630                 635                 640

Pro Tyr Tyr Phe Leu Ile Asn Leu Lys Arg Asp Ala Gly Ala Phe Phe
        645                 650                 655

Phe Tyr Phe Leu Ile Asn Ile Ile Thr Val Phe Ala Met Ser His Leu
        660                 665                 670

Phe Arg Cys Ile Gly Ser Val Ser Lys Thr Leu Pro Gln Ala Met Val
        675                 680                 685

Pro Ala Ser Val Leu Leu Leu Ala Phe Ala Met Tyr Thr Gly Phe Ala
690                 695                 700

Ile Pro Arg Val Gln Met Leu Gly Trp Ser Lys Trp Ile Ser Tyr Ile
705                 710                 715                 720

Asn Pro Leu Ser Tyr Leu Phe Glu Ser Leu Met Ile Asn Glu Phe His
                725                 730                 735

Gly Arg Asn Phe Pro Cys Ala Gln Tyr Ile Pro Ser Gly Pro Asn Tyr
                740                 745                 750

Val Asn Ala Thr Gly Asp Glu Val Thr Cys Ser Ala Leu Gly Ser Ile
                755                 760                 765

Pro Gly Asn Asn Tyr Val Ser Gly Asp Asp Phe Ile Gln Thr Asn Tyr
770                 775                 780

Gly Tyr Arg His Lys Asn Lys Trp Arg Ser Val Gly Ile Gly Leu Ala
785                 790                 795                 800

Tyr Ile Ile Phe Phe Leu Phe Leu Tyr Leu Phe Cys Glu Tyr Asn
                805                 810                 815

Glu Gly Ala Lys Gln Asn Gly Glu Met Leu Val Phe Pro His Ser Val
            820                 825                 830

Val Lys Lys Met Lys Lys Lys Gly Ile Val Ser Glu Lys Lys Lys Lys
                835                 840                 845

Asn Gln Pro Thr Leu Ser Thr Ser Asp Ala Glu Lys Asp Val Glu Met
850                 855                 860

Asn Asn Asn Ser Ser Ala Thr Asp Ser Arg Phe Leu Arg Asp Ser Asp
865                 870                 875                 880

Ala Ala Ile Met Gly Asn Asp Lys Thr Val Ala Lys Glu His Tyr Ser
                885                 890                 895

Ser Pro Ser Ser Ser Ala Ser Gln Ser Asn Ser Phe Ser Lys Ser Asp
                900                 905                 910

Asp Ile Glu Leu Ser Lys Ser Gln Ala Ile Phe His Trp Lys Asn Leu
            915                 920                 925

Cys Tyr Asp Ile Pro Ile Lys Asn Gly Lys Arg Ile Leu Asp Asn
930                 935                 940

Val Asp Gly Trp Val Lys Pro Gly Thr Leu Thr Ala Leu Ile Gly Ala
945                 950                 955                 960

Ser Gly Ala Gly Lys Thr Thr Leu Leu Asp Cys Leu Ala Glu Arg Thr
                965                 970                 975

Thr Met Gly Leu Ile Thr Gly Asp Val Phe Val Asp Gly Arg Pro Arg
            980                 985                 990

Asp Gln Ser Phe Pro Arg Ser Ile Gly Tyr Cys Gln Gln Gln Asp Leu
            995                 1000                1005

His Leu Lys Thr Ala Thr Val Arg Glu Ser Leu Arg Phe Ser Ala
        1010                1015                1020

Tyr Leu Arg Gln Ala Asp Asp Val Ser Ile Glu Glu Lys Asp Lys
        1025                1030                1035

Tyr Val Glu Glu Val Ile Glu Val Leu Glu Met Lys Leu Tyr Ala
```

-continued

```
                1040                1045                1050
Asp Ala Ile Val Gly Val Pro Gly Glu Gly Leu Asn Val Glu Gln
    1055                1060                1065
Arg Lys Arg Leu Thr Ile Gly Val Glu Leu Ala Ala Lys Pro Lys
    1070                1075                1080
Leu Leu Val Phe Leu Asp Glu Pro Thr Ser Gly Leu Asp Ser Gln
    1085                1090                1095
Thr Ala Trp Ser Thr Cys Gln Leu Met Lys Lys Leu Ala Ser Arg
    1100                1105                1110
Gly Gln Ala Ile Leu Cys Thr Ile His Gln Pro Ser Ala Leu Leu
    1115                1120                1125
Met Gln Glu Phe Asp Arg Leu Leu Phe Leu Gln Glu Gly Gly Gln
    1130                1135                1140
Thr Val Tyr Phe Gly Glu Leu Gly Lys Gly Cys Lys Thr Met Ile
    1145                1150                1155
Asn Tyr Phe Glu Ala His Gly Ala His Lys Cys Pro Pro Asp Ala
    1160                1165                1170
Asn Pro Ala Glu Trp Met Leu Glu Ile Val Gly Ala Ala Pro Gly
    1175                1180                1185
Thr His Ala Ser Gln Asp Tyr Phe Ala Ile Trp Arg Asp Ser Glu
    1190                1195                1200
Glu Tyr Arg Glu Met Gln Lys Glu Leu Asp Trp Met Glu Arg Glu
    1205                1210                1215
Leu Pro Lys Arg Thr Glu Gly Ser Ser Asn Glu Glu Gln Lys Glu
    1220                1225                1230
Phe Ala Thr Ser Thr Leu Tyr Gln Ile Lys Leu Val Ser Tyr Arg
    1235                1240                1245
Leu Phe His Gln Tyr Trp Arg Thr Pro Phe Tyr Leu Trp Ser Lys
    1250                1255                1260
Phe Phe Ser Thr Ile Val Ser Glu Leu Phe Ile Gly Phe Thr Phe
    1265                1270                1275
Phe Lys Ala Asn Thr Ser Leu Gln Gly Leu Gln Asn Gln Met Leu
    1280                1285                1290
Ala Ile Phe Met Phe Thr Val Val Phe Asn Pro Ile Leu Gln Gln
    1295                1300                1305
Tyr Leu Pro Leu Phe Val Gln Gln Arg Glu Leu Tyr Glu Ala Arg
    1310                1315                1320
Glu Arg Pro Ser Arg Thr Phe Ser Trp Lys Ala Phe Ile Val Ser
    1325                1330                1335
Gln Ile Leu Val Glu Ile Pro Trp Asn Leu Leu Ala Gly Thr Ile
    1340                1345                1350
Ala Phe Phe Val Tyr Tyr Tyr Pro Val Gly Phe Tyr Arg Asn Ala
    1355                1360                1365
Ser Tyr Ala Asn Gln Leu His Glu Arg Gly Ala Leu Phe Trp Leu
    1370                1375                1380
Phe Ala Cys Ala Phe Tyr Val Tyr Ile Ser Ser Met Gly Val Leu
    1385                1390                1395
Val Ile Ser Cys Ile Glu Ile Ala Glu Asn Ala Ala Asn Leu Ala
    1400                1405                1410
Ser Leu Phe Phe Ile Met Ser Leu Ser Phe Cys Gly Val Leu Ala
    1415                1420                1425
Thr Pro Asn Ile Leu Pro Arg Phe Trp Ile Phe Met Tyr Arg Val
    1430                1435                1440
```

```
Ser Pro Leu Thr Tyr Leu Ile Asp Ala Leu Leu Ser Val Gly Leu
    1445            1450                1455

Ala Asn Ala Ser Val Val Cys Ser Ser Asn Glu Leu Leu Lys Ile
1460                1465                1470

Val Pro Pro Ser Gly Met Thr Cys Ser Glu Tyr Met Glu Pro Tyr
    1475            1480                1485

Met Gln Ser Thr Gly Thr Gly Tyr Leu Leu Asp Gly Ser Ser Glu
    1490            1495                1500

Thr Glu Cys His Phe Cys Gln Phe Ser Ser Thr Asn Asp Tyr Leu
    1505            1510                1515

Ala Thr Val Ser Ser Ser Tyr Ser Arg Arg Trp Met Asn Tyr Gly
    1520            1525                1530

Ile Phe Ser Ala Tyr Ile Val Phe Asp Tyr Cys Ala Ala Ile Phe
    1535            1540                1545

Leu Tyr Trp Leu Val Arg Val Pro Lys Lys Ser Lys Lys Leu Lys
    1550            1555                1560

Lys

<210> SEQ ID NO 4
<211> LENGTH: 1411
<212> TYPE: PRT
<213> ORGANISM: Saccharomyces cerevisiae

<400> SEQUENCE: 4

Met Ser Leu Ser Lys Tyr Phe Asn Pro Ile Pro Asp Ala Ser Val Thr
1               5                   10                  15

Phe Asp Gly Ala Thr Val Gln Leu Glu Glu Ser Leu Gly Ala Val Gln
                20                  25                  30

Asn Asp Glu Glu Ser Ala Ser Glu Phe Lys Asn Val Gly His Leu Glu
            35                  40                  45

Ile Ser Asp Ile Thr Phe Arg Ala Asn Glu Gly Glu Val Val Leu Val
        50                  55                  60

Leu Gly Asn Pro Thr Ser Ala Leu Phe Lys Gly Leu Phe His Gly His
65                  70                  75                  80

Lys His Leu Lys Tyr Ser Pro Glu Gly Ser Ile Arg Phe Lys Asp Asn
                85                  90                  95

Glu Tyr Lys Gln Phe Ala Ser Lys Cys Pro His Gln Ile Ile Tyr Asn
            100                 105                 110

Asn Glu Gln Asp Ile His Phe Pro Tyr Leu Thr Val Glu Gln Thr Ile
        115                 120                 125

Asp Phe Ala Leu Ser Cys Lys Phe His Ile Pro Lys Gln Glu Arg Ile
    130                 135                 140

Glu Met Arg Asp Glu Leu Leu Lys Glu Phe Gly Leu Ser His Val Lys
145                 150                 155                 160

Lys Thr Tyr Val Gly Asn Asp Tyr Val Arg Gly Val Ser Gly Gly Glu
                165                 170                 175

Arg Lys Arg Ile Ser Ile Ile Glu Thr Phe Ile Ala Asn Gly Ser Val
            180                 185                 190

Tyr Leu Trp Asp Asn Ser Thr Lys Gly Leu Asp Ser Ala Thr Ala Leu
        195                 200                 205

Glu Phe Leu Ser Ile Thr Gln Lys Met Ala Lys Ala Thr Arg Ser Val
    210                 215                 220

Asn Phe Val Lys Ile Ser Gln Ala Ser Asp Lys Ile Val Ser Lys Phe
225                 230                 235                 240
```

```
Asp Lys Ile Leu Met Leu Gly Asp Ser Phe Gln Val Phe Tyr Gly Thr
            245                 250                 255
Met Glu Glu Cys Leu Thr His Phe His Asp Thr Leu Gln Ile Lys Lys
            260                 265                 270
Asn Pro Asn Asp Cys Ile Ile Glu Tyr Leu Thr Ser Ile Leu Asn Phe
            275                 280                 285
Lys Phe Lys Glu Thr Ser Asn Ser Ile Val Gly Leu Asp Thr Pro Ser
            290                 295                 300
Val Val Ser Glu Glu Asn Gln Ala Leu Asn Ile Asn Asn Glu Thr Asp
305                 310                 315                 320
Leu His Thr Leu Trp Ile Gln Ser Pro Tyr Tyr Lys His Trp Lys Ala
            325                 330                 335
Ile Thr Ser Lys Thr Val Gln Glu Cys Thr Arg Lys Asp Val Asn Pro
            340                 345                 350
Asp Asp Ile Ser Pro Ile Phe Ser Ile Pro Leu Lys Thr Gln Leu Lys
            355                 360                 365
Thr Cys Thr Val Arg Ala Phe Glu Arg Ile Ile Gly Asp Arg Asn Tyr
            370                 375                 380
Leu Ile Ser Gln Phe Val Ser Val Val Gln Ser Leu Val Ile Gly
385                 390                 395                 400
Ser Leu Phe Tyr Asn Ile Pro Leu Thr Thr Ile Gly Ser Phe Ser Arg
            405                 410                 415
Gly Ser Leu Thr Phe Phe Ser Ile Leu Phe Phe Thr Phe Leu Ser Leu
            420                 425                 430
Ala Asp Met Pro Ala Ser Phe Gln Arg Gln Pro Val Val Arg Lys His
            435                 440                 445
Val Gln Leu His Phe Tyr Tyr Asn Trp Val Glu Thr Leu Ala Thr Asn
450                 455                 460
Phe Phe Asp Cys Cys Ser Lys Phe Ile Leu Val Val Ile Phe Thr Ile
465                 470                 475                 480
Ile Leu Tyr Phe Leu Ala His Leu Gln Tyr Asn Ala Ala Arg Phe Phe
            485                 490                 495
Ile Phe Leu Leu Phe Leu Ser Val Tyr Asn Phe Cys Met Val Ser Leu
            500                 505                 510
Phe Ala Leu Thr Ala Leu Ile Ala Pro Thr Leu Ser Met Ala Asn Leu
            515                 520                 525
Leu Ala Gly Ile Leu Leu Ala Ile Ala Met Tyr Ala Ser Tyr Val
            530                 535                 540
Ile Tyr Met Lys Asp Met His Pro Trp Phe Ile Trp Ile Ala Tyr Leu
545                 550                 555                 560
Asn Pro Ala Met Phe Ala Met Glu Ala Ile Leu Ser Asn Glu Leu Phe
            565                 570                 575
Asn Leu Lys Leu Asp Cys His Glu Ser Ile Ile Pro Arg Gly Glu Tyr
            580                 585                 590
Tyr Asp Asn Ile Ser Phe Ser His Lys Ala Cys Ala Trp Gln Gly Ala
            595                 600                 605
Thr Leu Gly Asn Asp Tyr Val Arg Gly Arg Asp Tyr Leu Lys Ser Gly
            610                 615                 620
Leu Lys Tyr Thr Tyr His His Val Trp Arg Asn Phe Gly Ile Ile Ile
625                 630                 635                 640
Gly Phe Leu Cys Phe Phe Leu Phe Cys Ser Leu Leu Ala Ala Glu Tyr
            645                 650                 655
```

-continued

```
Ile Thr Pro Leu Phe Thr Arg Glu Asn Leu Leu Arg Trp Asn Asn Tyr
            660                 665                 670

Leu Lys Arg Tyr Cys Pro Phe Leu Asn Ser Gln Lys Lys Asn Asn Lys
    675                 680                 685

Ser Ala Ile Thr Asn Asn Asp Gly Val Cys Thr Pro Lys Thr Pro Ile
690                 695                 700

Ala Asn Phe Ser Thr Ser Ser Ser Val Pro Ser Val Ser His Gln
705                 710                 715                 720

Tyr Asp Thr Asp Tyr Asn Ile Lys His Pro Asp Glu Thr Val Asn Asn
                725                 730                 735

His Thr Lys Glu Ser Val Ala Met Glu Thr Gln Lys His Val Ile Ser
            740                 745                 750

Trp Lys Asn Ile Asn Tyr Thr Ile Gly Asp Lys Lys Leu Ile Asn Asp
        755                 760                 765

Ala Ser Gly Tyr Ile Ser Ser Gly Leu Thr Ala Leu Met Gly Glu Ser
    770                 775                 780

Gly Ala Gly Lys Thr Thr Leu Leu Asn Val Leu Ser Gln Arg Thr Glu
785                 790                 795                 800

Ser Gly Val Val Thr Gly Glu Leu Leu Ile Asp Gly Gln Pro Leu Thr
                805                 810                 815

Asn Ile Asp Ala Phe Arg Arg Ser Ile Gly Phe Val Gln Gln Gln Asp
            820                 825                 830

Val His Leu Glu Leu Leu Thr Val Arg Glu Ser Leu Glu Ile Ser Cys
        835                 840                 845

Val Leu Arg Gly Asp Gly Asp Arg Asp Tyr Leu Gly Val Val Ser Asn
    850                 855                 860

Leu Leu Arg Leu Pro Ser Glu Lys Leu Val Ala Asp Leu Ser Pro Thr
865                 870                 875                 880

Gln Arg Lys Leu Leu Ser Ile Gly Val Glu Leu Val Thr Lys Pro Ser
                885                 890                 895

Leu Leu Leu Phe Leu Asp Glu Pro Thr Ser Gly Leu Asp Ala Glu Ala
            900                 905                 910

Ala Leu Thr Ile Val Gln Phe Leu Lys Lys Leu Ser Met Gln Gly Gln
        915                 920                 925

Ala Ile Leu Cys Thr Ile His Gln Pro Ser Lys Ser Val Ile Ser Tyr
    930                 935                 940

Phe Asp Asn Ile Tyr Leu Leu Lys Arg Gly Gly Glu Cys Val Tyr Phe
945                 950                 955                 960

Gly Ser Leu Pro Asn Ala Cys Asp Tyr Phe Val Ala His Asp Arg Arg
                965                 970                 975

Leu Thr Phe Asp Arg Glu Met Asp Asn Pro Ala Asp Phe Val Ile Asp
            980                 985                 990

Val Val Gly Ser Gly Ser Thr Asn Ile Pro Met Asp Asp Ala Glu Lys
        995                 1000                1005

Pro Thr Ser Ser Lys Ile Asp Glu Pro Val Ser Tyr His Lys Gln
    1010                1015                1020

Ser Asp Ser Ile Asn Trp Ala Glu Leu Trp Gln Ser Ser Pro Glu
    1025                1030                1035

Lys Val Arg Val Ala Asp Asp Leu Leu Leu Leu Glu Glu Glu Ala
    1040                1045                1050

Arg Lys Ser Gly Val Asp Phe Thr Thr Ser Val Trp Ser Pro Pro
    1055                1060                1065

Ser Tyr Met Glu Gln Ile Lys Leu Ile Thr Lys Arg Gln Tyr Ile
```

```
            1070                1075                1080

Cys  Thr  Lys  Arg  Asp  Met  Thr  Tyr  Val  Phe  Ala  Lys  Tyr  Ala  Leu
          1085                1090                1095

Asn  Ala  Gly  Ala  Gly  Leu  Phe  Ile  Gly  Phe  Ser  Phe  Trp  Arg  Thr
          1100                1105                1110

Lys  His  Asn  Ile  Asn  Gly  Leu  Gln  Asp  Ala  Ile  Phe  Leu  Cys  Phe
          1115                1120                1125

Met  Met  Leu  Cys  Val  Ser  Ser  Pro  Leu  Ile  Asn  Gln  Val  Gln  Asp
          1130                1135                1140

Lys  Ala  Leu  Gln  Ser  Lys  Glu  Val  Tyr  Ile  Ala  Arg  Glu  Ala  Arg
          1145                1150                1155

Ser  Asn  Thr  Tyr  His  Trp  Thr  Val  Leu  Leu  Ile  Ala  Gln  Thr  Ile
          1160                1165                1170

Val  Glu  Leu  Pro  Leu  Ala  Ile  Ser  Ser  Ser  Thr  Leu  Phe  Phe  Leu
          1175                1180                1185

Cys  Cys  Tyr  Phe  Cys  Cys  Gly  Phe  Glu  Thr  Ser  Ala  Arg  Val  Ala
          1190                1195                1200

Gly  Val  Phe  Tyr  Leu  Asn  Tyr  Ile  Leu  Phe  Ser  Met  Tyr  Tyr  Leu
          1205                1210                1215

Ser  Phe  Gly  Leu  Trp  Leu  Leu  Tyr  Ser  Ala  Pro  Asp  Leu  Gln  Thr
          1220                1225                1230

Ala  Ala  Val  Phe  Val  Ala  Phe  Leu  Tyr  Ser  Phe  Thr  Ala  Ser  Phe
          1235                1240                1245

Cys  Gly  Val  Met  Gln  Pro  Tyr  Ser  Leu  Phe  Pro  Arg  Phe  Trp  Thr
          1250                1255                1260

Phe  Met  Tyr  Arg  Val  Ser  Pro  Tyr  Thr  Tyr  Phe  Ile  Glu  Thr  Phe
          1265                1270                1275

Val  Ser  Leu  Leu  Leu  His  Asp  Arg  Glu  Val  Asn  Cys  Ser  Thr  Ser
          1280                1285                1290

Glu  Met  Val  Pro  Ser  Gln  Pro  Val  Met  Gly  Gln  Thr  Cys  Gly  Gln
          1295                1300                1305

Phe  Met  Lys  Pro  Phe  Ile  Asp  Glu  Phe  Gly  Gly  Lys  Leu  His  Ile
          1310                1315                1320

Asn  Asn  Thr  Tyr  Thr  Val  Cys  Ala  Tyr  Cys  Met  Tyr  Thr  Val  Gly
          1325                1330                1335

Asp  Asp  Phe  Leu  Ala  Gln  Glu  Asn  Met  Ser  Tyr  His  His  Arg  Trp
          1340                1345                1350

Arg  Asn  Phe  Gly  Phe  Glu  Trp  Val  Phe  Val  Cys  Phe  Asn  Ile  Ala
          1355                1360                1365

Ala  Met  Phe  Val  Gly  Phe  Tyr  Leu  Thr  Tyr  Ile  Lys  Lys  Ile  Trp
          1370                1375                1380

Pro  Ser  Val  Ile  Asp  Gly  Ile  Lys  Lys  Cys  Ile  Pro  Ser  Met  Arg
          1385                1390                1395

Arg  Ser  Lys  Thr  Ser  His  Asn  Pro  Asn  Glu  Gln  Ser  Val
          1400                1405                1410

<210> SEQ ID NO 5
<211> LENGTH: 1511
<212> TYPE: PRT
<213> ORGANISM: Saccharomyces cerevisiae

<400> SEQUENCE: 5

Met  Ser  Ser  Thr  Asp  Glu  His  Ile  Glu  Lys  Asp  Ile  Ser  Ser  Arg  Ser
1                 5                   10                  15
```

```
Asn His Asp Asp Asp Tyr Ala Asn Ser Val Gln Ser Tyr Ala Ala Ser
            20                  25                  30

Glu Gly Gln Val Asp Asn Glu Asp Leu Ala Ala Thr Ser Gln Leu Ser
        35                  40                  45

Arg His Leu Ser Asn Ile Leu Ser Asn Glu Glu Gly Ile Glu Arg Leu
    50                  55                  60

Glu Ser Met Ala Arg Val Ile Ser His Lys Thr Lys Lys Glu Met Asp
65                  70                  75                  80

Ser Phe Glu Ile Asn Asp Leu Asp Phe Asp Leu Arg Ser Leu Leu His
                85                  90                  95

Tyr Leu Arg Ser Arg Gln Leu Glu Gln Gly Ile Glu Pro Gly Asp Ser
            100                 105                 110

Gly Ile Ala Phe Lys Asn Leu Thr Ala Val Gly Val Asp Ala Ser Ala
        115                 120                 125

Ala Tyr Gly Pro Ser Val Glu Glu Met Phe Arg Asn Ile Ala Ser Ile
    130                 135                 140

Pro Ala His Leu Ile Ser Lys Phe Thr Lys Lys Ser Asp Val Pro Leu
145                 150                 155                 160

Arg Asn Ile Ile Gln Asn Cys Thr Gly Val Val Glu Ser Gly Glu Met
                165                 170                 175

Leu Phe Val Val Gly Arg Pro Gly Ala Gly Cys Ser Thr Phe Leu Lys
            180                 185                 190

Cys Leu Ser Gly Glu Thr Ser Glu Leu Val Asp Val Gln Gly Glu Phe
        195                 200                 205

Ser Tyr Asp Gly Leu Asp Gln Ser Glu Met Met Ser Lys Tyr Lys Gly
    210                 215                 220

Tyr Val Ile Tyr Cys Pro Glu Leu Asp Phe His Phe Pro Lys Ile Thr
225                 230                 235                 240

Val Lys Glu Thr Ile Asp Phe Ala Leu Lys Cys Lys Thr Pro Arg Val
                245                 250                 255

Arg Ile Asp Lys Met Thr Arg Lys Gln Tyr Val Asp Asn Ile Arg Asp
            260                 265                 270

Met Trp Cys Thr Val Phe Gly Leu Arg His Thr Tyr Ala Thr Lys Val
        275                 280                 285

Gly Asn Asp Phe Val Arg Gly Val Ser Gly Gly Glu Arg Lys Arg Val
    290                 295                 300

Ser Leu Val Glu Ala Gln Ala Met Asn Ala Ser Ile Tyr Ser Trp Asp
305                 310                 315                 320

Asn Ala Thr Arg Gly Leu Asp Ala Ser Thr Ala Leu Glu Phe Ala Gln
                325                 330                 335

Ala Ile Arg Thr Ala Thr Asn Met Val Asn Asn Ser Ala Ile Val Ala
            340                 345                 350

Ile Tyr Gln Ala Gly Glu Asn Ile Tyr Glu Leu Phe Asp Lys Thr Thr
        355                 360                 365

Val Leu Tyr Asn Gly Arg Gln Ile Tyr Phe Gly Pro Ala Asp Lys Ala
    370                 375                 380

Val Gly Tyr Phe Gln Arg Met Gly Trp Val Lys Pro Asn Arg Met Thr
385                 390                 395                 400

Ser Ala Glu Phe Leu Thr Ser Val Thr Val Asp Phe Glu Asn Arg Thr
                405                 410                 415

Leu Asp Ile Lys Pro Gly Tyr Glu Asp Lys Val Pro Lys Ser Ser Ser
            420                 425                 430

Glu Phe Glu Glu Tyr Trp Leu Asn Ser Glu Asp Tyr Gln Glu Leu Leu
```

```
                435                 440                 445
Arg Thr Tyr Asp Asp Tyr Gln Ser Arg His Pro Val Asn Glu Thr Arg
450                 455                 460

Asp Arg Leu Asp Val Ala Lys Lys Gln Arg Leu Gln Gln Gly Gln Arg
465                 470                 475                 480

Glu Asn Ser Gln Tyr Val Val Asn Tyr Trp Thr Gln Val Tyr Tyr Cys
                485                 490                 495

Met Ile Arg Gly Phe Gln Arg Val Lys Gly Asp Ser Thr Tyr Thr Lys
                500                 505                 510

Val Tyr Leu Ser Ser Phe Leu Ile Lys Ala Leu Ile Ile Gly Ser Met
                515                 520                 525

Phe His Lys Ile Asp Asp Lys Ser Gln Ser Thr Thr Ala Gly Ala Tyr
                530                 535                 540

Ser Arg Gly Gly Met Leu Phe Tyr Val Leu Leu Phe Ala Ser Val Thr
545                 550                 555                 560

Ser Leu Ala Glu Ile Gly Asn Ser Phe Ser Ser Arg Pro Val Ile Val
                565                 570                 575

Lys His Lys Ser Tyr Ser Met Tyr His Leu Ser Ala Glu Ser Leu Gln
                580                 585                 590

Glu Ile Ile Thr Glu Phe Pro Thr Lys Phe Val Ala Ile Val Ile Leu
                595                 600                 605

Cys Leu Ile Thr Tyr Trp Ile Pro Phe Met Lys Tyr Glu Ala Gly Ala
610                 615                 620

Phe Phe Gln Tyr Ile Leu Tyr Leu Leu Thr Val Gln Gln Cys Thr Ser
625                 630                 635                 640

Phe Ile Phe Lys Phe Val Ala Thr Met Ser Lys Ser Gly Val Asp Ala
                645                 650                 655

His Ala Val Gly Gly Leu Trp Val Leu Met Leu Cys Val Tyr Ala Gly
                660                 665                 670

Phe Val Leu Pro Ile Gly Glu Met His His Trp Ile Arg Trp Leu His
                675                 680                 685

Phe Ile Asn Pro Leu Thr Tyr Ala Phe Glu Ser Leu Val Ser Thr Glu
                690                 695                 700

Phe His His Arg Glu Met Leu Cys Ser Ala Leu Val Pro Ser Gly Pro
705                 710                 715                 720

Gly Tyr Glu Gly Ile Ser Ile Ala Asn Gln Val Cys Asp Ala Ala Gly
                725                 730                 735

Ala Val Lys Gly Asn Leu Tyr Val Ser Gly Asp Ser Tyr Ile Leu His
                740                 745                 750

Gln Tyr His Phe Ala Tyr Lys His Ala Trp Arg Asn Trp Gly Val Asn
                755                 760                 765

Ile Val Trp Thr Phe Gly Tyr Ile Val Phe Asn Val Ile Leu Ser Glu
                770                 775                 780

Tyr Leu Lys Pro Val Glu Gly Gly Asp Leu Leu Tyr Lys Arg
785                 790                 795                 800

Gly His Met Pro Glu Leu Gly Thr Glu Asn Ala Asp Ala Arg Thr Ala
                805                 810                 815

Ser Arg Glu Glu Met Met Glu Ala Leu Asn Gly Pro Asn Val Asp Leu
                820                 825                 830

Glu Lys Val Ile Ala Glu Lys Asp Val Phe Thr Trp Asn His Leu Asp
                835                 840                 845

Tyr Thr Ile Pro Tyr Asp Gly Ala Thr Arg Lys Leu Leu Ser Asp Val
850                 855                 860
```

```
Phe Gly Tyr Val Lys Pro Gly Lys Met Thr Ala Leu Met Gly Glu Ser
865                 870                 875                 880

Gly Ala Gly Lys Thr Thr Leu Leu Asn Val Leu Ala Gln Arg Ile Asn
            885                 890                 895

Met Gly Val Ile Thr Gly Asp Met Leu Val Asn Ala Lys Pro Leu Pro
            900                 905                 910

Ala Ser Phe Asn Arg Ser Cys Gly Tyr Val Gln Ala Asp Asn His
        915                 920                 925

Met Ala Glu Leu Ser Val Arg Glu Ser Leu Arg Phe Ala Ala Glu Leu
930                 935                 940

Arg Gln Gln Ser Ser Val Pro Leu Glu Glu Lys Tyr Glu Tyr Val Glu
945                 950                 955                 960

Lys Ile Ile Thr Leu Leu Gly Met Gln Asn Tyr Ala Glu Ala Leu Val
            965                 970                 975

Gly Lys Thr Gly Arg Gly Leu Asn Val Glu Gln Arg Lys Lys Leu Ser
            980                 985                 990

Ile Gly Val Glu Leu Val Ala Lys Pro Ser Leu Leu Leu Phe Leu Asp
        995                 1000                1005

Glu Pro Thr Ser Gly Leu Asp Ser Gln Ser Ala Trp Ser Ile Val
    1010                1015                1020

Gln Phe Met Arg Ala Leu Ala Asp Ser Gly Gln Ser Ile Leu Cys
    1025                1030                1035

Thr Ile His Gln Pro Ser Ala Thr Leu Phe Glu Gln Phe Asp Arg
    1040                1045                1050

Leu Leu Leu Leu Lys Lys Gly Gly Lys Met Val Tyr Phe Gly Asp
    1055                1060                1065

Ile Gly Pro Asn Ser Glu Thr Leu Leu Lys Tyr Phe Glu Arg Gln
    1070                1075                1080

Ser Gly Met Lys Cys Gly Val Ser Glu Asn Pro Ala Glu Tyr Ile
    1085                1090                1095

Leu Asn Cys Ile Gly Ala Gly Ala Thr Ala Ser Val Asn Ser Asp
    1100                1105                1110

Trp His Asp Leu Trp Leu Ala Ser Pro Glu Cys Ala Ala Ala Arg
    1115                1120                1125

Ala Glu Val Glu Glu Leu His Arg Thr Leu Pro Gly Arg Ala Val
    1130                1135                1140

Asn Asp Asp Pro Glu Leu Ala Thr Arg Phe Ala Ala Ser Tyr Met
    1145                1150                1155

Thr Gln Ile Lys Cys Val Leu Arg Arg Thr Ala Leu Gln Phe Trp
    1160                1165                1170

Arg Ser Pro Val Tyr Ile Arg Ala Lys Phe Phe Glu Cys Val Ala
    1175                1180                1185

Cys Ala Leu Phe Val Gly Leu Ser Tyr Val Gly Val Asn His Ser
    1190                1195                1200

Val Gly Gly Ala Ile Glu Ala Phe Ser Ser Ile Phe Met Leu Leu
    1205                1210                1215

Leu Ile Ala Leu Ala Met Ile Asn Gln Leu His Val Phe Ala Tyr
    1220                1225                1230

Asp Ser Arg Glu Leu Tyr Glu Val Arg Glu Ala Ala Ser Asn Thr
    1235                1240                1245

Phe His Trp Ser Val Leu Leu Leu Cys His Ala Ala Val Glu Asn
    1250                1255                1260
```

```
Phe Trp Ser Thr Leu Cys Gln Phe Met Cys Phe Ile Cys Tyr Tyr
1265                1270                1275

Trp Pro Ala Gln Phe Ser Gly Arg Ala Ser His Ala Gly Phe Phe
    1280                1285                1290

Phe Phe Phe Tyr Val Leu Ile Phe Pro Leu Tyr Phe Val Thr Tyr
1295                1300                1305

Gly Leu Trp Ile Leu Tyr Met Ser Pro Asp Val Pro Ser Ala Ser
    1310                1315                1320

Met Ile Asn Ser Asn Leu Phe Ala Ala Met Leu Leu Phe Cys Gly
1325                1330                1335

Ile Leu Gln Pro Arg Glu Lys Met Pro Ala Phe Trp Arg Arg Leu
    1340                1345                1350

Met Tyr Asn Val Ser Pro Phe Thr Tyr Val Val Gln Ala Leu Val
1355                1360                1365

Thr Pro Leu Val His Asn Lys Lys Val Val Cys Asn Pro His Glu
    1370                1375                1380

Tyr Asn Ile Met Asp Pro Pro Ser Gly Lys Thr Cys Gly Glu Phe
1385                1390                1395

Leu Ser Thr Tyr Met Asp Asn Asn Thr Gly Tyr Leu Val Asn Pro
    1400                1405                1410

Thr Ala Thr Glu Asn Cys Gln Tyr Cys Pro Tyr Thr Val Gln Asp
1415                1420                1425

Gln Val Val Ala Lys Tyr Asn Val Lys Trp Asp His Arg Trp Arg
    1430                1435                1440

Asn Phe Gly Phe Met Trp Ala Tyr Ile Cys Phe Asn Ile Ala Ala
1445                1450                1455

Met Leu Ile Cys Tyr Tyr Val Val Arg Val Lys Val Trp Ser Leu
    1460                1465                1470

Lys Ser Val Leu Asn Phe Lys Lys Trp Phe Asn Gly Pro Arg Lys
1475                1480                1485

Glu Arg His Glu Lys Asp Thr Asn Ile Phe Gln Thr Val Pro Gly
    1490                1495                1500

Asp Glu Asn Lys Ile Thr Lys Lys
1505                1510

<210> SEQ ID NO 6
<211> LENGTH: 1529
<212> TYPE: PRT
<213> ORGANISM: Saccharomyces cerevisiae

<400> SEQUENCE: 6

Met Ser Ser Asp Ile Arg Asp Val Glu Glu Arg Asn Ser Arg Ser
1               5                   10                  15

Ser Ser Ser Ser Ser Asn Ser Ala Ala Gln Ser Ile Gly Gln His
                20                  25                  30

Pro Tyr Arg Gly Phe Asp Ser Glu Ala Ala Glu Arg Val His Glu Leu
            35                  40                  45

Ala Arg Thr Leu Thr Ser Gln Ser Leu Leu Tyr Thr Ala Asn Ser Asn
    50                  55                  60

Asn Ser Ser Ser Ser Asn His Asn Ala His Asn Ala Asp Ser Arg Ser
65                  70                  75                  80

Val Phe Ser Thr Asp Met Glu Gly Val Asn Pro Val Phe Thr Asn Pro
                85                  90                  95

Asp Thr Pro Gly Tyr Asn Pro Lys Leu Asp Pro Asn Ser Asp Gln Phe
            100                 105                 110
```

-continued

Ser Ser Thr Ala Trp Val Gln Asn Met Ala Asn Ile Cys Thr Ser Asp
    115                 120                 125

Pro Asp Phe Tyr Lys Pro Tyr Ser Leu Gly Cys Val Trp Lys Asn Leu
130                 135                 140

Ser Ala Ser Gly Asp Ser Ala Asp Val Ser Tyr Gln Ser Thr Phe Ala
145                 150                 155                 160

Asn Ile Val Pro Lys Leu Leu Thr Lys Gly Leu Arg Leu Leu Lys Pro
                165                 170                 175

Ser Lys Glu Glu Asp Thr Phe Gln Ile Leu Lys Pro Met Asp Gly Cys
            180                 185                 190

Leu Asn Pro Gly Glu Leu Leu Val Val Leu Gly Arg Pro Gly Ser Gly
        195                 200                 205

Cys Thr Thr Leu Leu Lys Ser Ile Ser Ser Asn Ser His Gly Phe Lys
    210                 215                 220

Ile Ala Lys Asp Ser Ile Val Ser Tyr Asn Gly Leu Ser Ser Ser Asp
225                 230                 235                 240

Ile Arg Lys His Tyr Arg Gly Glu Val Val Tyr Asn Ala Glu Ser Asp
                245                 250                 255

Ile His Leu Pro His Leu Thr Val Tyr Gln Thr Leu Phe Thr Val Ala
            260                 265                 270

Arg Met Lys Thr Pro Gln Asn Arg Ile Lys Gly Val Asp Arg Glu Ala
        275                 280                 285

Tyr Ala Asn His Val Thr Glu Val Ala Met Ala Thr Tyr Gly Leu Ser
    290                 295                 300

His Thr Arg Asp Thr Lys Val Gly Asn Asp Leu Val Arg Gly Val Ser
305                 310                 315                 320

Gly Gly Glu Arg Lys Arg Val Ser Ile Ala Glu Val Ala Ile Cys Gly
                325                 330                 335

Ala Arg Phe Gln Cys Trp Asp Asn Ala Thr Arg Gly Leu Asp Ser Ala
            340                 345                 350

Thr Ala Leu Glu Phe Ile Arg Ala Leu Lys Thr Gln Ala Asp Ile Gly
        355                 360                 365

Lys Thr Ala Ala Thr Val Ala Ile Tyr Gln Cys Ser Gln Asp Ala Tyr
    370                 375                 380

Asp Leu Phe Asp Lys Val Cys Val Leu Asp Asp Gly Tyr Gln Leu Tyr
385                 390                 395                 400

Phe Gly Pro Ala Lys Asp Ala Lys Lys Tyr Phe Gln Asp Met Gly Tyr
                405                 410                 415

Tyr Cys Pro Pro Arg Gln Thr Thr Ala Asp Phe Leu Thr Ser Ile Thr
            420                 425                 430

Ser Pro Thr Glu Arg Ile Ile Ser Lys Glu Phe Ile Glu Lys Gly Thr
        435                 440                 445

Arg Val Pro Gln Thr Pro Lys Asp Met Ala Glu Tyr Trp Leu Gln Ser
    450                 455                 460

Glu Ser Tyr Lys Asn Leu Ile Lys Asp Ile Asp Ser Thr Leu Glu Lys
465                 470                 475                 480

Asn Thr Asp Glu Ala Arg Asn Ile Ile Arg Asp Ala His His Ala Lys
                485                 490                 495

Gln Ala Lys Arg Ala Pro Pro Ser Ser Pro Tyr Val Asn Tyr Gly
            500                 505                 510

Met Gln Val Lys Tyr Leu Leu Ile Arg Asn Phe Trp Arg Met Lys Gln
    515                 520                 525

```
Ser Ala Ser Val Thr Leu Trp Gln Val Ile Gly Asn Ser Val Met Ala
    530                 535                 540
Phe Ile Leu Gly Ser Met Phe Tyr Lys Val Met Lys Lys Asn Asp Thr
545                 550                 555                 560
Ser Thr Phe Tyr Phe Arg Gly Ala Ala Met Phe Phe Ala Ile Leu Phe
                565                 570                 575
Asn Ala Phe Ser Cys Leu Leu Glu Ile Phe Ser Leu Tyr Glu Thr Arg
            580                 585                 590
Pro Ile Thr Glu Lys His Arg Thr Tyr Ser Leu Tyr His Pro Ser Ala
        595                 600                 605
Asp Ala Phe Ala Ser Val Leu Ser Glu Met Pro Pro Lys Leu Ile Thr
    610                 615                 620
Ala Val Cys Phe Asn Ile Ile Phe Tyr Phe Leu Val Asp Phe Arg Arg
625                 630                 635                 640
Asn Gly Gly Val Phe Phe Tyr Phe Leu Ile Asn Val Ile Ala Thr
                645                 650                 655
Phe Thr Leu Ser His Leu Phe Arg Cys Val Gly Ser Leu Thr Lys Thr
            660                 665                 670
Leu Gln Glu Ala Met Val Pro Ala Ser Met Leu Leu Leu Ala Ile Ser
        675                 680                 685
Met Tyr Thr Gly Phe Ala Ile Pro Lys Thr Lys Ile Leu Gly Trp Ser
    690                 695                 700
Ile Trp Ile Trp Tyr Ile Asn Pro Leu Ala Tyr Leu Phe Glu Ser Leu
705                 710                 715                 720
Met Ile Asn Glu Phe His Asp Arg Arg Phe Pro Cys Ala Gln Tyr Ile
                725                 730                 735
Pro Ala Gly Pro Ala Tyr Gln Asn Ile Thr Gly Thr Gln Arg Val Cys
            740                 745                 750
Ser Ala Val Gly Ala Tyr Pro Gly Asn Asp Tyr Val Leu Gly Asp Asp
        755                 760                 765
Phe Leu Lys Glu Ser Tyr Asp Tyr Glu His Lys His Lys Trp Arg Gly
    770                 775                 780
Phe Gly Ile Gly Met Ala Tyr Val Val Phe Phe Phe Val Tyr Leu
785                 790                 795                 800
Ile Leu Cys Glu Tyr Asn Glu Gly Ala Lys Gln Lys Gly Glu Met Val
                805                 810                 815
Val Phe Leu Arg Ser Lys Ile Lys Gln Leu Lys Lys Glu Gly Lys Leu
            820                 825                 830
Gln Glu Lys His Arg Pro Gly Asp Ile Glu Asn Asn Ala Gly Ser Ser
        835                 840                 845
Pro Asp Ser Ala Thr Thr Glu Lys Lys Ile Leu Asp Asp Ser Ser Glu
    850                 855                 860
Gly Ser Asp Ser Ser Ser Asp Asn Ala Gly Leu Gly Leu Ser Lys Ser
865                 870                 875                 880
Glu Ala Ile Phe His Trp Arg Asp Leu Cys Tyr Asp Val Pro Ile Lys
                885                 890                 895
Gly Gly Gln Arg Arg Ile Leu Asn Asn Val Asp Gly Trp Val Lys Pro
            900                 905                 910
Gly Thr Leu Thr Ala Leu Met Gly Ala Ser Gly Ala Gly Lys Thr Thr
        915                 920                 925
Leu Leu Asp Cys Leu Ala Glu Arg Val Thr Met Gly Val Ile Thr Gly
    930                 935                 940
Asn Ile Phe Val Asp Gly Arg Leu Arg Asp Glu Ser Phe Pro Arg Ser
```

-continued

```
            945               950               955               960
        Ile Gly Tyr Cys Gln Gln Gln Asp Leu His Leu Lys Thr Ala Thr Val
                        965               970               975
        Arg Glu Ser Leu Arg Phe Ser Ala Tyr Leu Arg Gln Pro Ser Ser Val
                        980               985               990
        Ser Ile Glu Glu Lys Asn Arg Tyr Val Glu Glu Val Ile Lys Ile Leu
                        995              1000              1005
        Glu Met Gln Gln Tyr Ser Asp Ala Val Val Gly Val Ala Gly Glu
                1010              1015              1020
        Gly Leu Asn Val Glu Gln Arg Lys Arg Leu Thr Ile Gly Val Glu
                1025              1030              1035
        Leu Ala Ala Arg Pro Lys Leu Leu Val Phe Leu Asp Glu Pro Thr
                1040              1045              1050
        Ser Gly Leu Asp Ser Gln Thr Ala Trp Asp Thr Cys Gln Leu Met
                1055              1060              1065
        Arg Lys Leu Ala Thr His Gly Gln Ala Ile Leu Cys Thr Ile His
                1070              1075              1080
        Gln Pro Ser Ala Ile Leu Met Gln Gln Phe Asp Arg Leu Leu Phe
                1085              1090              1095
        Leu Gln Lys Gly Gly Gln Thr Val Tyr Phe Gly Asp Leu Gly Glu
                1100              1105              1110
        Gly Cys Lys Thr Met Ile Asp Tyr Phe Glu Ser Lys Gly Ala His
                1115              1120              1125
        Lys Cys Pro Pro Asp Ala Asn Pro Ala Glu Trp Met Leu Glu Val
                1130              1135              1140
        Val Gly Ala Ala Pro Gly Ser His Ala Thr Gln Asp Tyr Asn Glu
                1145              1150              1155
        Val Trp Arg Asn Ser Asp Glu Tyr Lys Ala Val Gln Glu Glu Leu
                1160              1165              1170
        Asp Trp Met Glu Lys Asn Leu Pro Gly Arg Ser Lys Glu Pro Thr
                1175              1180              1185
        Ala Glu Glu His Lys Pro Phe Ala Ala Ser Leu Tyr Tyr Gln Phe
                1190              1195              1200
        Lys Met Val Thr Ile Arg Leu Phe Gln Gln Tyr Trp Arg Ser Pro
                1205              1210              1215
        Asp Tyr Leu Trp Ser Lys Phe Ile Leu Thr Ile Phe Asn Gln Val
                1220              1225              1230
        Phe Ile Gly Phe Thr Phe Phe Lys Ala Asp Arg Ser Leu Gln Gly
                1235              1240              1245
        Leu Gln Asn Gln Met Leu Ser Ile Phe Met Tyr Thr Val Ile Phe
                1250              1255              1260
        Asn Pro Ile Leu Gln Gln Tyr Leu Pro Ser Phe Val Gln Gln Arg
                1265              1270              1275
        Asp Leu Tyr Glu Ala Arg Glu Arg Pro Ser Arg Thr Phe Ser Trp
                1280              1285              1290
        Leu Ala Phe Phe Leu Ser Gln Ile Ile Val Glu Ile Pro Trp Asn
                1295              1300              1305
        Ile Leu Ala Gly Thr Ile Ala Tyr Cys Ile Tyr Tyr Tyr Ala Val
                1310              1315              1320
        Gly Phe Tyr Ala Asn Ala Ser Ala Ala Gly Gln Leu His Glu Arg
                1325              1330              1335
        Gly Ala Leu Phe Trp Leu Phe Ser Ile Ala Phe Tyr Val Tyr Ile
                1340              1345              1350
```

```
Gly Ser Met Gly Leu Leu Met Ile Ser Phe Asn Glu Val Ala Glu
    1355                1360                1365

Thr Ala Ala His Met Gly Thr Leu Leu Phe Thr Met Ala Leu Ser
    1370                1375                1380

Phe Cys Gly Val Met Ala Thr Pro Lys Val Met Pro Arg Phe Trp
    1385                1390                1395

Ile Phe Met Tyr Arg Val Ser Pro Leu Thr Tyr Met Ile Asp Ala
    1400                1405                1410

Leu Leu Ala Leu Gly Val Ala Asn Val Asp Val Lys Cys Ser Asn
    1415                1420                1425

Tyr Glu Met Val Lys Phe Thr Pro Pro Ser Gly Thr Thr Cys Gly
    1430                1435                1440

Asp Tyr Met Ala Ser Tyr Ile Lys Leu Ala Gly Thr Gly Tyr Leu
    1445                1450                1455

Ser Asp Pro Ser Ala Thr Asp Ile Cys Ser Phe Cys Ala Val Ser
    1460                1465                1470

Thr Thr Asn Ala Phe Leu Ala Thr Phe Ser Ser His Tyr Tyr Arg
    1475                1480                1485

Arg Trp Arg Asn Tyr Gly Ile Phe Ile Cys Tyr Ile Ala Phe Asp
    1490                1495                1500

Tyr Ile Ala Ala Thr Phe Leu Tyr Trp Leu Ser Arg Val Pro Lys
    1505                1510                1515

Lys Asn Gly Lys Ile Ser Glu Lys Pro Lys Lys
    1520                1525
```

<210> SEQ ID NO 7
<211> LENGTH: 1333
<212> TYPE: PRT
<213> ORGANISM: Saccharomyces cerevisiae

<400> SEQUENCE: 7

```
Met Glu Cys Val Ser Val Glu Gly Leu Asp Ser Ser Phe Leu Glu Gly
1               5                   10                  15

Gln Thr Phe Gly Asp Ile Leu Cys Leu Pro Trp Thr Ile Ile Lys Gly
            20                  25                  30

Ile Arg Glu Arg Lys Asn Arg Asn Lys Met Lys Ile Ile Leu Lys Asn
        35                  40                  45

Val Ser Leu Leu Ala Lys Ser Gly Glu Met Val Leu Val Leu Gly Arg
    50                  55                  60

Pro Gly Ala Gly Cys Thr Ser Phe Leu Lys Ser Ala Ala Gly Glu Thr
65                  70                  75                  80

Ser Gln Phe Ala Gly Gly Val Thr Thr Gly His Ile Ser Tyr Asp Gly
                85                  90                  95

Ile Pro Gln Lys Glu Met Met Gln His Tyr Lys Pro Asp Val Ile Tyr
            100                 105                 110

Asn Gly Glu Gln Asp Val His Phe Pro His Leu Thr Val Lys Gln Thr
        115                 120                 125

Leu Asp Phe Ala Ile Ser Cys Lys Met Pro Ala Lys Arg Val Asn Asn
    130                 135                 140

Val Thr Lys Glu Glu Tyr Ile Thr Ala Asn Arg Glu Phe Tyr Ala Lys
145                 150                 155                 160

Ile Phe Gly Leu Thr His Thr Phe Asp Thr Lys Val Gly Asn Asp Phe
                165                 170                 175

Ile Ser Gly Val Ser Gly Gly Glu Arg Lys Arg Val Ser Ile Ala Glu
```

```
            180             185             190
Ala Leu Ala Ala Lys Gly Ser Ile Tyr Cys Trp Asp Asn Ala Thr Arg
            195             200             205
Gly Leu Asp Ser Ser Thr Ala Leu Glu Phe Ala Arg Ala Ile Arg Thr
            210             215             220
Met Thr Asn Leu Leu Gly Thr Thr Ala Leu Val Thr Val Tyr Gln Ala
225             230             235             240
Ser Glu Asn Ile Tyr Glu Thr Phe Asp Lys Val Thr Val Leu Tyr Ala
                245             250             255
Gly Arg Gln Ile Phe Cys Gly Lys Thr Thr Glu Ala Lys Asp Tyr Phe
            260             265             270
Glu Asn Met Gly Tyr Leu Cys Pro Arg Gln Ser Thr Ala Glu Tyr
            275             280             285
Leu Thr Ala Ile Thr Asp Pro Asn Gly Leu His Glu Ile Lys Pro Gly
            290             295             300
Phe Glu Tyr Gln Val Pro His Thr Ala Asp Glu Phe Glu Lys Tyr Trp
305             310             315             320
Leu Asp Ser Pro Glu Tyr Ala Arg Leu Lys Gly Glu Ile Gln Lys Tyr
                325             330             335
Lys His Glu Val Asn Thr Glu Trp Thr Lys Lys Thr Tyr Asn Glu Ser
                340             345             350
Met Ala Gln Glu Lys Ser Lys Gly Thr Arg Lys Lys Ser Tyr Tyr Thr
            355             360             365
Val Ser Tyr Trp Glu Gln Ile Arg Leu Cys Thr Ile Arg Gly Phe Leu
            370             375             380
Arg Ile Tyr Gly Asp Lys Ser Tyr Thr Val Ile Asn Thr Cys Ala Ala
385             390             395             400
Ile Ala Gln Ala Phe Ile Thr Gly Ser Leu Phe Tyr Gln Ala Pro Ser
                405             410             415
Ser Thr Leu Gly Ala Phe Ser Arg Ser Gly Val Leu Phe Phe Ser Leu
            420             425             430
Leu Tyr Tyr Ser Leu Met Gly Leu Ala Asn Ile Ser Phe Glu His Arg
            435             440             445
Pro Ile Leu Gln Lys His Lys Val Tyr Ser Leu Tyr His Pro Ser Ala
            450             455             460
Glu Ala Leu Ala Ser Thr Ile Ser Ser Phe Pro Phe Arg Met Ile Gly
465             470             475             480
Leu Thr Phe Phe Ile Ile Ile Leu Tyr Phe Leu Ala Gly Leu His Arg
                485             490             495
Ser Ala Gly Ala Phe Phe Thr Met Tyr Leu Leu Leu Thr Met Cys Ser
            500             505             510
Glu Ala Ile Thr Ser Leu Phe Gln Met Val Ser Ser Leu Cys Asp Thr
            515             520             525
Leu Ser Gln Ala Asn Ser Ile Ala Gly Val Val Met Leu Ser Ile Ala
            530             535             540
Met Tyr Ser Thr Tyr Met Ile Gln Leu Pro Ser Met His Pro Trp Phe
545             550             555             560
Lys Trp Ile Ser Tyr Ile Leu Pro Ile Arg Tyr Ala Phe Glu Ser Met
                565             570             575
Leu Asn Ala Glu Phe His Gly Arg His Met Asp Cys Gly Gly Thr Leu
            580             585             590
Val Pro Ser Gly Pro Gly Phe Glu Asn Ile Leu Pro Glu Asn Gln Val
            595             600             605
```

-continued

Cys Ala Phe Val Gly Ser Arg Pro Gly Gln Ser Trp Val Leu Gly Asp
610             615                 620

Asp Tyr Leu Arg Ala Gln Tyr Gln Tyr Glu Tyr Lys Asn Thr Trp Arg
625             630                 635                 640

Asn Phe Gly Ile Met Trp Cys Phe Leu Ile Gly Tyr Ile Val Leu Arg
                645                 650                 655

Ala Val Phe Thr Glu Tyr Lys Ser Pro Val Lys Ser Gly Gly Asp Ala
            660                 665                 670

Leu Val Val Lys Lys Gly Thr Lys Asn Ala Ile Gln Arg Ser Trp Ser
            675                 680                 685

Ser Lys Asn Asp Glu Glu Asn Leu Asn Ala Ser Ile Ala Thr Gln Asp
690                 695                 700

Met Lys Glu Ile Ala Ser Ser Asn Asp Ser Thr Ser Ala Asp Phe
705             710                 715                 720

Glu Gly Leu Glu Ser Thr Gly Val Phe Ile Trp Lys Asn Val Ser Phe
                725                 730                 735

Thr Ile Pro His Ser Ser Gly Gln Arg Lys Leu Leu Asp Ser Val Ser
                740                 745                 750

Gly Tyr Cys Val Pro Gly Thr Leu Thr Ala Leu Ile Gly Glu Ser Gly
            755                 760                 765

Ala Gly Lys Thr Thr Leu Leu Asn Thr Leu Ala Gln Arg Asn Val Gly
770                 775                 780

Thr Ile Thr Gly Asp Met Leu Val Asp Gly Leu Pro Met Asp Ala Ser
785             790                 795                 800

Phe Lys Arg Arg Thr Gly Tyr Val Gln Gln Gln Asp Leu His Val Ala
                805                 810                 815

Glu Leu Thr Val Lys Glu Ser Leu Gln Phe Ser Ala Arg Met Arg Arg
            820                 825                 830

Pro Gln Ser Ile Pro Asp Ala Glu Lys Met Glu Tyr Val Glu Lys Ile
                835                 840                 845

Ile Ser Ile Leu Glu Met Gln Glu Phe Ser Glu Ala Leu Val Gly Glu
850                 855                 860

Ile Gly Tyr Gly Leu Asn Val Glu Gln Arg Lys Lys Leu Ser Ile Gly
865                 870                 875                 880

Val Glu Leu Val Gly Lys Pro Asp Leu Leu Leu Phe Leu Asp Glu Pro
                885                 890                 895

Thr Ser Gly Leu Asp Ser Gln Ser Ala Trp Ala Val Val Lys Met Leu
                900                 905                 910

Lys Arg Leu Ala Leu Ala Gly Gln Ser Ile Leu Cys Thr Ile His Gln
            915                 920                 925

Pro Ser Ala Thr Leu Phe Glu Gln Phe Asp Arg Leu Leu Leu Leu Gly
            930                 935                 940

Lys Gly Gly Gln Thr Ile Tyr Phe Gly Glu Ile Gly Lys Asn Ser Ser
945                 950                 955                 960

Ser Val Ile Lys Tyr Phe Glu Lys Asn Gly Ala Arg Lys Cys Gln Gln
                965                 970                 975

Asn Glu Asn Pro Ala Glu Tyr Ile Leu Glu Ala Ile Gly Ala Gly Ala
                980                 985                 990

Thr Ala Ser Val Gln Gln Asn Trp Pro Asp Ile Trp Gln Lys Ser His
            995                 1000                1005

Glu Tyr Ala Asn Ile Asn Glu Lys Ile Asn Asp Met Ile Lys Asp
    1010                1015                1020

-continued

```
Leu Ser Ser Thr Thr Leu His Lys Thr Ala Thr Arg Ala Ser Lys
    1025                1030                1035

Tyr Ala Thr Ser Tyr Ser Tyr Gln Phe His His Val Leu Lys Arg
    1040                1045                1050

Ser Ser Leu Thr Phe Trp Arg Asn Leu Asn Tyr Ile Met Ala Lys
    1055                1060                1065

Met Met Leu Leu Met Ile Ser Gly Leu Phe Ile Gly Phe Thr Phe
    1070                1075                1080

Phe His Val Gly Val Asn Ala Ile Gly Leu Gln Asn Ser Leu Phe
    1085                1090                1095

Ala Cys Phe Met Ala Ile Val Ile Ser Ala Pro Ala Thr Asn Gln
    1100                1105                1110

Ile Gln Glu Arg Ala Thr Val Ala Lys Glu Leu Tyr Glu Val Arg
    1115                1120                1125

Glu Ser Lys Ser Asn Met Phe His Trp Ser Leu Leu Leu Ile Thr
    1130                1135                1140

His Tyr Leu Asn Glu Leu Pro Tyr His Leu Leu Phe Ser Thr Ile
    1145                1150                1155

Phe Phe Val Ser Ser Tyr Phe Pro Leu Gly Val Phe Thr Glu Ala
    1160                1165                1170

Ser Arg Ser Ser Val Phe Tyr Leu Asn Tyr Ala Ile Leu Phe Gln
    1175                1180                1185

Leu Tyr Tyr Ile Gly Leu Ala Leu Met Ile Leu Tyr Met Ser Pro
    1190                1195                1200

Asn Leu Gln Ser Ala Asn Val Ile Val Gly Phe Ile Leu Ser Phe
    1205                1210                1215

Leu Leu Ser Phe Cys Gly Ala Val Gln Pro Ala Ser Leu Met Pro
    1220                1225                1230

Gly Phe Trp Thr Phe Met Trp Lys Leu Ser Pro Tyr Thr Tyr Phe
    1235                1240                1245

Leu Gln Asn Leu Val Gly Leu Leu Met His Asp Lys Pro Val Arg
    1250                1255                1260

Cys Ser Lys Lys Glu Leu Ser Leu Phe Asn Pro Val Gly Gln
    1265                1270                1275

Thr Cys Gly Glu Phe Thr Lys Pro Phe Glu Phe Gly Thr Gly
    1280                1285                1290

Tyr Ile Ala Asn Pro Asp Ala Thr Ala Asp Cys Ala Tyr Cys Gln
    1295                1300                1305

Tyr Lys Val Gly Asp Glu Tyr Leu Ala Arg Ile Asn Ala Ser Phe
    1310                1315                1320

Ser Tyr Leu Trp Arg Asn Phe Gly Phe Ile
    1325                1330

<210> SEQ ID NO 8
<211> LENGTH: 1049
<212> TYPE: PRT
<213> ORGANISM: Saccharomyces cerevisiae

<400> SEQUENCE: 8

Met Gly Ser His Arg Arg Tyr Leu Tyr Tyr Ser Ile Leu Ser Phe Leu
1               5                   10                  15

Leu Leu Ser Cys Ser Val Val Leu Ala Lys Gln Asp Lys Thr Pro Phe
            20                  25                  30

Phe Glu Gly Thr Ser Ser Lys Asn Ser Arg Leu Thr Ala Gln Asp Lys
        35                  40                  45
```

-continued

```
Gly Asn Asp Thr Cys Pro Pro Cys Phe Asn Cys Met Leu Pro Ile Phe
    50                  55                  60
Glu Cys Lys Gln Phe Ser Glu Cys Asn Ser Tyr Thr Gly Arg Cys Glu
65                  70                  75                  80
Cys Ile Glu Gly Phe Ala Gly Asp Asp Cys Ser Leu Pro Leu Cys Gly
                    85                  90                  95
Gly Leu Ser Pro Asp Glu Ser Gly Asn Lys Asp Arg Pro Ile Arg Ala
                100                 105                 110
Gln Asn Asp Thr Cys His Cys Asp Asn Gly Trp Gly Gly Ile Asn Cys
                115                 120                 125
Asp Val Cys Gln Glu Asp Phe Val Cys Asp Ala Phe Met Pro Asp Pro
130                 135                 140
Ser Ile Lys Gly Thr Cys Tyr Lys Asn Gly Met Ile Val Asp Lys Val
145                 150                 155                 160
Phe Ser Gly Cys Asn Val Thr Asn Glu Lys Ile Leu Gln Ile Leu Asn
                165                 170                 175
Gly Lys Ile Pro Gln Ile Thr Phe Ala Cys Asp Lys Pro Asn Gln Glu
                180                 185                 190
Cys Asn Phe Gln Phe Trp Ile Asp Gln Leu Glu Ser Phe Tyr Cys Gly
                195                 200                 205
Leu Ser Asp Cys Ala Phe Glu Tyr Asp Leu Glu Gln Asn Thr Ser His
    210                 215                 220
Tyr Lys Cys Asn Asp Val Gln Cys Lys Cys Val Pro Asp Thr Val Leu
225                 230                 235                 240
Cys Gly Ala Lys Gly Ser Ile Asp Ile Ser Asp Phe Leu Thr Glu Thr
                245                 250                 255
Ile Lys Gly Pro Gly Asp Phe Ser Cys Asp Leu Glu Thr Arg Gln Cys
                260                 265                 270
Lys Phe Ser Glu Pro Ser Met Asn Asp Leu Ile Leu Thr Val Phe Gly
    275                 280                 285
Asp Pro Tyr Ile Thr Leu Lys Cys Glu Ser Gly Glu Cys Val His Tyr
    290                 295                 300
Ser Glu Ile Pro Gly Tyr Lys Ser Pro Ser Lys Asp Pro Thr Val Ser
305                 310                 315                 320
Trp Gln Gly Lys Leu Val Leu Ala Leu Thr Ala Val Met Val Leu Ala
                325                 330                 335
Leu Phe Thr Phe Ala Thr Phe Tyr Ile Ser Lys Ser Pro Leu Phe Arg
                340                 345                 350
Asn Gly Leu Gly Ser Ser Lys Ser Pro Ile Arg Leu Pro Asp Glu Asp
                355                 360                 365
Ala Val Asn Asn Phe Leu Gln Asn Glu Asp Thr Leu Ala Thr Leu
                370                 375                 380
Ser Phe Glu Asn Ile Thr Tyr Ser Val Pro Ser Ile Asn Ser Asp Gly
385                 390                 395                 400
Val Glu Glu Thr Val Leu Asn Glu Ile Ser Gly Ile Val Lys Pro Gly
                405                 410                 415
Gln Ile Leu Ala Ile Met Gly Gly Ser Gly Ala Gly Lys Thr Thr Leu
                420                 425                 430
Leu Asp Ile Leu Ala Met Lys Arg Lys Thr Gly His Val Ser Gly Ser
                435                 440                 445
Ile Lys Val Asn Gly Ile Ser Met Asp Arg Lys Ser Phe Ser Lys Ile
    450                 455                 460
```

```
Ile Gly Phe Val Asp Gln Asp Asp Phe Leu Leu Pro Thr Leu Thr Val
465                 470                 475                 480

Phe Glu Thr Val Leu Asn Ser Ala Leu Leu Arg Leu Pro Lys Ala Leu
                485                 490                 495

Ser Phe Glu Ala Lys Lys Ala Arg Val Tyr Lys Val Leu Glu Glu Leu
            500                 505                 510

Arg Ile Ile Asp Ile Lys Asp Arg Ile Ile Gly Asn Glu Phe Asp Arg
        515                 520                 525

Gly Ile Ser Gly Gly Glu Lys Arg Arg Val Ser Ile Ala Cys Glu Leu
    530                 535                 540

Val Thr Ser Pro Leu Val Leu Phe Leu Asp Glu Pro Thr Ser Gly Leu
545                 550                 555                 560

Asp Ala Ser Asn Ala Asn Asn Val Ile Glu Cys Leu Val Arg Leu Ser
                565                 570                 575

Ser Asp Tyr Asn Arg Thr Leu Val Leu Ser Ile His Gln Pro Arg Ser
            580                 585                 590

Asn Ile Phe Tyr Leu Phe Asp Lys Leu Val Leu Ser Lys Gly Glu
        595                 600                 605

Met Val Tyr Ser Gly Asn Ala Lys Lys Val Ser Glu Phe Leu Arg Asn
610                 615                 620

Glu Gly Tyr Ile Cys Pro Asp Asn Tyr Asn Ile Ala Asp Tyr Leu Ile
625                 630                 635                 640

Asp Ile Thr Phe Glu Ala Gly Pro Gln Gly Lys Arg Arg Arg Ile Arg
                645                 650                 655

Asn Ile Ser Asp Leu Glu Ala Gly Thr Asp Thr Asn Asp Ile Asp Asn
            660                 665                 670

Thr Ile His Gln Thr Thr Phe Thr Ser Ser Asp Gly Thr Thr Gln Arg
        675                 680                 685

Glu Trp Ala His Leu Ala Ala His Arg Asp Glu Ile Arg Ser Leu Leu
    690                 695                 700

Arg Asp Glu Glu Asp Val Glu Gly Thr Asp Gly Arg Arg Gly Ala Thr
705                 710                 715                 720

Glu Ile Asp Leu Asn Thr Lys Leu Leu His Asp Lys Tyr Lys Asp Ser
                725                 730                 735

Val Tyr Tyr Ala Glu Leu Ser Gln Glu Ile Glu Glu Val Leu Ser Glu
            740                 745                 750

Gly Asp Glu Glu Ser Asn Val Leu Asn Gly Asp Leu Pro Thr Gly Gln
        755                 760                 765

Gln Ser Ala Gly Phe Leu Gln Gln Leu Ser Ile Leu Asn Ser Arg Ser
    770                 775                 780

Phe Lys Asn Met Tyr Arg Asn Pro Lys Leu Leu Leu Gly Asn Tyr Leu
785                 790                 795                 800

Leu Thr Ile Leu Leu Ser Leu Phe Leu Gly Thr Leu Tyr Tyr Asn Val
                805                 810                 815

Ser Asn Asp Ile Ser Gly Phe Gln Asn Arg Met Gly Leu Phe Phe
            820                 825                 830

Ile Leu Thr Tyr Phe Gly Phe Val Thr Phe Thr Gly Leu Ser Ser Phe
        835                 840                 845

Ala Leu Glu Arg Ile Ile Phe Ile Lys Glu Arg Ser Asn Asn Tyr Tyr
    850                 855                 860

Ser Pro Leu Ala Tyr Tyr Ile Ser Lys Ile Met Ser Glu Val Val Pro
865                 870                 875                 880

Leu Arg Val Val Pro Pro Ile Leu Leu Ser Leu Ile Val Tyr Pro Met
```

```
                885                 890                 895
Thr Gly Leu Asn Met Lys Asp Asn Ala Phe Phe Lys Cys Ile Gly Ile
            900                 905                 910

Leu Ile Leu Phe Asn Leu Gly Ile Ser Leu Glu Ile Leu Thr Ile Gly
        915                 920                 925

Ile Ile Phe Glu Asp Leu Asn Asn Ser Ile Ile Leu Ser Val Leu Val
    930                 935                 940

Leu Leu Gly Ser Leu Leu Phe Ser Gly Leu Phe Ile Asn Thr Lys Asn
945                 950                 955                 960

Ile Thr Asn Val Ala Phe Lys Tyr Leu Lys Asn Phe Ser Val Phe Tyr
            965                 970                 975

Tyr Ala Tyr Glu Ser Leu Leu Ile Asn Glu Val Lys Thr Leu Met Leu
        980                 985                 990

Lys Glu Arg Lys Tyr Gly Leu Asn Ile Glu Val Pro Gly Ala Thr Ile
    995                 1000                1005

Leu Ser Thr Phe Gly Phe Val Val Gln Asn Leu Val Phe Asp Ile
    1010                1015                1020

Lys Ile Leu Ala Leu Phe Asn Val Val Phe Leu Ile Met Gly Tyr
    1025                1030                1035

Leu Ala Leu Lys Trp Ile Val Val Glu Gln Lys
    1040                1045
```

<210> SEQ ID NO 9
<211> LENGTH: 1394
<212> TYPE: PRT
<213> ORGANISM: Saccharomyces cerevisiae

<400> SEQUENCE: 9

```
Met Ser Ile Ser Lys Tyr Phe Thr Pro Val Ala Asp Gly Ser Leu Thr
1               5                   10                  15

Phe Asn Gly Ala Asn Ile Gln Phe Gly Ala Asp Ala Gln Gly Glu Ser
            20                  25                  30

Lys Lys Ser Tyr Asp Ala Glu Asp Ser Met Pro Asn Pro Ala Asn Gln
        35                  40                  45

Leu Asn Asp Ile Thr Phe Gln Ala Glu Ala Gly Glu Met Val Leu Val
    50                  55                  60

Leu Gly Tyr Pro Thr Ser Thr Leu Phe Lys Thr Leu Phe His Gly Lys
65                  70                  75                  80

Thr Ser Leu Ser Tyr Ser Pro Pro Gly Ser Ile Lys Phe Lys Asn Asn
            85                  90                  95

Glu Phe Lys Ser Phe Ser Glu Lys Cys Pro His Gln Ile Ile Tyr Asn
            100                 105                 110

Asn Glu Gln Asp Val His Phe Pro Phe Leu Thr Val Glu Gln Thr Ile
        115                 120                 125

Asp Phe Ala Leu Ser Cys Lys Phe Asp Ile Pro Lys Gly Glu Arg Asp
    130                 135                 140

Gln Ile Arg Asn Glu Leu Leu Arg Glu Phe Gly Leu Ser His Val Leu
145                 150                 155                 160

Lys Thr Ile Val Gly Asn Asp Phe Phe Arg Gly Val Ser Gly Gly Glu
            165                 170                 175

Arg Lys Arg Ile Ser Ile Ile Glu Thr Phe Ile Ala Asn Gly Ser Val
            180                 185                 190

Tyr Leu Trp Asp Asn Ser Thr Lys Gly Leu Asp Ser Ala Thr Ala Leu
        195                 200                 205
```

-continued

```
Asp Phe Leu Glu Ile Leu Arg Lys Met Ala Lys Ala Thr Arg Ser Val
210                 215                 220
Asn Leu Val Arg Ile Ser Gln Ala Ser Asp Lys Ile Val Asp Lys Phe
225                 230                 235                 240
Asp Lys Ile Leu Met Leu Ser Asp Ser Tyr Gln Leu Phe Tyr Gly Thr
            245                 250                 255
Val Asp Glu Cys Leu Thr Tyr Phe Arg Asp Thr Leu Gly Ile Glu Lys
        260                 265                 270
Asp Pro Asn Asp Cys Ile Ile Glu Tyr Leu Thr Ser Ile Leu Asn Phe
            275                 280                 285
Gln Phe Lys Asn Lys Asn Leu Gly Asn Leu Ser Asn Ser Ser Ser Ala
290                 295                 300
Ser Val Leu Lys Thr Ala Thr Gly Glu Val Thr Lys Tyr Thr Tyr Asn
305                 310                 315                 320
Ser Asp Phe Asp Leu Tyr Asp Gln Trp Lys His Ser Ser Tyr Tyr Arg
            325                 330                 335
Asn Ile Lys Gln Gln Ile Gln Gly Ser Ser Ile Asp Asp Ser Ile Lys
            340                 345                 350
Glu Val Asp Pro Ser Asp Val Ser Pro Ile Phe Asn Ile Pro Leu Lys
        355                 360                 365
Lys Gln Leu Leu Phe Cys Thr Lys Arg Ala Phe Gln Arg Ser Leu Gly
370                 375                 380
Asp Lys Ala Tyr Met Thr Ala Gln Phe Ile Ser Val Val Ile Gln Ser
385                 390                 395                 400
Leu Val Ile Gly Ser Leu Phe Tyr Glu Ile Pro Leu Thr Thr Ile Gly
            405                 410                 415
Ser Tyr Ser Arg Gly Ser Leu Thr Phe Phe Ser Ile Leu Phe Phe Thr
        420                 425                 430
Phe Leu Ser Leu Ala Asp Met Pro Ile Ala Phe Gln Arg Gln Pro Val
            435                 440                 445
Val Lys Lys Gln Ser Gln Leu His Phe Tyr Thr Asn Trp Val Glu Thr
        450                 455                 460
Leu Ser Thr Thr Val Phe Asp Tyr Cys Phe Lys Leu Cys Leu Val Ile
465                 470                 475                 480
Val Phe Ser Ile Ile Leu Tyr Phe Leu Ala His Leu Gln Tyr Lys Ala
            485                 490                 495
Ala Arg Phe Phe Ile Phe Leu Leu Phe Leu Ser Phe Tyr Asn Phe Cys
            500                 505                 510
Met Val Ser Leu Phe Ala Leu Thr Thr Leu Val Ala Pro Thr Ile Ser
        515                 520                 525
Val Ala Asn Leu Phe Ala Gly Ile Leu Leu Ala Ile Ala Met Tyr
        530                 535                 540
Ala Ser Tyr Val Ile Tyr Leu Lys Asn Met His Pro Trp Phe Val Trp
545                 550                 555                 560
Ile Ala Tyr Leu Asn Pro Ala Met Tyr Ala Met Glu Ala Ile Leu Ser
            565                 570                 575
Asn Glu Leu Tyr Asn Leu Lys Leu Asp Cys Ser Glu Thr Ile Val Pro
            580                 585                 590
Arg Gly Pro Thr Tyr Asn Asp Val Pro Phe Ser His Lys Ala Cys Ala
            595                 600                 605
Trp Gln Gly Ala Thr Leu Gly Asn Asp Tyr Val Arg Gly Arg Asp Tyr
610                 615                 620
Leu Lys Gln Gly Leu Ser Tyr Thr Tyr His His Val Trp Arg Asn Phe
```

-continued

```
            625                 630                 635                 640
        Gly Ile Ile Ile Gly Phe Leu Val Phe Phe Ile Ala Cys Thr Leu Phe
                            645                 650                 655

Ala Ser Gln Tyr Ile Lys Pro Tyr Phe Asn Lys Asp Glu Ile Glu Arg
                        660                 665                 670

Asn Asn Ser Arg Leu Thr Arg Trp Leu Pro Phe Leu Asn Lys Lys Arg
                    675                 680                 685

Gly Thr Arg Ser Ser Ala Arg Asn Asp Ser Lys Tyr Val Gly Ile Pro
                690                 695                 700

Lys Ser His Ser Val Ser Ser Ser Ser Ser Leu Ser Ala Val Pro
        705                 710                 715                 720

Tyr Gln Ile Ser Pro Ser Asn Lys Glu Met Ala Leu Asn Asp Tyr Asn
                            725                 730                 735

Glu Gln Pro Ile Thr Glu Thr Val Glu Thr Gln Lys His Ile Ile Ser
                        740                 745                 750

Trp Lys Asn Ile Asn Tyr Thr Val Gly Thr Lys Lys Leu Ile Asn Asn
                    755                 760                 765

Ala Ser Gly Phe Ile Ser Ser Gly Leu Thr Ala Leu Met Gly Glu Ser
                770                 775                 780

Gly Ala Gly Lys Thr Thr Leu Leu Asn Val Leu Ser Gln Arg Val Glu
        785                 790                 795                 800

Thr Gly Val Val Ser Gly Glu Ile Leu Ile Asp Gly His Pro Leu Thr
                            805                 810                 815

Asp Glu Asp Ala Phe Lys Arg Ser Ile Gly Phe Val Gln Gln Gln Asp
                        820                 825                 830

Leu His Leu Asp Leu Leu Ser Val Lys Glu Ser Leu Glu Ile Ser Cys
                    835                 840                 845

Leu Leu Arg Gly Asp Gly Asp Arg Ala Tyr Leu Asp Thr Val Ser Asn
                850                 855                 860

Leu Leu Lys Leu Pro Ser Asp Ile Leu Ala Asp Leu Asn Pro Thr
        865                 870                 875                 880

Gln Arg Lys Leu Leu Ser Ile Gly Val Glu Leu Val Thr Lys Pro Ser
                            885                 890                 895

Leu Leu Leu Phe Leu Asp Glu Pro Thr Ser Gly Leu Asp Ala Glu Ala
                        900                 905                 910

Ala Leu Thr Ile Val Lys Phe Leu Lys Gln Leu Ser Leu Gln Gly Gln
                    915                 920                 925

Ala Ile Phe Cys Thr Ile His Gln Pro Ser Lys Ser Val Ile Ser His
                930                 935                 940

Phe Asp Asn Ile Phe Leu Leu Lys Arg Gly Gly Glu Cys Val Phe Phe
        945                 950                 955                 960

Gly Pro Met Asp Asp Ala Cys Gly Tyr Phe Met Ser His Asp Asn Thr
                            965                 970                 975

Leu Val Tyr Asp Lys Glu His Asp Asn Pro Ala Asp Phe Val Ile Asp
                        980                 985                 990

Ala Val Gly Asn Ser Asn Ser Ser Ala Gly Lys Asp Thr Ala Glu Glu
                    995                 1000                1005

Ala Leu Thr Leu Asn Lys Glu Ala Ile Asp Trp Ser Ala Leu Trp
                1010                1015                1020

Glu Ser Ser Val Glu Lys Lys Leu Val Lys Lys Glu Thr Ala Arg
            1025                1030                1035

Leu Glu Asp Asp Ala Arg Ala Ser Gly Val Asp Tyr Thr Thr Ser
            1040                1045                1050
```

Leu Trp Lys Gln Pro Ser Tyr Leu Gln Gln Leu Ala Leu Ile Thr
    1055                1060                1065

Arg Arg Gln Tyr Ile Cys Thr Lys Arg Asp Met Thr Tyr Val Met
    1070                1075                1080

Ala Lys Tyr Cys Leu Asn Gly Gly Ala Gly Leu Phe Ile Gly Phe
    1085                1090                1095

Ser Phe Trp His Ile Lys His Asn Ile Ile Gly Leu Gln Asp Ser
    1100                1105                1110

Ile Phe Phe Cys Phe Met Ala Leu Cys Val Ser Ser Pro Leu Ile
    1115                1120                1125

Asn Gln Ile Gln Asp Lys Ala Leu Lys Thr Lys Glu Val Tyr Val
    1130                1135                1140

Ala Arg Glu Ala Arg Ser Asn Thr Tyr His Trp Thr Val Leu Leu
    1145                1150                1155

Leu Ser Gln Ser Ile Ile Glu Leu Pro Leu Ala Leu Thr Ser Ser
    1160                1165                1170

Thr Leu Phe Phe Val Cys Ala Phe Phe Ser Cys Gly Phe Asn Asn
    1175                1180                1185

Ala Gly Trp Ser Ala Gly Val Phe Phe Leu Asn Tyr Met Leu Phe
    1190                1195                1200

Ala Ala Tyr Tyr Ser Thr Leu Gly Leu Trp Leu Ile Tyr Thr Ala
    1205                1210                1215

Pro Asn Leu Gln Thr Ala Ala Val Phe Val Ala Phe Ile Tyr Ser
    1220                1225                1230

Phe Thr Ala Ser Phe Cys Gly Val Met Gln Pro Tyr Ser Leu Phe
    1235                1240                1245

Pro Thr Phe Trp Lys Phe Met Tyr Arg Val Ser Pro Tyr Thr Tyr
    1250                1255                1260

Phe Val Glu Thr Phe Val Ser Ile Leu Leu His Asn Trp Glu Ile
    1265                1270                1275

Lys Cys Asp Met Ser Glu Met Val Pro Gly Gln Pro Leu Thr Gly
    1280                1285                1290

Gln Ser Cys Gly Gln Phe Met Glu Ala Phe Ile Glu Glu Tyr Gly
    1295                1300                1305

Gly Tyr Leu His Asn Lys Asn Thr Phe Thr Val Cys Ala Tyr Cys
    1310                1315                1320

Thr Tyr Thr Val Gly Asp Asp Phe Leu Lys Asn Glu Asn Met Ser
    1325                1330                1335

Tyr Asp His Val Trp Arg Asn Phe Gly Ile Glu Trp Ala Phe Val
    1340                1345                1350

Gly Phe Asn Phe Phe Ala Met Phe Ala Gly Tyr Tyr Leu Thr Tyr
    1355                1360                1365

Val Ala Arg Ile Trp Pro Lys Val Phe Lys Ile Thr Lys Val
    1370                1375                1380

Ile Pro His Arg Gly Lys Lys Pro Val Gln Asn
    1385                1390

<210> SEQ ID NO 10
<211> LENGTH: 1290
<212> TYPE: PRT
<213> ORGANISM: Saccharomyces cerevisiae

<400> SEQUENCE: 10

Met Asn Phe Leu Ser Phe Lys Thr Thr Lys His Tyr His Ile Phe Arg

-continued

```
1               5                   10                  15
Tyr Val Asn Ile Arg Asn Asp Tyr Arg Leu Met Ile Met Ile Ile
            20                  25                  30
Gly Thr Val Ala Thr Gly Leu Val Pro Ala Ile Thr Ser Ile Leu Thr
            35                  40                  45
Gly Arg Val Phe Asp Leu Leu Ser Val Phe Val Ala Asn Gly Ser His
            50                  55                  60
Gln Gly Leu Tyr Ser Gln Leu Val Gln Arg Ser Met Ala Val Met Ala
65                  70                  75                  80
Leu Gly Ala Ala Ser Val Pro Val Met Trp Leu Ser Leu Thr Ser Trp
                85                  90                  95
Met His Ile Gly Glu Arg Gln Gly Phe Arg Ile Arg Ser Gln Ile Leu
                100                 105                 110
Glu Ala Tyr Leu Glu Glu Lys Pro Met Glu Trp Tyr Asp Asn Asn Glu
                115                 120                 125
Lys Leu Leu Gly Asp Phe Thr Gln Ile Asn Arg Cys Val Glu Glu Leu
            130                 135                 140
Arg Ser Ser Ser Ala Glu Ala Ser Ala Ile Thr Phe Gln Asn Leu Val
145                 150                 155                 160
Ala Ile Cys Ala Leu Leu Gly Thr Ser Phe Tyr Tyr Ser Trp Ser Leu
                165                 170                 175
Thr Leu Ile Ile Leu Cys Ser Ser Pro Ile Ile Thr Phe Phe Ala Val
                180                 185                 190
Val Phe Ser Arg Met Ile His Val Tyr Ser Glu Lys Glu Asn Ser Glu
                195                 200                 205
Thr Ser Lys Ala Ala Gln Leu Leu Thr Trp Ser Met Asn Ala Ala Gln
            210                 215                 220
Leu Val Arg Leu Tyr Cys Thr Gln Arg Leu Glu Arg Lys Lys Phe Lys
225                 230                 235                 240
Glu Ile Ile Leu Asn Cys Asn Thr Phe Phe Ile Lys Ser Cys Phe Phe
                245                 250                 255
Val Ala Ala Asn Ala Gly Ile Leu Arg Phe Leu Thr Leu Thr Met Phe
                260                 265                 270
Val Gln Gly Phe Trp Phe Gly Ser Ala Met Ile Lys Lys Gly Lys Leu
                275                 280                 285
Asn Ile Asn Asp Val Ile Thr Cys Phe His Ser Cys Ile Met Leu Gly
            290                 295                 300
Ser Thr Leu Asn Asn Thr Leu His Gln Ile Val Val Leu Gln Lys Gly
305                 310                 315                 320
Gly Val Ala Met Glu Lys Ile Met Thr Leu Leu Lys Asp Gly Ser Lys
                325                 330                 335
Arg Asn Pro Leu Asn Lys Thr Val Ala His Gln Phe Pro Leu Asp Tyr
            340                 345                 350
Ala Thr Ser Asp Leu Thr Phe Ala Asn Val Ser Phe Ser Tyr Pro Ser
            355                 360                 365
Arg Pro Ser Glu Ala Val Leu Lys Asn Val Ser Leu Asn Phe Ser Ala
            370                 375                 380
Gly Gln Phe Thr Phe Ile Val Gly Lys Ser Gly Ser Gly Lys Ser Thr
385                 390                 395                 400
Leu Ser Asn Leu Leu Leu Arg Phe Tyr Asp Gly Tyr Asn Gly Ser Ile
                405                 410                 415
Ser Ile Asn Gly His Asn Ile Gln Thr Ile Asp Gln Lys Leu Leu Ile
            420                 425                 430
```

```
Glu Asn Ile Thr Val Val Glu Gln Arg Cys Thr Leu Phe Asn Asp Thr
            435                 440                 445

Leu Arg Lys Asn Ile Leu Leu Gly Ser Thr Asp Ser Val Arg Asn Ala
            450                 455                 460

Asp Cys Ser Thr Asn Glu Asn Arg His Leu Ile Lys Asp Ala Cys Gln
465                 470                 475                 480

Met Ala Leu Leu Asp Arg Phe Ile Leu Asp Leu Pro Asp Gly Leu Glu
                    485                 490                 495

Thr Leu Ile Gly Thr Gly Gly Val Thr Leu Ser Gly Gly Gln Gln Gln
                500                 505                 510

Arg Val Ala Ile Ala Arg Ala Phe Ile Arg Asp Thr Pro Ile Leu Phe
                515                 520                 525

Leu Asp Glu Ala Val Ser Ala Leu Asp Ile Val His Arg Asn Leu Leu
            530                 535                 540

Met Lys Ala Ile Arg His Trp Arg Lys Gly Lys Thr Thr Ile Ile Leu
545                 550                 555                 560

Thr His Glu Leu Ser Gln Ile Glu Ser Asp Asp Tyr Leu Tyr Leu Met
                565                 570                 575

Lys Glu Gly Glu Val Val Glu Ser Gly Thr Gln Ser Glu Leu Leu Ala
                580                 585                 590

Asp Pro Thr Thr Thr Phe Ser Thr Trp Tyr His Leu Gln Asn Asp Tyr
            595                 600                 605

Ser Asp Ala Lys Thr Ile Val Asp Thr Glu Thr Glu Glu Lys Ser Ile
            610                 615                 620

His Thr Val Glu Ser Phe Asn Ser Gln Leu Glu Thr Pro Lys Leu Gly
625                 630                 635                 640

Ser Cys Leu Ser Asn Leu Gly Tyr Asp Glu Thr Asp Gln Leu Ser Phe
                    645                 650                 655

Tyr Glu Ala Ile Tyr Gln Lys Arg Ser Asn Val Arg Thr Arg Arg Val
                660                 665                 670

Lys Val Glu Glu Glu Asn Ile Gly Tyr Ala Leu Lys Gln Gln Lys Asn
            675                 680                 685

Thr Glu Ser Ser Thr Gly Pro Gln Leu Leu Ser Ile Ile Gln Ile Ile
            690                 695                 700

Lys Arg Met Ile Lys Ser Ile Arg Tyr Lys Lys Ile Leu Ile Leu Gly
705                 710                 715                 720

Leu Leu Cys Ser Leu Ile Ala Gly Ala Thr Asn Pro Val Phe Ser Tyr
                725                 730                 735

Thr Phe Ser Phe Leu Leu Glu Gly Ile Val Pro Ser Thr Asp Gly Lys
                740                 745                 750

Thr Gly Ser Ser His Tyr Leu Ala Lys Trp Ser Leu Leu Val Leu Gly
                755                 760                 765

Val Ala Ala Ala Asp Gly Ile Phe Asn Phe Ala Lys Gly Phe Leu Leu
                770                 775                 780

Asp Cys Cys Ser Glu Tyr Trp Val Met Asp Leu Arg Asn Glu Val Met
785                 790                 795                 800

Glu Lys Leu Thr Arg Lys Asn Met Asp Trp Phe Ser Gly Glu Asn Asn
                    805                 810                 815

Lys Ala Ser Glu Ile Ser Ala Leu Val Leu Asn Asp Leu Arg Asp Leu
                820                 825                 830

Arg Ser Leu Val Ser Glu Phe Leu Ser Ala Met Thr Ser Phe Val Thr
                835                 840                 845
```

```
Val Ser Thr Ile Gly Leu Ile Trp Ala Leu Val Ser Gly Trp Lys Leu
        850                 855                 860

Ser Leu Val Cys Ile Ser Met Phe Pro Leu Ile Ile Phe Ser Ala
865                 870                 875                 880

Ile Tyr Gly Gly Ile Leu Gln Lys Cys Glu Thr Asp Tyr Lys Thr Ser
                    885                 890                 895

Val Ala Gln Leu Glu Asn Cys Leu Tyr Gln Ile Val Thr Asn Ile Lys
            900                 905                 910

Thr Ile Lys Cys Leu Gln Ala Glu Phe His Phe Gln Leu Thr Tyr His
        915                 920                 925

Asp Leu Lys Ile Lys Met Gln Gln Ile Ala Ser Lys Arg Ala Ile Ala
        930                 935                 940

Thr Gly Phe Gly Ile Ser Met Thr Asn Met Ile Val Met Cys Ile Gln
945                 950                 955                 960

Ala Ile Ile Tyr Tyr Tyr Gly Leu Lys Leu Val Met Ile His Glu Tyr
                965                 970                 975

Thr Ser Lys Glu Met Phe Thr Thr Phe Thr Leu Leu Leu Phe Thr Ile
            980                 985                 990

Met Ser Cys Thr Ser Leu Val Ser  Gln Ile Pro Asp Ile  Ser Arg Gly
            995                 1000                1005

Gln Arg  Ala Ala Ser Trp Ile  Tyr Arg Ile Leu Asp  Glu Lys His
    1010                1015                 1020

Asn Thr  Leu Glu Val Glu Asn  Asn Ala Arg Thr  Val Gly Ile
    1025                1030                 1035

Ala Gly  His Thr Tyr His Gly  Lys Glu Lys Lys Pro  Ile Val Ser
    1040                1045                 1050

Ile Gln  Asn Leu Thr Phe Ala  Tyr Pro Ser Ala Pro  Thr Ala Phe
    1055                1060                 1065

Val Tyr  Lys Asn Met Asn Phe  Asp Met Phe Cys Gly  Gln Thr Leu
    1070                1075                 1080

Gly Ile  Ile Gly Glu Ser Gly  Thr Gly Lys Ser Thr  Leu Val Leu
    1085                1090                 1095

Leu Leu  Thr Lys Leu Tyr Asn  Cys Glu Val Gly Lys  Ile Lys Ile
    1100                1105                 1110

Asp Gly  Thr Asp Val Asn Asp  Trp Asn Leu Thr Ser  Leu Arg Lys
    1115                1120                 1125

Glu Ile  Ser Val Val Glu Gln  Lys Pro Leu Leu Phe  Asn Gly Thr
    1130                1135                 1140

Ile Arg  Asp Asn Leu Thr Tyr  Gly Leu Gln Asp Glu  Ile Leu Glu
    1145                1150                 1155

Ile Glu  Met Tyr Asp Ala Leu  Lys Tyr Val Gly Ile  His Asp Phe
    1160                1165                 1170

Val Ile  Ser Ser Pro Gln Gly  Leu Asp Thr Arg Ile  Asp Thr Thr
    1175                1180                 1185

Leu Leu  Ser Gly Gly Gln Ala  Gln Arg Leu Cys Ile  Ala Arg Ala
    1190                1195                 1200

Leu Leu  Arg Lys Ser Lys Ile  Leu Ile Leu Asp Glu  Cys Thr Ser
    1205                1210                 1215

Ala Leu  Asp Ser Val Ser Ser  Ser Ile Ile Asn Glu  Ile Val Lys
    1220                1225                 1230

Lys Gly  Pro Pro Ala Leu Leu  Thr Met Val Ile Thr  His Ser Glu
    1235                1240                 1245

Gln Met  Met Arg Ser Cys Asn  Ser Ile Ala Val Leu  Lys Asp Gly
```

```
                    1250                1255                1260
Lys Val Val Glu Arg Gly Asn Phe Asp Thr Leu Tyr Asn Asn Arg
            1265                1270                1275

Gly Glu Leu Phe Gln Ile Val Ser Asn Gln Ser Ser
            1280                1285                1290

<210> SEQ ID NO 11
<211> LENGTH: 1294
<212> TYPE: PRT
<213> ORGANISM: Saccharomyces cerevisiae

<400> SEQUENCE: 11

Met Ser Gln Gln Glu Asn Gly Asp Val Ala Thr Glu Leu Ile Glu Asn
1               5                   10                  15

Arg Leu Ser Phe Ser Arg Ile Pro Arg Ile Ser Leu His Val Arg Asp
                20                  25                  30

Leu Ser Ile Val Ala Ser Lys Thr Asn Thr Thr Leu Val Asn Thr Phe
            35                  40                  45

Ser Met Asp Leu Pro Ser Gly Ser Val Met Ala Val Met Gly Gly Ser
    50                  55                  60

Gly Ser Gly Lys Thr Thr Leu Leu Asn Val Leu Ala Ser Lys Ile Ser
65                  70                  75                  80

Gly Gly Leu Thr His Asn Gly Ser Ile Arg Tyr Val Leu Glu Asp Thr
                85                  90                  95

Gly Ser Glu Pro Asn Glu Thr Glu Pro Lys Arg Ala His Leu Asp Gly
            100                 105                 110

Gln Asp His Pro Ile Gln Lys His Val Ile Met Ala Tyr Leu Pro Gln
            115                 120                 125

Gln Asp Val Leu Ser Pro Arg Leu Thr Cys Arg Glu Thr Leu Lys Phe
    130                 135                 140

Ala Ala Asp Leu Lys Leu Asn Ser Ser Glu Arg Thr Lys Lys Leu Met
145                 150                 155                 160

Val Glu Gln Leu Ile Glu Glu Leu Gly Leu Lys Asp Cys Ala Asp Thr
                165                 170                 175

Leu Val Gly Asp Asn Ser His Arg Gly Leu Ser Gly Gly Glu Lys Arg
            180                 185                 190

Arg Leu Ser Ile Gly Thr Gln Met Ile Ser Asn Pro Ser Ile Met Phe
            195                 200                 205

Leu Asp Glu Pro Thr Thr Gly Leu Asp Ala Tyr Ser Ala Phe Leu Val
    210                 215                 220

Ile Lys Thr Leu Lys Lys Leu Ala Lys Glu Asp Gly Arg Thr Phe Ile
225                 230                 235                 240

Met Ser Ile His Gln Pro Arg Ser Asp Ile Leu Phe Leu Leu Asp Gln
                245                 250                 255

Val Cys Ile Leu Ser Lys Gly Asn Val Val Tyr Cys Asp Lys Met Asp
            260                 265                 270

Asn Thr Ile Pro Tyr Phe Glu Ser Ile Gly Tyr His Val Pro Gln Leu
            275                 280                 285

Val Asn Pro Ala Asp Tyr Phe Ile Asp Leu Ser Ser Val Asp Ser Arg
    290                 295                 300

Ser Asp Lys Glu Glu Ala Ala Thr Gln Ser Arg Leu Asn Ser Leu Ile
305                 310                 315                 320

Asp His Trp His Asp Tyr Glu Arg Thr His Leu Gln Leu Gln Ala Glu
                325                 330                 335
```

```
Ser Tyr Ile Ser Asn Ala Thr Glu Ile Gln Ile Gln Asn Met Thr Thr
            340                 345                 350

Arg Leu Pro Phe Trp Lys Gln Val Thr Val Leu Thr Arg Arg Asn Phe
        355                 360                 365

Lys Leu Asn Phe Ser Asp Tyr Val Thr Leu Ile Ser Thr Phe Ala Glu
        370                 375                 380

Pro Leu Ile Ile Gly Thr Val Cys Gly Trp Ile Tyr Tyr Lys Pro Asp
385                 390                 395                 400

Lys Ser Ser Ile Gly Gly Leu Arg Thr Thr Ala Cys Leu Tyr Ala
                405                 410                 415

Ser Thr Ile Leu Gln Cys Tyr Leu Tyr Leu Leu Phe Asp Thr Tyr Arg
            420                 425                 430

Leu Cys Glu Gln Asp Ile Ala Leu Tyr Asp Arg Glu Arg Ala Glu Gly
            435                 440                 445

Ser Val Thr Pro Leu Ala Phe Ile Val Ala Arg Lys Ile Ser Leu Phe
            450                 455                 460

Leu Ser Asp Asp Phe Ala Met Thr Met Ile Phe Val Ser Ile Thr Tyr
465                 470                 475                 480

Phe Met Phe Gly Leu Glu Ala Asp Ala Arg Lys Phe Phe Tyr Gln Phe
                485                 490                 495

Ala Val Val Phe Leu Cys Gln Leu Ser Cys Ser Gly Leu Ser Met Leu
            500                 505                 510

Ser Val Ala Val Ser Arg Asp Phe Ser Lys Ala Ser Leu Val Gly Asn
            515                 520                 525

Met Thr Phe Thr Val Leu Ser Met Gly Cys Gly Phe Phe Val Asn Ala
530                 535                 540

Lys Val Met Pro Val Tyr Val Arg Trp Ile Lys Tyr Ile Ala Phe Thr
545                 550                 555                 560

Trp Tyr Ser Phe Gly Thr Leu Met Ser Thr Phe Thr Asn Ser Tyr
                565                 570                 575

Cys Thr Thr Asp Asn Leu Asp Glu Cys Leu Gly Asn Gln Ile Leu Glu
            580                 585                 590

Val Tyr Gly Phe Pro Arg Asn Trp Ile Thr Val Pro Ala Val Val Leu
            595                 600                 605

Leu Cys Trp Ser Val Gly Tyr Phe Val Val Gly Ala Ile Ile Leu Tyr
610                 615                 620

Leu His Lys Ile Asp Ile Thr Leu Gln Asn Glu Val Lys Ser Lys Gln
625                 630                 635                 640

Lys Lys Ile Lys Lys Ser Pro Thr Gly Met Lys Pro Glu Ile Gln
                645                 650                 655

Leu Leu Asp Asp Val Tyr His Gln Lys Asp Leu Glu Ala Glu Lys Gly
            660                 665                 670

Lys Asn Ile His Ile Thr Ile Lys Leu Glu Asp Ile Asp Leu Arg Val
            675                 680                 685

Ile Phe Ser Ala Pro Phe Ser Asn Trp Lys Gly Asn Phe His His
690                 695                 700

Glu Thr Lys Glu Ile Leu Gln Ser Val Asn Ala Ile Phe Lys Pro Gly
705                 710                 715                 720

Met Ile Asn Ala Ile Met Gly Pro Ser Gly Ser Gly Lys Ser Ser Leu
                725                 730                 735

Leu Asn Leu Ile Ser Gly Arg Leu Lys Ser Ser Val Phe Ala Lys Phe
            740                 745                 750

Asp Thr Ser Gly Ser Ile Met Phe Asn Asp Ile Gln Val Ser Glu Leu
```

```
                755              760              765
Met Phe Lys Asn Val Cys Ser Tyr Val Ser Gln Asp Asp His Leu
770              775              780

Leu Ala Ala Leu Thr Val Lys Glu Thr Leu Lys Tyr Ala Ala Ala Leu
785              790              795              800

Arg Leu His His Leu Thr Glu Ala Glu Arg Met Glu Arg Thr Asp Asn
                805              810              815

Leu Ile Arg Ser Leu Gly Leu Lys His Cys Glu Asn Asn Ile Ile Gly
            820              825              830

Asn Glu Phe Val Lys Gly Ile Ser Gly Gly Glu Lys Arg Arg Val Thr
            835              840              845

Met Gly Val Gln Leu Leu Asn Asp Pro Pro Ile Leu Leu Leu Asp Glu
850              855              860

Pro Thr Ser Gly Leu Asp Ser Phe Thr Ser Ala Thr Ile Leu Glu Ile
865              870              875              880

Leu Glu Lys Leu Cys Arg Glu Gln Gly Lys Thr Ile Ile Ile Thr Ile
                885              890              895

His Gln Pro Arg Ser Glu Leu Phe Lys Arg Phe Gly Asn Val Leu Leu
            900              905              910

Leu Ala Lys Ser Gly Arg Thr Ala Phe Asn Gly Ser Pro Asp Glu Met
            915              920              925

Ile Ala Tyr Phe Thr Glu Leu Gly Tyr Asn Cys Pro Ser Phe Thr Asn
930              935              940

Val Ala Asp Phe Phe Leu Asp Leu Ile Ser Val Asn Thr Gln Asn Glu
945              950              955              960

Gln Asn Glu Ile Ser Ser Arg Ala Arg Val Glu Lys Ile Leu Ser Ala
            965              970              975

Trp Lys Ala Asn Met Asp Asn Glu Ser Leu Ser Pro Thr Pro Ile Ser
            980              985              990

Glu Lys Gln Gln Tyr Ser Gln Glu Ser Phe Phe Thr Glu Tyr Ser Glu
            995              1000             1005

Phe Val Arg Lys Pro Ala Asn Leu Val Leu Ala Tyr Ile Val Asn
    1010             1015             1020

Val Lys Arg Gln Phe Thr Thr Thr Arg Arg Ser Phe Asp Ser Leu
    1025             1030             1035

Met Ala Arg Ile Ala Gln Ile Pro Gly Leu Gly Val Ile Phe Ala
    1040             1045             1050

Leu Phe Phe Ala Pro Val Lys His Asn Tyr Thr Ser Ile Ser Asn
    1055             1060             1065

Arg Leu Gly Leu Ala Gln Glu Ser Thr Ala Leu Tyr Phe Val Gly
    1070             1075             1080

Met Leu Gly Asn Leu Ala Cys Tyr Pro Thr Glu Arg Asp Tyr Phe
    1085             1090             1095

Tyr Glu Glu Tyr Asn Asp Asn Val Tyr Gly Ile Ala Pro Phe Phe
    1100             1105             1110

Leu Ala Tyr Met Thr Leu Glu Leu Pro Leu Ser Ala Leu Ala Ser
    1115             1120             1125

Val Leu Tyr Ala Val Phe Thr Val Leu Ala Cys Gly Leu Pro Arg
    1130             1135             1140

Thr Ala Gly Asn Phe Phe Ala Thr Val Tyr Cys Ser Phe Ile Val
    1145             1150             1155

Thr Cys Cys Gly Glu Ala Leu Gly Ile Met Thr Asn Thr Phe Phe
    1160             1165             1170
```

```
Glu Arg Pro Gly Phe Val Val Asn Cys Ile Ser Ile Ile Leu Ser
    1175            1180                1185

Ile Gly Thr Gln Met Ser Gly Leu Met Ser Leu Gly Met Ser Arg
    1190            1195                1200

Val Leu Lys Gly Phe Asn Tyr Leu Asn Pro Val Gly Tyr Thr Ser
    1205            1210                1215

Met Ile Ile Ile Asn Phe Ala Phe Pro Gly Asn Leu Lys Leu Thr
    1220            1225                1230

Cys Glu Asp Gly Gly Lys Asn Ser Asp Gly Thr Cys Glu Phe Ala
    1235            1240                1245

Asn Gly His Asp Val Leu Val Ser Tyr Gly Leu Val Arg Asn Thr
    1250            1255                1260

Gln Lys Tyr Leu Gly Ile Ile Val Cys Val Ala Ile Ile Tyr Arg
    1265            1270                1275

Leu Ile Ala Phe Phe Ile Leu Lys Ala Lys Leu Glu Trp Ile Lys
    1280            1285                1290

Trp

<210> SEQ ID NO 12
<211> LENGTH: 1477
<212> TYPE: PRT
<213> ORGANISM: Saccharomyces cerevisiae

<400> SEQUENCE: 12

Met Thr Ile Thr Val Gly Asp Ala Val Ser Glu Thr Glu Leu Glu Asn
1               5                   10                  15

Lys Ser Gln Asn Val Val Leu Ser Pro Lys Ala Ser Ala Ser Ser Asp
                20                  25                  30

Ile Ser Thr Asp Val Asp Lys Asp Thr Ser Ser Ser Trp Asp Asp Lys
                35                  40                  45

Ser Leu Leu Pro Thr Gly Glu Tyr Ile Val Asp Arg Asn Lys Pro Gln
        50                  55                      60

Thr Tyr Leu Asn Ser Asp Asp Ile Glu Lys Val Thr Glu Ser Asp Ile
65              70                  75                      80

Phe Pro Gln Lys Arg Leu Phe Ser Phe Leu His Ser Lys Lys Ile Pro
                85                  90                  95

Glu Val Pro Gln Thr Asp Asp Gly Arg Lys Ile Tyr Pro Leu Phe His
                100                 105                 110

Thr Asn Ile Ile Ser Asn Met Phe Phe Trp Trp Val Leu Pro Ile Leu
        115                 120                 125

Arg Val Gly Tyr Lys Arg Thr Ile Gln Pro Asn Asp Leu Phe Lys Met
    130                 135                 140

Asp Pro Arg Met Ser Ile Glu Thr Leu Tyr Asp Asp Phe Glu Lys Asn
145             150                 155                 160

Met Ile Tyr Tyr Phe Glu Lys Thr Arg Lys Lys Tyr Arg Lys Arg His
                165                 170                 175

Pro Glu Ala Thr Glu Glu Val Met Glu Asn Ala Lys Leu Pro Lys
                180                 185                 190

His Thr Val Leu Arg Ala Leu Leu Phe Thr Phe Lys Lys Gln Tyr Phe
        195                 200                 205

Met Ser Ile Val Phe Ala Ile Leu Ala Asn Cys Thr Ser Gly Phe Asn
    210                 215                 220

Pro Met Ile Thr Lys Arg Leu Ile Glu Phe Val Glu Glu Lys Ala Ile
225             230                 235                 240
```

Phe His Ser Met His Val Asn Lys Gly Ile Gly Tyr Ala Ile Gly Ala
            245                 250                 255

Cys Leu Met Met Phe Val Asn Gly Leu Thr Phe Asn His Phe Phe His
            260                 265                 270

Thr Ser Gln Leu Thr Gly Val Gln Ala Lys Ser Ile Leu Thr Lys Ala
            275                 280                 285

Ala Met Lys Lys Met Phe Asn Ala Ser Asn Tyr Ala Arg His Cys Phe
            290                 295                 300

Pro Asn Gly Lys Val Thr Ser Phe Val Thr Thr Asp Leu Ala Arg Ile
305                 310                 315                 320

Glu Phe Ala Leu Ser Phe Gln Pro Phe Leu Ala Gly Phe Pro Ala Ile
            325                 330                 335

Leu Ala Ile Cys Ile Val Leu Leu Ile Val Asn Leu Gly Pro Ile Ala
            340                 345                 350

Leu Val Gly Ile Gly Ile Phe Phe Gly Gly Phe Phe Ile Ser Leu Phe
            355                 360                 365

Ala Phe Lys Leu Ile Leu Gly Phe Arg Ile Ala Ala Asn Ile Phe Thr
            370                 375                 380

Asp Ala Arg Val Thr Met Met Arg Glu Val Leu Asn Asn Ile Lys Met
385                 390                 395                 400

Ile Lys Tyr Tyr Thr Trp Glu Asp Ala Tyr Glu Lys Asn Ile Gln Asp
            405                 410                 415

Ile Arg Thr Lys Glu Ile Ser Lys Val Arg Lys Met Gln Leu Ser Arg
            420                 425                 430

Asn Phe Leu Ile Ala Met Ala Met Ser Leu Pro Ser Ile Ala Ser Leu
            435                 440                 445

Val Thr Phe Leu Ala Met Tyr Lys Val Asn Lys Gly Gly Arg Gln Pro
            450                 455                 460

Gly Asn Ile Phe Ala Ser Leu Ser Leu Phe Gln Val Leu Ser Leu Gln
465                 470                 475                 480

Met Phe Phe Leu Pro Ile Ala Ile Gly Thr Gly Ile Asp Met Ile Ile
            485                 490                 495

Gly Leu Gly Arg Leu Gln Ser Leu Leu Glu Ala Pro Glu Asp Asp Pro
            500                 505                 510

Asn Gln Met Ile Glu Met Lys Pro Ser Pro Gly Phe Asp Pro Lys Leu
            515                 520                 525

Ala Leu Lys Met Thr His Cys Ser Phe Glu Trp Glu Asp Tyr Glu Leu
            530                 535                 540

Asn Asp Ala Ile Glu Glu Ala Lys Gly Glu Ala Lys Asp Glu Gly Lys
545                 550                 555                 560

Lys Asn Lys Lys Lys Arg Lys Asp Thr Trp Gly Lys Pro Ser Ala Ser
            565                 570                 575

Thr Asn Lys Ala Lys Arg Leu Asp Asn Met Leu Lys Asp Arg Asp Gly
            580                 585                 590

Pro Glu Asp Leu Glu Lys Thr Ser Phe Arg Gly Phe Lys Asp Leu Asn
            595                 600                 605

Phe Asp Ile Lys Lys Gly Glu Phe Ile Met Ile Thr Gly Pro Ile Gly
            610                 615                 620

Thr Gly Lys Ser Ser Leu Leu Asn Ala Met Ala Gly Ser Met Arg Lys
625                 630                 635                 640

Thr Asp Gly Lys Val Glu Val Asn Gly Asp Leu Leu Met Cys Gly Tyr
            645                 650                 655

```
Pro Trp Ile Gln Asn Ala Ser Val Arg Asp Asn Ile Ile Phe Gly Ser
            660                 665                 670

Pro Phe Asn Lys Glu Lys Tyr Asp Glu Val Val Arg Val Cys Ser Leu
            675                 680                 685

Lys Ala Asp Leu Asp Ile Leu Pro Ala Gly Asp Met Thr Glu Ile Gly
            690                 695                 700

Glu Arg Gly Ile Thr Leu Ser Gly Gly Gln Lys Ala Arg Ile Asn Leu
705                 710                 715                 720

Ala Arg Ser Val Tyr Lys Lys Asp Ile Tyr Leu Phe Asp Asp Val
                725                 730                 735

Leu Ser Ala Val Asp Ser Arg Val Gly Lys His Ile Met Asp Glu Cys
            740                 745                 750

Leu Thr Gly Met Leu Ala Asn Lys Thr Arg Ile Leu Ala Thr His Gln
            755                 760                 765

Leu Ser Leu Ile Glu Arg Ala Ser Arg Val Ile Val Leu Gly Thr Asp
            770                 775                 780

Gly Gln Val Asp Ile Gly Thr Val Asp Glu Leu Lys Ala Arg Asn Gln
785                 790                 795                 800

Thr Leu Ile Asn Leu Leu Gln Phe Ser Ser Gln Asn Ser Glu Lys Glu
            805                 810                 815

Asp Glu Glu Gln Glu Ala Val Val Ala Gly Glu Leu Gly Gln Leu Lys
            820                 825                 830

Tyr Glu Ser Glu Val Lys Glu Leu Thr Glu Leu Lys Lys Lys Ala Thr
            835                 840                 845

Glu Met Ser Gln Thr Ala Asn Ser Gly Lys Ile Val Ala Asp Gly His
850                 855                 860

Thr Ser Ser Lys Glu Glu Arg Ala Val Asn Ser Ile Ser Leu Lys Ile
865                 870                 875                 880

Tyr Arg Glu Tyr Ile Lys Ala Ala Val Gly Lys Trp Gly Phe Ile Ala
                885                 890                 895

Leu Pro Leu Tyr Ala Ile Leu Val Val Gly Thr Thr Phe Cys Ser Leu
            900                 905                 910

Phe Ser Ser Val Trp Leu Ser Tyr Trp Thr Glu Asn Lys Phe Lys Asn
            915                 920                 925

Arg Pro Pro Ser Phe Tyr Met Gly Leu Tyr Ser Phe Phe Val Phe Ala
930                 935                 940

Ala Phe Ile Phe Met Asn Gly Gln Phe Thr Ile Leu Cys Ala Met Gly
945                 950                 955                 960

Ile Met Ala Ser Lys Trp Leu Asn Leu Arg Ala Val Lys Arg Ile Leu
            965                 970                 975

His Thr Pro Met Ser Tyr Ile Asp Thr Thr Pro Leu Gly Arg Ile Leu
            980                 985                 990

Asn Arg Phe Thr Lys Asp Thr Asp Ser Leu Asp Asn Glu Leu Thr Glu
            995                 1000                1005

Ser Leu Arg Leu Met Thr Ser Gln Phe Ala Asn Ile Val Gly Val
            1010                1015                1020

Cys Val Met Cys Ile Val Tyr Leu Pro Trp Phe Ala Ile Ala Ile
            1025                1030                1035

Pro Phe Leu Leu Val Ile Phe Val Leu Ile Ala Asp His Tyr Gln
            1040                1045                1050

Ser Ser Gly Arg Glu Ile Lys Arg Leu Glu Ala Val Gln Arg Ser
            1055                1060                1065

Phe Val Tyr Asn Asn Leu Asn Glu Val Leu Gly Gly Met Asp Thr
```

-continued

```
            1070                1075                1080

Ile Lys Ala Tyr Arg Ser Gln Glu Arg Phe Leu Ala Lys Ser Asp
    1085                1090                1095

Phe Leu Ile Asn Lys Met Asn Glu Ala Gly Tyr Leu Val Val Val
    1100                1105                1110

Leu Gln Arg Trp Val Gly Ile Phe Leu Asp Met Val Ala Ile Ala
    1115                1120                1125

Phe Ala Leu Ile Ile Thr Leu Leu Cys Val Thr Arg Ala Phe Pro
    1130                1135                1140

Ile Ser Ala Ala Ser Val Gly Val Leu Leu Thr Tyr Val Leu Gln
    1145                1150                1155

Leu Pro Gly Leu Leu Asn Thr Ile Leu Arg Ala Met Thr Gln Thr
    1160                1165                1170

Glu Asn Asp Met Asn Ser Ala Glu Arg Leu Val Thr Tyr Ala Thr
    1175                1180                1185

Glu Leu Pro Leu Glu Ala Ser Tyr Arg Lys Pro Glu Met Thr Pro
    1190                1195                1200

Pro Glu Ser Trp Pro Ser Met Gly Glu Ile Ile Phe Glu Asn Val
    1205                1210                1215

Asp Phe Ala Tyr Arg Pro Gly Leu Pro Ile Val Leu Lys Asn Leu
    1220                1225                1230

Asn Leu Asn Ile Lys Ser Gly Glu Lys Ile Gly Ile Cys Gly Arg
    1235                1240                1245

Thr Gly Ala Gly Lys Ser Thr Ile Met Ser Ala Leu Tyr Arg Leu
    1250                1255                1260

Asn Glu Leu Thr Ala Gly Lys Ile Leu Ile Asp Asn Val Asp Ile
    1265                1270                1275

Ser Gln Leu Gly Leu Phe Asp Leu Arg Arg Lys Leu Ala Ile Ile
    1280                1285                1290

Pro Gln Asp Pro Val Leu Phe Arg Gly Thr Ile Arg Lys Asn Leu
    1295                1300                1305

Asp Pro Phe Asn Glu Arg Thr Asp Asp Glu Leu Trp Asp Ala Leu
    1310                1315                1320

Val Arg Gly Gly Ala Ile Ala Lys Asp Leu Pro Glu Val Lys
    1325                1330                1335

Leu Gln Lys Pro Asp Glu Asn Gly Thr His Gly Lys Met His Lys
    1340                1345                1350

Phe His Leu Asp Gln Ala Val Glu Glu Glu Gly Ser Asn Phe Ser
    1355                1360                1365

Leu Gly Glu Arg Gln Leu Leu Ala Leu Thr Arg Ala Leu Val Arg
    1370                1375                1380

Gln Ser Lys Ile Leu Ile Leu Asp Glu Ala Thr Ser Ser Val Asp
    1385                1390                1395

Tyr Glu Thr Asp Gly Lys Ile Gln Thr Arg Ile Val Glu Glu Phe
    1400                1405                1410

Gly Asp Cys Thr Ile Leu Cys Ile Ala His Arg Leu Lys Thr Ile
    1415                1420                1425

Val Asn Tyr Asp Arg Ile Leu Val Leu Glu Lys Gly Glu Val Ala
    1430                1435                1440

Glu Phe Asp Thr Pro Trp Thr Leu Phe Ser Gln Glu Asp Ser Ile
    1445                1450                1455

Phe Arg Ser Met Cys Ser Arg Ser Gly Ile Val Glu Asn Asp Phe
    1460                1465                1470
```

Glu Asn Arg Ser
        1475

<210> SEQ ID NO 13
<211> LENGTH: 1068
<212> TYPE: PRT
<213> ORGANISM: Saccharomyces cerevisiae

<400> SEQUENCE: 13

Met Arg Gly Leu Thr Pro Lys Asn Gly Val His Ile Glu Thr Gly Pro
1               5                   10                  15

Asp Thr Glu Ser Ser Ala Asp Ser Ser Asn Phe Ser Thr Gly Phe Ser
            20                  25                  30

Gly Lys Ile Arg Lys Pro Arg Ser Lys Val Ser Lys Ala Cys Asp Asn
        35                  40                  45

Cys Arg Lys Arg Lys Ile Lys Cys Asn Gly Lys Phe Pro Cys Ala Ser
    50                  55                  60

Cys Glu Ile Tyr Ser Cys Glu Cys Thr Phe Ser Thr Arg Gln Gly Gly
65                  70                  75                  80

Ala Arg Ile Lys Asn Leu His Lys Thr Ser Leu Glu Gly Thr Thr Val
                85                  90                  95

Gln Val Lys Glu Glu Thr Asp Ser Ser Ser Thr Ser Phe Ser Asn Pro
            100                 105                 110

Gln Arg Cys Thr Asp Gly Pro Cys Ala Val Glu Gln Pro Thr Lys Phe
        115                 120                 125

Phe Glu Asn Phe Lys Leu Gly Gly Arg Ser Ser Gly Asp Asn Ser Gly
    130                 135                 140

Ser Asp Gly Lys Asn Asp Asp Val Asn Arg Asn Gly Phe Tyr Glu
145                 150                 155                 160

Asp Asp Ser Glu Ser Gln Ala Thr Leu Thr Ser Leu Gln Thr Thr Leu
                165                 170                 175

Lys Asn Leu Lys Glu Met Ala His Leu Gly Thr His Val Thr Ser Ala
            180                 185                 190

Ile Glu Ser Ile Glu Leu Gln Ile Ser Asp Leu Leu Lys Arg Trp Glu
        195                 200                 205

Pro Lys Val Arg Thr Lys Glu Leu Ala Thr Thr Lys Phe Tyr Pro Asn
    210                 215                 220

Lys Ser Ile Glu Thr Gln Leu Met Lys Asn Lys Tyr Cys Asp Val Val
225                 230                 235                 240

His Leu Thr Arg Tyr Ala Ala Trp Ser Asn Asn Lys Lys Asp Gln Asp
                245                 250                 255

Thr Ser Ser Gln Pro Leu Ile Asp Glu Ile Phe Gly Leu Tyr Ser Pro
            260                 265                 270

Phe Gln Phe Leu Ser Leu Gln Gly Ile Gly Lys Cys Phe Gln Asn Tyr
        275                 280                 285

Arg Ser Lys Ser Lys Cys Glu Ile Phe Pro Arg Thr Ala Lys Glu Thr
    290                 295                 300

Ile Tyr Ile Met Leu Arg Phe Phe Asp Val Cys Phe His His Ile Asn
305                 310                 315                 320

Gln Gly Cys Val Ser Ile Ala Asn Pro Leu Glu Asn Tyr Leu Gln Lys
                325                 330                 335

Met Asn Leu Leu Pro Ser Thr Pro Ser Ser Ile Ser Ser Ala Gly Ser
            340                 345                 350

Pro Asn Thr Ala His Thr Lys Ser His Val Ala Leu Val Ile Asn His

```
              355                 360                 365
Leu Pro Gln Pro Phe Val Arg Asn Ile Thr Gly Ile Ser Asn Ser Glu
370                 375                 380
Leu Leu Ser Glu Met Asn Asn Asp Ile Ser Met Phe Gly Ile Leu Leu
385                 390                 395                 400
Lys Met Leu Asp Met His Lys Asn Ser Tyr Gln Asn Phe Leu Met Glu
                405                 410                 415
Ile Thr Ser Asn Pro Ser Val Ala Lys Asn Thr Gln Ser Ile Asp Val
                420                 425                 430
Leu Gln Glu Phe Ile His Tyr Cys Gln Ala Gly Glu Ala Leu Ile Ala
                435                 440                 445
Leu Cys Tyr Ser Tyr Tyr Asn Ser Thr Leu Tyr Asn Tyr Val Asp Phe
        450                 455                 460
Thr Cys Asp Ile Thr His Leu Glu Gln Leu Leu Tyr Phe Leu Asp Leu
465                 470                 475                 480
Leu Phe Trp Leu Ser Glu Ile Tyr Gly Phe Glu Lys Val Leu Asn Val
                485                 490                 495
Ala Val His Phe Val Ser Arg Val Gly Leu Ser Arg Trp Glu Phe Tyr
                500                 505                 510
Val Gly Leu Asp Glu Asn Phe Ala Glu Arg Arg Asn Leu Trp Trp
                515                 520                 525
Lys Ala Phe Tyr Phe Glu Lys Thr Leu Ala Ser Lys Leu Gly Tyr Pro
530                 535                 540
Ser Asn Ile Asp Asp Ser Lys Ile Asn Cys Leu Leu Pro Lys Asn Phe
545                 550                 555                 560
Arg Asp Val Gly Phe Leu Asp Asn Arg Asp Phe Ile Glu Asn Val His
                565                 570                 575
Leu Val Arg Arg Ser Glu Ala Phe Asp Asn Met Cys Ile Ser Asp Leu
                580                 585                 590
Lys Tyr Tyr Gly Glu Leu Ala Val Leu Gln Ile Val Ser His Phe Ser
                595                 600                 605
Ser Ser Val Leu Phe Asn Glu Lys Phe Thr Ser Ile Arg Asn Thr Ser
        610                 615                 620
Lys Pro Ser Val Val Arg Glu Lys Leu Leu Phe Glu Val Leu Glu Ile
625                 630                 635                 640
Phe Asn Glu Thr Glu Met Lys Tyr Asp Ala Ile Lys Glu Gln Thr Gly
                645                 650                 655
Lys Leu Phe Asp Ile Ala Phe Ser Lys Asp Ser Thr Glu Leu Lys Val
                660                 665                 670
Ser Arg Glu Asp Lys Ile Met Ala Ser Lys Phe Val Leu Phe Tyr Glu
        675                 680                 685
His His Phe Cys Arg Met Val Asn Glu Ser Asp Asn Ile Val Ala Arg
        690                 695                 700
Leu Cys Val His Arg Arg Pro Ser Ile Leu Ile Glu Asn Leu Lys Ile
705                 710                 715                 720
Tyr Leu His Lys Ile Tyr Lys Ser Trp Thr Asp Met Asn Lys Ile Leu
                725                 730                 735
Leu Asp Phe Asp Asn Asp Tyr Ser Val Tyr Arg Ser Phe Ala His Tyr
                740                 745                 750
Ser Ile Ser Cys Ile Ile Leu Val Ser Gln Ala Phe Ser Val Ala Glu
        755                 760                 765
Phe Ile Lys Val Asn Asp Val Val Asn Met Ile Arg Val Phe Lys Arg
770                 775                 780
```

Phe Leu Asp Ile Lys Ile Phe Ser Glu Asn Glu Thr Asn Glu His Val
785                 790                 795                 800

Phe Asn Ser Gln Ser Phe Lys Asp Tyr Thr Arg Ala Phe Ser Phe Leu
            805                 810                 815

Thr Ile Val Thr Arg Ile Met Leu Leu Ala Tyr Gly Leu Ser Ser Ser
            820                 825                 830

Thr Asn Leu Asp Val Ile Ser Lys Tyr Ile Asp Glu Asn Ala Pro Asp
            835                 840                 845

Leu Lys Gly Ile Ile Glu Leu Val Leu Asp Thr Asn Ser Cys Ala Tyr
            850                 855                 860

Arg Phe Leu Leu Glu Pro Val Gln Lys Ser Gly Phe His Leu Thr Val
865                 870                 875                 880

Ser Gln Met Leu Lys Asn Arg Lys Phe Gln Glu Pro Leu Met Ser Asn
            885                 890                 895

Glu Asp Asn Lys Gln Met Lys His Asn Ser Gly Lys Asn Leu Asn Pro
            900                 905                 910

Asp Leu Pro Ser Leu Lys Thr Gly Thr Ser Cys Leu Leu Asn Gly Ile
            915                 920                 925

Glu Ser Pro Gln Leu Pro Phe Asn Gly Arg Ser Ala Pro Ser Pro Val
            930                 935                 940

Arg Asn Asn Ser Leu Pro Glu Phe Ala Gln Leu Pro Ser Phe Arg Ser
945                 950                 955                 960

Leu Ser Val Ser Asp Met Ile Asn Pro Asp Tyr Ala Gln Pro Thr Asn
            965                 970                 975

Gly Gln Asn Asn Thr Gln Val Gln Ser Asn Lys Pro Ile Asn Ala Gln
            980                 985                 990

Gln Gln Ile Pro Thr Ser Val Gln Val Pro Phe Met Asn Thr Asn Glu
            995                 1000                1005

Ile Asn Asn Asn Asn Asn Asn Asn Asn Asn Lys Asn Asn Ile
            1010                1015                1020

Asn Asn Ile Asn Asn Asn Asn Ser Asn Asn Phe Ser Ala Thr Ser
            1025                1030                1035

Phe Asn Leu Gly Thr Leu Asp Glu Phe Val Asn Asn Gly Asp Leu
            1040                1045                1050

Glu Asp Leu Tyr Ser Ile Leu Trp Ser Asp Val Tyr Pro Asp Ser
            1055                1060                1065

<210> SEQ ID NO 14
<211> LENGTH: 976
<212> TYPE: PRT
<213> ORGANISM: Saccharomyces cerevisiae

<400> SEQUENCE: 14

Met Lys Val Lys Lys Ser Thr Arg Ser Lys Val Ser Thr Ala Cys Val
1               5                   10                  15

Asn Cys Arg Lys Arg Lys Ile Lys Cys Thr Gly Lys Tyr Pro Cys Thr
            20                  25                  30

Asn Cys Ile Ser Tyr Asp Cys Thr Cys Val Phe Leu Lys Lys His Leu
            35                  40                  45

Pro Gln Lys Glu Asp Ser Gln Ser Leu Pro Thr Thr Ala Val Ala
            50                  55                  60

Pro Pro Ser Ser His Ala Asn Val Glu Ala Ser Ala Asp Val Gln His
65                  70                  75                  80

Leu Asp Thr Ala Ile Lys Leu Asp Asn Gln Tyr Tyr Phe Lys Leu Met

-continued

```
                85                  90                  95
Asn Asp Leu Ile Gln Thr Pro Val Ser Pro Ser Ala Thr His Ala Pro
                100                 105                 110
Asp Thr Ser Asn Asn Pro Thr Asn Asp Asn Asn Ile Leu Phe Lys Asp
                115                 120                 125
Asp Ser Lys Tyr Gln Asn Gln Leu Val Thr Tyr Gln Asn Ile Leu Thr
130                 135                 140
Asn Leu Tyr Ala Leu Pro Pro Cys Asp Asp Thr Gln Leu Leu Ile Asp
145                 150                 155                 160
Lys Thr Lys Ser Gln Leu Asn Asn Leu Ile Asn Ser Trp Asn Pro Glu
                165                 170                 175
Ile Asn Tyr Pro Lys Leu Ser Ser Phe Ser Pro Arg Pro Gln Arg Ser
                180                 185                 190
Ile Glu Thr Tyr Leu Leu Thr Asn Lys Tyr Arg Asn Lys Ile His Met
                195                 200                 205
Thr Arg Phe Ser Phe Trp Thr Asp Gln Met Val Lys Ser Gln Ser Pro
                210                 215                 220
Asp Ser Phe Leu Ala Thr Thr Pro Leu Val Asp Glu Val Phe Gly Leu
225                 230                 235                 240
Phe Ser Pro Ile Gln Ala Phe Ser Leu Arg Gly Ile Gly Tyr Leu Ile
                245                 250                 255
Lys Lys Asn Ile Glu Asn Thr Gly Ser Ser Met Leu Ile Asp Thr Lys
                260                 265                 270
Glu Thr Ile Tyr Leu Ile Leu Arg Leu Phe Asp Leu Cys Tyr Glu His
                275                 280                 285
Leu Ile Gln Gly Cys Ile Ser Ile Ser Asn Pro Leu Glu Asn Tyr Leu
                290                 295                 300
Gln Lys Ile Lys Gln Thr Pro Thr Thr Thr Ala Ser Ala Ser Leu Pro
305                 310                 315                 320
Thr Ser Pro Ala Pro Leu Ser Asn Asp Leu Val Ile Ser Val Ile His
                325                 330                 335
Gln Leu Pro Gln Pro Phe Ile Gln Ser Ile Thr Gly Phe Thr Thr Thr
                340                 345                 350
Gln Leu Ile Glu Asn Leu His Asp Ser Phe Ser Met Phe Arg Ile Val
                355                 360                 365
Thr Gln Met Tyr Ala Gln His Arg Lys Arg Phe Ala Glu Phe Leu Asn
                370                 375                 380
Gln Ala Phe Ser Leu Pro His Gln Glu Lys Ser Val Leu Phe Ser Ser
385                 390                 395                 400
Phe Cys Ser Ser Glu Tyr Leu Leu Ser Thr Leu Cys Tyr Ala Tyr Tyr
                405                 410                 415
Asn Val Thr Leu Tyr His Met Leu Asp Ile Asn Thr Leu Asp Tyr Leu
                420                 425                 430
Glu Ile Leu Val Ser Leu Leu Glu Ile Gln Asn Glu Ile Asp Glu Arg
                435                 440                 445
Phe Gly Phe Glu Lys Met Leu Glu Val Ala Val Thr Cys Ser Thr Lys
                450                 455                 460
Met Gly Leu Ser Arg Trp Glu Tyr Tyr Val Gly Ile Asp Glu Asn Thr
465                 470                 475                 480
Ala Glu Arg Arg Arg Lys Ile Trp Trp Lys Ile Tyr Ser Leu Glu Lys
                485                 490                 495
Arg Phe Leu Thr Asp Leu Gly Asp Leu Ser Leu Ile Asn Glu His Gln
                500                 505                 510
```

```
Met Asn Cys Leu Leu Pro Lys Asp Phe Arg Asp Met Gly Phe Ile Asn
            515                 520                 525

His Lys Glu Phe Leu Thr Lys Ile Gly Thr Ser Ser Leu Ser Pro Ser
        530                 535                 540

Ser Pro Lys Leu Lys Asn Leu Ser Leu Ser Arg Leu Ile Glu Tyr Gly
545                 550                 555                 560

Glu Leu Ala Ile Ala Gln Ile Val Gly Asp Phe Phe Ser Glu Thr Leu
                565                 570                 575

Tyr Asn Glu Lys Phe Thr Ser Leu Glu Val Ser Val Lys Pro Thr Ile
            580                 585                 590

Ile Arg Gln Lys Leu Leu Glu Lys Val Phe Glu Asp Ile Glu Ser Phe
        595                 600                 605

Arg Leu Lys Leu Ala Lys Ile Lys Leu His Thr Ser Arg Val Phe Gln
        610                 615                 620

Val Ala His Cys Lys Tyr Pro Glu Tyr Pro Lys Asn Asp Leu Ile Glu
625                 630                 635                 640

Ala Ala Lys Phe Val Ser Tyr His Lys Asn Thr Trp Phe Ser Ile Leu
                645                 650                 655

Gly Ala Val Asn Asn Leu Ile Ala Arg Leu Ser Glu Asp Pro Glu Val
            660                 665                 670

Ile Thr Glu Gln Ser Met Lys Tyr Ala Asn Glu Met Phe Gln Glu Trp
        675                 680                 685

Arg Glu Ile Asn Gln Phe Leu Ile Gln Val Asp Thr Asp Phe Ile Val
        690                 695                 700

Trp Ala Cys Leu Asp Phe Tyr Glu Leu Ile Phe Val Met Ala Ser
705                 710                 715                 720

Lys Phe Tyr Val Glu Asp Pro His Ile Thr Leu Glu Asp Val Ile Asn
                725                 730                 735

Thr Leu Lys Val Phe Lys Arg Ile Thr Asn Ile Ile Ser Phe Phe Asn
            740                 745                 750

Asn Asn Leu Asp Glu Lys Asp Tyr Asp Cys Gln Thr Phe Arg Glu Phe
        755                 760                 765

Ser Arg Ser Ser Ser Leu Val Ala Ile Ser Ile Arg Ile Ile Phe Leu
        770                 775                 780

Lys Tyr Cys Tyr Ala Glu Gln Ile Asp Arg Ala Glu Phe Ile Glu Arg
785                 790                 795                 800

Leu Lys Glu Val Glu Pro Gly Leu Ser Asp Leu Leu Arg Glu Phe Phe
                805                 810                 815

Asp Thr Arg Ser Phe Ile Tyr Arg Tyr Met Leu Lys Ser Val Glu Lys
            820                 825                 830

Ser Gly Phe His Leu Ile Ile Arg Lys Met Leu Glu Ser Asp Tyr Lys
        835                 840                 845

Phe Leu Tyr Arg Asp Lys Leu Ala Thr Gly Asn Ile Pro Asp Gln Gly
850                 855                 860

Asn Ser Ser Gln Ile Ser Gln Leu Tyr Asp Ser Thr Ala Pro Ser Tyr
865                 870                 875                 880

Asn Asn Ala Ser Ala Ser Ala Ala Asn Ser Pro Leu Lys Leu Ser Ser
                885                 890                 895

Leu Leu Asn Ser Gly Glu Glu Ser Tyr Thr Gln Asp Ala Ser Glu Asn
            900                 905                 910

Val Pro Cys Asn Leu Arg His Gln Asp Arg Ser Leu Gln Gln Thr Lys
        915                 920                 925
```

```
Arg Gln His Ser Ala Pro Ser Gln Ile Ser Ala Asn Glu Asn Asn Ile
    930                 935                 940

Tyr Asn Leu Gly Thr Leu Glu Glu Phe Val Ser Ser Gly Asp Leu Thr
945                 950                 955                 960

Asp Leu Tyr His Thr Leu Trp Asn Asp Asn Thr Ser Tyr Pro Phe Leu
                965                 970                 975

<210> SEQ ID NO 15
<211> LENGTH: 586
<212> TYPE: PRT
<213> ORGANISM: Saccharomyces cerevisiae

<400> SEQUENCE: 15

Met Ser Arg Ser Asn Ser Ile Tyr Thr Glu Asp Ile Glu Met Tyr Pro
1               5                   10                  15

Thr His Asn Glu Gln His Leu Thr Arg Glu Tyr Thr Lys Pro Asp Gly
            20                  25                  30

Gln Thr Lys Ser Glu Lys Leu Asn Phe Glu Gly Ala Tyr Ile Asn Ser
        35                  40                  45

His Gly Thr Leu Ser Lys Thr Thr Arg Glu Ile Glu Gly Asp Leu
    50                  55                  60

Asp Ser Glu Thr Ser Ser His Ser Ser Asp Asp Lys Val Asp Pro Thr
65                  70                  75                  80

Gln Gln Ile Thr Ala Glu Thr Lys Ala Pro Tyr Thr Leu Leu Ser Tyr
                85                  90                  95

Gly Gln Lys Trp Gly Met Val Ala Ile Leu Thr Met Cys Gly Phe Trp
            100                 105                 110

Ser Ser Leu Gly Ser Pro Ile Tyr Tyr Pro Ala Leu Arg Gln Leu Glu
        115                 120                 125

Lys Gln Phe Asn Val Asp Glu Asn Met Val Asn Val Thr Val Val Val
    130                 135                 140

Tyr Leu Leu Phe Gln Gly Ile Ser Pro Thr Val Ser Gly Gly Leu Ala
145                 150                 155                 160

Asp Cys Phe Gly Arg Arg Pro Ile Ile Leu Ala Gly Met Leu Ile Tyr
                165                 170                 175

Val Ile Ala Ser Ile Gly Leu Ala Cys Ala Pro Ser Tyr Gly Val Ile
            180                 185                 190

Ile Phe Leu Arg Cys Ile Gln Ser Ile Gly Ile Ser Pro Thr Ile Ala
        195                 200                 205

Ile Ser Ser Gly Val Val Gly Asp Phe Thr Leu Lys His Glu Arg Gly
    210                 215                 220

Thr Phe Val Gly Ala Thr Ser Gly Phe Val Leu Leu Gly Gln Cys Phe
225                 230                 235                 240

Gly Ser Leu Ile Gly Ala Val Leu Thr Ala Arg Trp Asp Trp Arg Ala
                245                 250                 255

Ile Phe Trp Phe Leu Thr Ile Gly Cys Gly Ser Cys Phe Leu Ile Ala
            260                 265                 270

Phe Leu Ile Leu Pro Glu Thr Lys Arg Thr Ile Ala Gly Asn Leu Ser
        275                 280                 285

Ile Lys Pro Lys Arg Phe Ile Asn Arg Ala Pro Ile Phe Leu Leu Gly
    290                 295                 300

Pro Val Arg Arg Arg Phe Lys Tyr Asp Asn Pro Asp Tyr Glu Thr Leu
305                 310                 315                 320

Asp Pro Thr Ile Pro Lys Leu Asp Leu Ser Ser Ala Gly Lys Ile Leu
                325                 330                 335
```

```
Val Leu Pro Glu Ile Ile Leu Ser Leu Phe Pro Ser Gly Leu Leu Phe
            340                 345                 350

Ala Met Trp Thr Leu Met Leu Ser Ile Ser Ser Gly Leu Ser Val
        355                 360                 365

Ala Pro Tyr Asn Tyr His Leu Val Ile Ile Gly Val Cys Tyr Leu Pro
        370                 375                 380

Gly Gly Ile Gly Gly Leu Met Gly Ser Phe Phe Thr Gly Arg Ile Ile
385                 390                 395                 400

Asp Met Tyr Phe Lys Arg Lys Ile Lys Lys Phe Glu Gln Asp Lys Ala
                405                 410                 415

Asn Gly Leu Ile Pro Gln Asp Ala Glu Ile Asn Met Phe Lys Val Arg
            420                 425                 430

Leu Val Cys Leu Leu Pro Gln Asn Phe Leu Ala Val Val Ala Tyr Leu
            435                 440                 445

Leu Phe Gly Trp Ser Ile Asp Lys Gly Trp Arg Ile Glu Ser Ile Leu
450                 455                 460

Ile Thr Ser Phe Val Cys Ser Tyr Cys Ala Met Ser Thr Leu Ser Thr
465                 470                 475                 480

Ser Thr Thr Leu Leu Val Asp Leu Tyr Pro Thr Lys Ser Ser Thr Ala
                485                 490                 495

Ser Ser Cys Phe Asn Phe Val Arg Cys Ser Leu Ser Thr Ile Phe Met
                500                 505                 510

Gly Cys Phe Ala Lys Met Lys Ala Ala Met Thr Val Gly Gly Thr Phe
            515                 520                 525

Thr Phe Leu Cys Ala Leu Val Phe Phe Asn Phe Leu Met Phe Ile
        530                 535                 540

Pro Met Lys Tyr Gly Met Lys Trp Arg Glu Asp Arg Leu Leu Lys Gln
545                 550                 555                 560

Gln Arg Gln Ser Trp Leu Asn Thr Leu Ala Val Lys Ala Lys Lys Gly
                565                 570                 575

Thr Lys Arg Asp Gln Asn Asp Asn His Asn
                580                 585

<210> SEQ ID NO 16
<211> LENGTH: 572
<212> TYPE: PRT
<213> ORGANISM: Saccharomyces cerevisiae

<400> SEQUENCE: 16

Met Gly Ser Glu Pro Phe Gln Lys Lys Asn Leu Gly Leu Gln Ile Asn
1               5                   10                  15

Ser Gln Glu Ser Gly Thr Thr Arg Ser Thr Phe His Ser Leu Glu Asp
            20                  25                  30

Leu Gly Asp Asp Val Ile Asn Glu Ser Trp Asp Gln Val Asn Gln Lys
        35                  40                  45

Arg Ala Asn Ile Asp His Asp Val Phe His Glu His Pro Asp Ser Ser
    50                  55                  60

Pro Ser Leu Ser Ala Gln Lys Ala Lys Thr Lys Glu Glu Val Ala
65                  70                  75                  80

Val Lys Ser Ser Asn Ser Gln Ser Arg Asp Pro Ser Pro Asp Thr Gln
                85                  90                  95

Ala His Ile Pro Tyr Thr Tyr Phe Ser Lys Asp Gln Arg Leu Ile Ile
            100                 105                 110

Phe Gly Ile Ile Ile Phe Ile Gly Phe Leu Gly Pro Met Ser Gly Asn
```

-continued

```
            115                 120                 125
Ile Tyr Ile Pro Ala Leu Pro Leu Leu Gln Arg Glu Tyr Asp Val Ser
            130                 135                 140
Ala Thr Thr Ile Asn Ala Thr Val Ser Val Phe Met Ala Val Phe Ser
145                 150                 155                 160
Val Gly Pro Leu Phe Trp Gly Ala Leu Ala Asp Phe Gly Gly Arg Lys
                    165                 170                 175
Phe Leu Tyr Met Val Ser Leu Ser Leu Met Leu Ile Val Asn Ile Leu
                180                 185                 190
Leu Ala Ala Val Pro Val Asn Ile Ala Ala Leu Phe Val Leu Arg Ile
            195                 200                 205
Phe Gln Ala Phe Ala Ser Ser Ser Val Ile Ser Leu Gly Ala Gly Thr
        210                 215                 220
Val Thr Asp Val Val Pro Pro Lys His Arg Gly Lys Ala Ile Ala Tyr
225                 230                 235                 240
Phe Met Met Gly Pro Asn Met Gly Pro Ile Ile Ala Pro Ile Val Ala
                    245                 250                 255
Gly Leu Ile Leu Met Lys Gly Asn Tyr Trp Arg Trp Leu Phe Gly Phe
                260                 265                 270
Thr Ser Ile Met Thr Gly Ile Ala Leu Ile Leu Val Thr Ala Leu Leu
            275                 280                 285
Pro Glu Thr Leu Arg Cys Ile Val Gly Asn Gly Asp Pro Lys Trp Gly
        290                 295                 300
Asp Lys Lys Asp Glu Arg Glu Asn Asn Glu Ser Pro Phe Phe Glu Gly
305                 310                 315                 320
Asn Lys Ile Ser His Arg Arg Leu Phe Pro Asp Ile Gly Ile Arg Lys
                    325                 330                 335
Pro Val Asn Asn Asp Ala Phe Phe Gln Glu Asn Phe Pro Lys Pro Pro
                340                 345                 350
Lys Ala Gly Leu Thr Leu Tyr Trp Lys Met Ile Lys Cys Pro Pro Ile
            355                 360                 365
Ile Ile Thr Ser Val Ser Thr Ala Leu Leu Phe Ser Ser Tyr Tyr Ala
        370                 375                 380
Phe Ser Val Thr Phe Ser Tyr Tyr Leu Glu His Asp Tyr Arg Phe Thr
385                 390                 395                 400
Met Leu Glu Ile Gly Ala Ala Tyr Val Cys Pro Gly Val Ala Met Leu
                    405                 410                 415
Leu Gly Ser Gln Ser Gly Gly His Leu Ser Asp Tyr Leu Arg Ser Arg
                420                 425                 430
Trp Ile Lys Ser His Pro Lys Lys Lys Phe Pro Ala Glu Phe Arg Leu
            435                 440                 445
Leu Leu Asn Leu Ile Gly Ile Leu Leu Thr Ile Cys Gly Thr Ile Gly
        450                 455                 460
Tyr Gly Trp Ala Ile Phe Phe His Tyr His Phe Val Val Leu Leu Val
465                 470                 475                 480
Phe Ser Ala Leu Thr Ala Phe Gly Met Thr Trp Cys Ser Asn Thr Ser
                    485                 490                 495
Met Thr Tyr Leu Thr Glu Leu Phe Pro Lys Arg Ala Ala Gly Thr Val
                500                 505                 510
Ala Val Ser Ser Phe Phe Arg Asn Val Gly Ala Ala Ile Ser Ser Ala
            515                 520                 525
Ile Ile Leu Gln Leu Cys Asn Ala Met Gly Ile Gly Trp Cys Phe Thr
        530                 535                 540
```

Gly Leu Gly Leu Cys Ser Ser Ile Ser Leu Ile Gly Ile Leu Tyr Leu
545                 550                 555                 560

Leu Ile Phe Gln Arg Lys Tyr Thr Ala Lys Glu Phe
            565                 570

<210> SEQ ID NO 17
<211> LENGTH: 548
<212> TYPE: PRT
<213> ORGANISM: Saccharomyces cerevisiae

<400> SEQUENCE: 17

Met Val Tyr Thr Ser Thr Tyr Arg His Thr Ile Val Val Asp Leu Leu
1               5                   10                  15

Glu Tyr Leu Gly Ile Val Ser Asn Leu Glu Thr Leu Gln Ser Ala Arg
            20                  25                  30

Glu Asp Glu Thr Arg Lys Pro Glu Asn Thr Asp Lys Lys Glu Cys Lys
        35                  40                  45

Pro Asp Tyr Asp Ile Glu Cys Gly Pro Asn Arg Ser Cys Ser Glu Ser
    50                  55                  60

Ser Thr Asp Ser Asp Ser Ser Gly Ser Gln Ile Glu Lys Asn Asp Pro
65                  70                  75                  80

Phe Arg Val Asp Trp Asn Gly Pro Ser Asp Pro Glu Asn Pro Gln Asn
                85                  90                  95

Trp Pro Leu Leu Lys Lys Ser Leu Val Val Phe Gln Ile Met Leu Leu
            100                 105                 110

Thr Cys Val Thr Tyr Met Gly Ser Ser Ile Tyr Thr Pro Gly Gln Glu
        115                 120                 125

Tyr Ile Gln Glu Glu Phe His Val Gly His Val Val Ala Thr Leu Asn
    130                 135                 140

Leu Ser Leu Tyr Val Leu Gly Tyr Gly Leu Gly Pro Ile Ile Phe Ser
145                 150                 155                 160

Pro Leu Ser Glu Thr Ala Arg Tyr Gly Arg Leu Asn Leu Tyr Met Val
                165                 170                 175

Thr Leu Phe Phe Phe Met Ile Phe Gln Val Gly Cys Ala Thr Val His
            180                 185                 190

Asn Ile Gly Gly Leu Ile Val Met Arg Phe Ile Ser Gly Ile Leu Cys
        195                 200                 205

Ser Pro Ser Leu Ala Thr Gly Gly Thr Val Ala Asp Ile Ile Ser
    210                 215                 220

Pro Glu Met Val Pro Leu Val Leu Gly Met Trp Ser Ala Gly Ala Val
225                 230                 235                 240

Ala Ala Pro Val Leu Ala Pro Leu Leu Gly Ala Ala Met Val Asp Ala
                245                 250                 255

Lys Asn Trp Arg Phe Ile Phe Trp Leu Leu Met Trp Leu Ser Ala Ala
            260                 265                 270

Thr Phe Ile Leu Leu Ala Phe Phe Pro Glu Thr Gln His His Asn
        275                 280                 285

Ile Leu Tyr Arg Arg Ala Leu Lys Leu Arg Lys Glu Thr Gly Asp Asp
    290                 295                 300

Arg Tyr Tyr Thr Glu Gln Asp Lys Leu Asp Arg Glu Val Asp Ala Arg
305                 310                 315                 320

Thr Phe Leu Ile Asn Thr Leu Tyr Arg Pro Leu Lys Met Ile Ile Lys
                325                 330                 335

Glu Pro Ala Ile Leu Ala Phe Asp Leu Tyr Ile Ala Val Ala Tyr Gly

```
                    340                 345                 350
Cys Phe Tyr Leu Phe Phe Glu Ala Phe Pro Ile Val Phe Val Gly Ile
                355                 360                 365

Tyr His Phe Ser Leu Val Glu Val Gly Leu Ala Tyr Met Gly Phe Cys
            370                 375                 380

Val Gly Cys Val Leu Ala Tyr Gly Leu Phe Gly Ile Leu Asn Met Arg
385                 390                 395                 400

Ile Ile Val Pro Arg Phe Arg Asn Gly Thr Phe Thr Pro Glu Ala Phe
                405                 410                 415

Leu Ile Val Ala Met Cys Val Cys Trp Cys Leu Pro Leu Ser Leu Phe
            420                 425                 430

Leu Phe Gly Trp Thr Ala Arg Val His Trp Ile Leu Pro Val Ile Ser
        435                 440                 445

Glu Val Phe Phe Val Leu Ala Val Phe Asn Ile Phe Gln Ala Thr Phe
    450                 455                 460

Ala Tyr Leu Ala Thr Cys Tyr Pro Lys Tyr Val Ala Ser Val Phe Ala
465                 470                 475                 480

Gly Asn Gly Phe Cys Arg Ala Ser Phe Ala Cys Ala Phe Pro Leu Phe
                485                 490                 495

Gly Arg Ala Met Tyr Asp Asn Leu Ala Thr Lys Asn Tyr Pro Val Ala
            500                 505                 510

Trp Gly Ser Ser Leu Val Gly Phe Leu Thr Leu Gly Leu Ala Ile Ile
        515                 520                 525

Pro Phe Ile Leu Tyr Lys Tyr Gly Pro Ser Leu Arg Thr Arg Ser Ser
    530                 535                 540

Tyr Thr Glu Glu
545

<210> SEQ ID NO 18
<211> LENGTH: 586
<212> TYPE: PRT
<213> ORGANISM: Saccharomyces cerevisiae

<400> SEQUENCE: 18

Met Asp Lys Tyr Thr Asn Arg Asp His Pro Asp Tyr Ile Pro Gly Thr
1               5                   10                  15

Phe Asn Ile Tyr Ser Ser Gln Asn Leu Glu Asn Gly Ile Ile Tyr Glu
            20                  25                  30

Ser Lys Leu Lys Lys Thr Ser Ser Gly Val Val Leu Ile Pro Gln Pro
        35                  40                  45

Ser Tyr Ser Pro Asn Asp Pro Leu Asn Trp Ser Ser Trp Arg Lys Leu
    50                  55                  60

Ala His Phe Gly Leu Met Ala Phe Ile Thr Ala Phe Thr Ala Ala Thr
65                  70                  75                  80

Ser Asn Asp Ala Gly Ala Ala Gln Asp Ser Leu Asn Glu Ile Tyr Gly
                85                  90                  95

Ile Ser Tyr Asp Ser Met Asn Thr Gly Ala Gly Val Leu Phe Leu Gly
            100                 105                 110

Ile Gly Trp Ser Thr Leu Phe Leu Ala Pro Phe Ala Asn Leu Tyr Gly
        115                 120                 125

Arg Lys Ile Thr Tyr Ile Val Cys Thr Thr Leu Gly Leu Phe Gly Ala
    130                 135                 140

Leu Trp Phe Ala Leu Ala Lys Arg Thr Ser Asp Thr Ile Trp Ser Gln
145                 150                 155                 160
```

```
Leu Phe Val Gly Ile Ser Glu Ser Cys Ala Glu Ala Gln Val Gln Leu
                165                 170                 175

Ser Leu Ser Asp Ile Phe Phe Gln His Gln Leu Gly Ser Val Leu Thr
            180                 185                 190

Val Tyr Ile Met Cys Thr Ser Ile Gly Thr Phe Leu Gly Pro Leu Ile
        195                 200                 205

Ala Gly Tyr Ile Ser Ala Phe Thr Asn Phe Arg Trp Val Gly Trp Val
    210                 215                 220

Ala Val Ile Ile Ser Gly Gly Leu Leu Ile Thr Ile Phe Gly Cys
225                 230                 235                 240

Glu Glu Thr Tyr Phe Asp Arg Gly Gln Tyr Met Thr Pro Leu Thr Ser
                245                 250                 255

Cys Gln Ser Gly Tyr Glu Asp Gly Thr Thr Leu Gln Asn Ser Asp Asn
            260                 265                 270

Thr Ala Val Ser Arg Arg Lys Arg His Leu Asp Ala Lys Leu Ser Thr
        275                 280                 285

Pro Gly Ala Met Gly Glu Lys Gly Val Asp Leu Ser Glu Thr Ala Glu
    290                 295                 300

Phe Glu Val Asn Asn Glu Glu Val Thr Ile Pro Glu Thr Arg Glu
305                 310                 315                 320

Leu Ile Asp Gly Ser Lys Glu His Leu Lys Pro Tyr Pro Lys Arg Val
                325                 330                 335

Ala Ile Leu Thr Lys Ala Thr Asn Leu Lys Gly Tyr Gly Phe Lys Gln
            340                 345                 350

Tyr Phe Lys Tyr Leu Lys Ile Asn Leu Arg Met Phe Leu Phe Pro Pro
        355                 360                 365

Val Trp Leu Ser Gly Met Phe Trp Gly Ile Gln Asp Val Phe Leu Thr
    370                 375                 380

Phe Tyr Leu Thr Thr Gln Glu Ser Ala Tyr Tyr Glu Pro Pro Trp Asn
385                 390                 395                 400

Tyr Ser Asp Phe Gly Val Ala Ile Met Asn Val Pro Thr Leu Ile Gly
                405                 410                 415

Ala Val Ile Gly Cys Ile Cys Ala Gly Ile Val Ser Asp Tyr Phe Val
            420                 425                 430

Leu Trp Met Ala Arg His Asn Arg Gly Ile Leu Glu Ala Glu Phe Arg
        435                 440                 445

Leu Tyr Phe Ser Ile Ala Thr Ala Ile Ile Gly Pro Ala Gly Leu Leu
    450                 455                 460

Met Phe Gly Ile Gly Thr Ala Arg Gln Trp Pro Trp Gln Ala Ile Tyr
465                 470                 475                 480

Val Gly Leu Gly Phe Val Gly Phe Ala Trp Gly Cys Ser Gly Asp Ile
                485                 490                 495

Ala Met Ala Tyr Leu Met Asp Cys Tyr Pro Asp Met Val Leu Glu Gly
            500                 505                 510

Met Val Cys Thr Ala Ile Ile Asn Asn Thr Ile Ser Cys Ile Phe Thr
        515                 520                 525

Phe Thr Cys Ser Asp Trp Leu Ala Ala Ser Gly Thr Glu Asn Thr Tyr
    530                 535                 540

Ile Ala Leu Ala Val Ile Asn Phe Gly Ile Thr Ala Phe Ala Leu Pro
545                 550                 555                 560

Met Tyr Tyr Tyr Gly Lys Arg Ile Arg Leu Trp Thr Lys Arg Trp Tyr
                565                 570                 575

Leu Gln Ser Val Asn Leu Arg Asp Gly Val
```

-continued

```
              580                 585
```

<210> SEQ ID NO 19
<211> LENGTH: 563
<212> TYPE: PRT
<213> ORGANISM: Saccharomyces cerevisiae

<400> SEQUENCE: 19

```
Met Thr Lys Gln Gln Thr Ser Val Met Arg Asn Ala Ser Ile Ala Lys
1               5                   10                  15

Glu Glu Arg Glu Gly Ser Asp Asn Asn Val Asp Arg Ser Ser Ser
            20                  25                  30

Asp Ala Ile Ser Asp Asn Asp Ala Glu Arg Ser Asn Ser His Ser Glu
        35                  40                  45

Ile Asp Asn Glu Ser Asn Phe Asp Met Val Pro Tyr Ser Arg Phe Ser
    50                  55                  60

His Lys Gln Lys Met Leu Leu Val Val Gln Cys Ala Phe Thr Gly Phe
65                  70                  75                  80

Phe Ser Thr Val Ala Gly Ser Ile Tyr Tyr Pro Val Leu Thr Ile Ile
                85                  90                  95

Glu Arg Lys Phe Asn Ile Thr Glu Glu Leu Ala Asn Val Thr Ile Val
            100                 105                 110

Val Tyr Phe Ile Phe Gln Gly Val Ala Pro Ser Ile Met Gly Gly Leu
        115                 120                 125

Ala Asp Thr Phe Gly Arg Arg Pro Ile Val Leu Trp Ala Ile Leu Ala
130                 135                 140

Tyr Phe Cys Ala Cys Ile Gly Leu Ala Cys His Asn Tyr Ala Gln
145                 150                 155                 160

Ile Leu Ala Leu Arg Cys Leu Gln Ala Ala Gly Ile Ser Pro Val Ile
                165                 170                 175

Ala Ile Asn Ser Gly Ile Met Gly Asp Val Thr Thr Lys Val Glu Arg
            180                 185                 190

Gly Gly Tyr Val Gly Leu Val Ala Gly Phe Gln Val Val Gly Thr Ala
        195                 200                 205

Phe Gly Ala Leu Ile Gly Ala Gly Leu Ser Ser Arg Trp Gly Trp Arg
    210                 215                 220

Ala Ile Phe Trp Phe Leu Ala Ile Gly Ser Gly Ile Cys Leu Val Phe
225                 230                 235                 240

Ser Thr Leu Leu Met Pro Glu Thr Lys Arg Thr Leu Val Gly Asn Gly
                245                 250                 255

Ser Val Thr Pro Arg Ser Phe Leu Asn Arg Ser Leu Ile Leu His Val
            260                 265                 270

Gly Ser Val Lys Lys Thr Leu His Leu Asp Asp Pro Asp Pro Glu Thr
        275                 280                 285

Leu Glu Pro Arg Thr Ser Val Asp Phe Leu Ala Pro Leu Lys Ile Leu
    290                 295                 300

His Ile Arg Glu Ile Asp Ile Leu Leu Ser Ile Ala Gly Leu Gln Phe
305                 310                 315                 320

Ser Thr Trp Thr Thr His Gln Thr Ala Leu Thr Ile Val Leu Ser Lys
                325                 330                 335

Lys Tyr Asn Leu Ser Val Ala Lys Ile Gly Leu Cys Phe Leu Pro Ala
            340                 345                 350

Gly Ile Ser Thr Leu Thr Ser Ile Ile Ser Ala Gly Arg Tyr Leu Asn
        355                 360                 365
```

```
Trp Ser Tyr Arg Thr Arg Lys Val Lys Tyr Asn Arg Trp Ile Lys Glu
            370                 375                 380

Gln Glu Leu Gln Leu Met Glu Lys Tyr Lys Gly Asp Lys Asn Lys Val
385                 390                 395                 400

Ala Glu Leu Ile His Ser Asn Ser His Tyr Thr Phe Asn Leu Val Glu
                405                 410                 415

Ala Arg Leu His Pro Ala Phe Val Thr Leu Leu Ser Ser Ile Gly
                420                 425                 430

Phe Thr Ala Phe Gly Trp Cys Ile Ser Val Lys Thr Pro Leu Ala Ala
                435                 440                 445

Val Leu Cys Thr Ser Ala Phe Ala Ser Leu Phe Ser Asn Cys Ile Leu
            450                 455                 460

Thr Phe Ser Thr Thr Leu Ile Val Asp Leu Phe Pro Ser Lys Ala Ser
465                 470                 475                 480

Thr Ala Thr Gly Cys Leu Asn Leu Phe Arg Cys Leu Leu Ser Ala Ile
                485                 490                 495

Phe Ile Ala Ala Leu Thr Lys Met Val Glu Lys Met Arg Tyr Gly Gly
                500                 505                 510

Val Phe Thr Phe Leu Ser Ala Ile Thr Ser Ser Ser Ser Leu Leu Leu
            515                 520                 525

Phe Tyr Leu Leu Lys Asn Gly Lys Gln Leu Ser Phe Asp Arg Ile Arg
            530                 535                 540

Ala Asn Asp Lys Ser Ala Gly Arg Ser Val Gly Lys Asn Ser Glu Lys
545                 550                 555                 560

Val Ser Thr

<210> SEQ ID NO 20
<211> LENGTH: 567
<212> TYPE: PRT
<213> ORGANISM: Saccharomyces cerevisiae

<400> SEQUENCE: 20

Met Ala Gly Ala Thr Ser Ser Ile Ile Arg Glu Asn Asp Phe Glu Asp
1               5                   10                  15

Glu Leu Ala Glu Ser Met Gln Ser Tyr Asn Arg Glu Thr Ala Asp Lys
                20                  25                  30

Leu Ala Leu Thr Arg Thr Glu Ser Val Lys Pro Glu Pro Glu Ile Thr
            35                  40                  45

Ala Pro Pro His Ser Arg Phe Ser Arg Ser Phe Lys Thr Val Leu Ile
50                  55                  60

Ala Gln Cys Ala Phe Thr Gly Phe Phe Ser Thr Ile Ala Gly Ala Ile
65                  70                  75                  80

Tyr Tyr Pro Val Leu Ser Val Ile Glu Arg Lys Phe Asp Ile Asp Glu
                85                  90                  95

Glu Leu Val Asn Val Thr Val Val Tyr Phe Val Phe Gln Gly Leu
                100                 105                 110

Ala Pro Thr Phe Met Gly Gly Phe Ala Asp Ser Leu Gly Arg Arg Pro
                115                 120                 125

Val Val Leu Val Ala Ile Val Ile Tyr Phe Gly Ala Cys Ile Gly Leu
            130                 135                 140

Ala Cys Ala Gln Thr Tyr Ala Gln Ile Ile Val Leu Arg Cys Leu Gln
145                 150                 155                 160

Ala Ala Gly Ile Ser Pro Val Ile Ala Ile Asn Ser Gly Ile Met Gly
                165                 170                 175
```

-continued

Asp Val Thr Thr Arg Ala Glu Arg Gly Gly Tyr Val Gly Tyr Val Ala
            180                 185                 190

Gly Phe Gln Val Leu Gly Ser Ala Phe Gly Ala Leu Ile Gly Ala Gly
        195                 200                 205

Leu Ser Ser Arg Trp Gly Trp Arg Ala Ile Phe Trp Phe Leu Ala Ile
210                 215                 220

Gly Ser Gly Ile Cys Phe Leu Ala Ser Phe Leu Ile Leu Pro Glu Thr
225                 230                 235                 240

Lys Arg Asn Ile Ser Gly Asn Gly Ser Val Thr Pro Lys Ser Tyr Leu
                245                 250                 255

Asn Arg Ala Pro Ile Leu Val Leu Pro Thr Val Arg Lys Ser Leu His
            260                 265                 270

Leu Asp Asn Pro Asp Tyr Glu Thr Leu Glu Leu Pro Thr Gln Leu Asn
        275                 280                 285

Leu Leu Ala Pro Phe Lys Ile Leu Lys Ala Tyr Glu Ile Cys Ile Leu
290                 295                 300

Met Leu Val Ala Gly Leu Gln Phe Ala Met Tyr Thr Thr His Leu Thr
305                 310                 315                 320

Ala Leu Ser Thr Ala Leu Ser Lys Gln Tyr His Leu Thr Val Ala Lys
                325                 330                 335

Val Gly Leu Cys Tyr Leu Pro Ser Gly Ile Cys Thr Leu Cys Ser Ile
            340                 345                 350

Val Ile Ala Gly Arg Tyr Leu Asn Trp Asn Tyr Arg Arg Leu Lys
        355                 360                 365

Tyr Tyr Gln Asn Trp Leu Gly Lys Lys Arg Ser Lys Leu Leu Glu Glu
370                 375                 380

His Asp Asn Asp Leu Asn Leu Val Gln Arg Ile Ile Glu Asn Asp Pro
385                 390                 395                 400

Lys Tyr Thr Phe Asn Ile Phe Lys Ala Arg Leu Gln Pro Ala Phe Val
                405                 410                 415

Thr Leu Leu Leu Ser Ser Ser Gly Phe Cys Ala Tyr Gly Trp Cys Ile
            420                 425                 430

Thr Val Lys Ala Pro Leu Ala Ala Val Leu Cys Met Ser Gly Phe Ala
        435                 440                 445

Ser Leu Phe Ser Asn Cys Ile Leu Thr Phe Ser Thr Thr Leu Ile Val
450                 455                 460

Asp Leu Phe Pro Thr Lys Thr Ser Thr Ala Thr Gly Cys Leu Asn Leu
465                 470                 475                 480

Phe Arg Cys Ile Leu Ser Ala Val Phe Ile Ala Ala Leu Ser Lys Met
                485                 490                 495

Val Glu Lys Met Lys Phe Gly Gly Val Phe Thr Phe Leu Gly Ala Leu
            500                 505                 510

Thr Ser Ser Ser Ser Ile Leu Leu Phe Ile Leu Leu Arg Lys Gly Lys
        515                 520                 525

Glu Leu Ala Phe Lys Arg Lys Gln Glu Leu Gly Val Asn Gln Glu
530                 535                 540

Val Lys Leu Leu Glu Ser Lys Glu Asn Val Pro Phe Asp Arg Ser Thr
545                 550                 555                 560

Thr Glu Lys Glu Glu Leu Val
                565

<210> SEQ ID NO 21
<211> LENGTH: 689
<212> TYPE: PRT

-continued

<213> ORGANISM: Saccharomyces cerevisiae

<400> SEQUENCE: 21

```
Met Gln Ala Gln Gly Ser Gln Ser Asn Val Gly Ser Leu Arg Ser Asn
1               5                   10                  15

Cys Ser Asp Asn Ser Leu Pro Asn Asn His Val Met Met His Cys Asp
            20                  25                  30

Glu Ser Ser Gly Ser Pro His Ser Glu His Asn Asp Tyr Ser Tyr Glu
        35                  40                  45

Lys Thr Asn Leu Glu Ser Thr Ala Ser Asn Ser Arg Glu His Arg Asp
    50                  55                  60

Asn Gln Leu Ser Arg Leu Lys Ser Glu Glu Tyr Val Val Pro Lys Asn
65                  70                  75                  80

Gln Arg Arg Gly Leu Leu Pro Gln Leu Ala Ile Ile Pro Glu Phe Lys
                85                  90                  95

Asp Ala Arg Asp Tyr Pro Pro Met Met Lys Lys Met Ile Val Phe Leu
            100                 105                 110

Ile Ala Phe Ser Ser Met Met Gly Pro Met Gly Thr Ser Ile Ile Phe
        115                 120                 125

Pro Ala Ile Asn Ser Ile Thr Thr Glu Phe Lys Thr Ser Val Ile Met
    130                 135                 140

Val Asn Val Ser Ile Gly Val Tyr Leu Leu Ser Leu Gly Val Phe Pro
145                 150                 155                 160

Leu Trp Trp Ser Ser Leu Ser Glu Leu Glu Gly Arg Arg Thr Thr Tyr
                165                 170                 175

Ile Thr Ser Phe Ala Leu Leu Phe Ala Phe Asn Ile Gly Ser Ala Leu
            180                 185                 190

Ala Pro Asp Ile Asn Ser Phe Ile Ala Leu Arg Met Leu Cys Gly Ala
        195                 200                 205

Ala Ser Ala Ser Val Gln Ser Val Gly Ala Gly Thr Val Ala Asp Leu
    210                 215                 220

Tyr Ile Ser Glu Asp Arg Gly Lys Asn Leu Ser Tyr Tyr Leu Gly
225                 230                 235                 240

Pro Leu Leu Ala Pro Leu Leu Ser Pro Ile Phe Gly Ser Leu Leu Val
                245                 250                 255

Asn Arg Trp Pro Trp Arg Ser Thr Gln Trp Phe Met Val Ile Leu Ser
            260                 265                 270

Gly Cys Asn Val Ile Leu Leu Thr Val Leu Leu Pro Glu Thr Leu Arg
        275                 280                 285

Lys Gln Asp Ser Lys Gly Ala Ile Ala Gln Ile Leu Ala Glu Arg Arg
    290                 295                 300

Ile Gln Val Asp Asn Asn Glu Arg Gly Glu Ile Gln Glu Asp Tyr Gln
305                 310                 315                 320

Arg Gly Glu Asp Glu Thr Asp Arg Ile Glu Asn Gln Val Ala Thr Leu
                325                 330                 335

Ser Thr Glu Lys His Asn Tyr Val Gly Val Arg Asp Gln Asp Ser
            340                 345                 350

Leu Asp Leu Glu Ser His Ser Ser Pro Asn Thr Tyr Asp Gly Arg Ala
        355                 360                 365

Gly Glu Thr Gln Leu Gln Arg Ile Tyr Thr Glu Ala Ser Arg Ser Leu
    370                 375                 380

Tyr Glu Tyr Gln Leu Asp Asp Ser Gly Ile Asp Ala Thr Thr Ala Gln
385                 390                 395                 400
```

-continued

Val Thr Arg Ile Arg Ser Thr Asp Pro Lys Leu Ala Arg Ser Ile Arg
            405                 410                 415

Glu Asn Ser Leu Arg Lys Leu Gln Thr Asn Leu Glu Glu Gln Val Lys
        420                 425                 430

Lys Val Leu Ser Ser Asn Gly Gly Glu Ile Ala Pro Lys Gln Val Ser
    435                 440                 445

Ala Val Arg Lys Val Trp Asp Thr Phe Phe Val Tyr Phe Ile Lys Pro
450                 455                 460

Leu Lys Ser Leu His Phe Leu Glu Tyr Pro Pro Val Ala Leu Ala Ile
465                 470                 475                 480

Thr Phe Ser Ala Ile Ser Phe Ser Thr Val Tyr Phe Val Asn Met Thr
                485                 490                 495

Val Glu Tyr Lys Tyr Ser Arg Pro Pro Tyr Asn Phe Lys Pro Leu Tyr
            500                 505                 510

Ile Gly Leu Leu Tyr Ile Pro Asn Ser Val Thr Tyr Phe Phe Ala Ser
        515                 520                 525

Ile Tyr Gly Gly Arg Trp Val Asp Met Leu Leu Lys Arg Tyr Lys Glu
    530                 535                 540

Lys Tyr Gly Ile Leu Ala Pro Glu Ala Arg Ile Ser Trp Asn Val Val
545                 550                 555                 560

Thr Ser Val Ile Ser Phe Pro Ile Ala Leu Leu Ile Phe Gly Trp Cys
                565                 570                 575

Leu Asp Lys Lys Cys His Trp Val Thr Pro Leu Ile Gly Thr Ala Leu
            580                 585                 590

Phe Gly Tyr Ala Ala Met Met Thr Ile Gly Ala Thr Leu Ser Tyr Leu
        595                 600                 605

Val Asp Ser Leu Pro Gly Lys Gly Ala Thr Gly Val Ala Leu Asn Asn
    610                 615                 620

Leu Ile Arg Gln Ile Leu Ala Ala Thr Ala Val Phe Val Thr Thr Pro
625                 630                 635                 640

Met Leu Asn Gly Met Gly Thr Gly Trp Ala Phe Thr Met Leu Ala Phe
                645                 650                 655

Ile Val Leu Gly Ala Ser Ser Val Leu Ile Ile Leu Lys Lys His Gly
            660                 665                 670

Asp Tyr Trp Arg Glu Asn Tyr Asp Leu Gln Lys Leu Tyr Asp Lys Ile
        675                 680                 685

Asp

<210> SEQ ID NO 22
<211> LENGTH: 586
<212> TYPE: PRT
<213> ORGANISM: Saccharomyces cerevisiae

<400> SEQUENCE: 22

Met Ser Asp His Ser Pro Ile Ser Asn Lys Glu Asn His Leu Leu Pro
1               5                   10                  15

Ser Asp Ser Ser Arg Ser Ser Ser Asp Met His Ser Thr Gly Thr
            20                  25                  30

Thr Gly Thr Thr Gly Val Glu Pro Val Asp Phe Thr Gly Glu Gly Ala
        35                  40                  45

Lys Tyr Thr Thr Ala Thr Glu Gly Asn Gly Gly Ala Asp Leu Ala Ile
    50                  55                  60

Gln Arg Thr Thr Thr Met Asn Ser Ala Ala Glu Ser Glu Val Asn Ile
65                  70                  75                  80

```
Thr Arg Arg Leu Thr Lys Ile Leu Thr Gly Ser Val Asn Glu Pro Asp
                85                  90                  95

Arg Val Glu Val Asp Tyr Thr Asn Cys Ala Pro Met Gly Gly Asp Arg
            100                 105                 110

Pro Tyr Pro Pro Ser Leu Pro Ser Arg Asp Leu Tyr Glu Val Thr Phe
        115                 120                 125

Asp Gly Pro Asn Asp Pro Leu His Pro Phe Asn Trp Pro Met Lys Lys
130                 135                 140

Lys Val Leu Leu Cys Leu Val Leu Cys Leu Asp Ser Ile Ala Ile Ala
145                 150                 155                 160

Met Cys Ser Ser Ile Phe Ala Ser Ala Val Pro Gln Ile Cys Glu Ile
                165                 170                 175

Tyr His Val Ile Glu Val Val Ala Ile Leu Gly Ile Thr Leu Phe Val
            180                 185                 190

Leu Gly Phe Ala Ala Ser Pro Val Ile Tyr Ala Pro Leu Ser Glu Leu
        195                 200                 205

Tyr Gly Arg Lys Gly Val Leu Val Leu Ser Ala Phe Gly Phe Ala Leu
210                 215                 220

Phe Gln Phe Ala Val Ala Thr Ala Glu Asn Leu Gln Thr Ile Phe Ile
225                 230                 235                 240

Cys Arg Phe Phe Gly Gly Phe Ile Gly Ala Ala Pro Met Ala Val Val
                245                 250                 255

Pro Ala Ala Phe Ala Asp Met Phe Asp Thr Asn Val Arg Gly Lys Ala
            260                 265                 270

Ile Ala Leu Phe Ser Leu Gly Val Phe Val Gly Pro Ile Leu Ser Pro
        275                 280                 285

Val Met Gly Ser Tyr Ile Ala Gln Arg Thr Thr Trp Arg Trp Leu Glu
290                 295                 300

Tyr Val Val Gly Cys Phe Ala Ser Ala Val Phe Val Ala Ile Val Leu
305                 310                 315                 320

Phe Phe Glu Glu Thr His His Pro Thr Ile Leu Val Asn Lys Ala Lys
                325                 330                 335

Gln Met Arg Lys Gln Ser Asn Asn Trp Gly Ile His Ala Ala His Glu
            340                 345                 350

Asp Val Glu Leu Ser Ile Lys Asp Ile Val Gln Lys Thr Val Thr Arg
        355                 360                 365

Pro Ile Ile Met Leu Phe Val Glu Pro Leu Leu Leu Phe Val Thr Ile
370                 375                 380

Tyr Asn Ser Phe Val Tyr Gly Ile Leu Tyr Leu Leu Leu Glu Ala Tyr
385                 390                 395                 400

Pro Leu Val Phe Val Glu Gly Tyr Gly Phe Thr Glu Asn Gly Glu Leu
                405                 410                 415

Pro Tyr Ile Ala Leu Ile Ile Gly Met Met Val Cys Ala Ala Phe Ile
            420                 425                 430

Trp Tyr Met Asp Asn Asp Tyr Leu Lys Arg Cys Arg Ala Lys Gly Lys
        435                 440                 445

Leu Val Pro Glu Ala Arg Leu Tyr Ala Met Val Ile Ala Gly Thr Val
450                 455                 460

Phe Pro Ile Gly Ile Leu Trp Phe Cys Trp Thr Gly Tyr Tyr Pro His
465                 470                 475                 480

Lys Ile His Trp Met Val Pro Thr Val Gly Gly Ala Phe Ile Gly Phe
                485                 490                 495

Gly Leu Met Gly Ile Phe Leu Pro Cys Leu Asn Tyr Ile Ile Glu Ser
```

```
                500                 505                 510
Tyr Leu Leu Leu Ala Ala Ser Ala Val Ala Ala Asn Thr Phe Met Arg
            515                 520                 525

Ser Ala Phe Gly Ala Cys Phe Pro Leu Phe Ala Gly Tyr Met Phe Arg
            530                 535                 540

Gly Met Gly Ile Gly Trp Ala Gly Leu Leu Leu Gly Leu Phe Ala Ala
545                 550                 555                 560

Ala Met Ile Pro Val Pro Leu Leu Phe Leu Lys Tyr Gly Glu Ser Ile
                565                 570                 575

Arg Lys Lys Ser Lys Tyr Ala Tyr Ala Ala
            580                 585

<210> SEQ ID NO 23
<211> LENGTH: 614
<212> TYPE: PRT
<213> ORGANISM: Saccharomyces cerevisiae

<400> SEQUENCE: 23

Met Ser Asp Gln Glu Ser Val Val Ser Phe Asn Ser Gln Asn Thr Ser
1               5                   10                  15

Met Val Asp Val Glu Gly Gln Gln Pro Gln Gln Tyr Val Pro Ser Lys
            20                  25                  30

Thr Asn Ser Arg Ala Asn Gln Leu Lys Leu Thr Lys Thr Glu Thr Val
        35                  40                  45

Lys Ser Leu Gln Asp Leu Gly Val Thr Ser Ala Ala Pro Val Pro Asp
    50                  55                  60

Ile Asn Ala Pro Gln Thr Ala Lys Asn Asn Ile Phe Pro Glu Glu Tyr
65                  70                  75                  80

Thr Met Glu Thr Pro Ser Gly Leu Val Pro Val Ala Thr Leu Gln Ser
                85                  90                  95

Met Gly Arg Thr Ala Ser Ala Leu Ser Arg Thr Arg Thr Lys Gln Leu
            100                 105                 110

Asn Arg Thr Ala Thr Asn Ser Ser Thr Gly Lys Glu Glu Met Glu
        115                 120                 125

Glu Glu Glu Thr Glu Glu Arg Glu Asp Gln Ser Gly Glu Asn Glu Leu
    130                 135                 140

Asp Pro Glu Ile Glu Phe Val Thr Phe Val Thr Gly Asp Pro Glu Asn
145                 150                 155                 160

Pro His Asn Trp Pro Ser Trp Val Arg Trp Ser Tyr Thr Val Leu Leu
                165                 170                 175

Ser Ile Leu Val Ile Cys Val Ala Tyr Gly Ser Ala Cys Ile Ser Gly
            180                 185                 190

Gly Leu Gly Thr Val Glu Lys Lys Tyr His Val Gly Met Glu Ala Ala
        195                 200                 205

Ile Leu Ser Cys Ser Leu Met Val Ile Gly Phe Ser Leu Gly Pro Leu
    210                 215                 220

Ile Trp Ser Pro Val Ser Asp Leu Tyr Gly Arg Arg Val Ala Tyr Phe
225                 230                 235                 240

Val Ser Met Gly Leu Tyr Val Ile Phe Asn Ile Pro Cys Ala Leu Ala
                245                 250                 255

Pro Asn Leu Gly Cys Leu Leu Ala Cys Arg Phe Leu Cys Gly Val Trp
            260                 265                 270

Ser Ser Ser Gly Leu Cys Leu Val Gly Gly Ser Ile Ala Asp Met Phe
        275                 280                 285
```

```
Pro Ser Glu Thr Arg Gly Lys Ala Ile Ala Phe Phe Ala Phe Ala Pro
    290                 295                 300

Tyr Val Gly Pro Val Ile Gly Pro Leu Val Asn Gly Phe Ile Ser Val
305                 310                 315                 320

Ser Thr Gly Arg Met Asp Leu Ile Phe Trp Val Asn Met Ala Phe Ala
                325                 330                 335

Gly Val Met Trp Ile Ile Ser Ser Ala Ile Pro Glu Thr Tyr Ala Pro
                340                 345                 350

Val Ile Leu Lys Arg Lys Ala Ala Arg Leu Arg Lys Glu Thr Gly Asn
                355                 360                 365

Pro Lys Ile Met Thr Glu Gln Glu Ala Gln Gly Val Ser Met Ser Glu
    370                 375                 380

Met Met Arg Ala Cys Leu Leu Arg Pro Leu Tyr Phe Ala Val Thr Glu
385                 390                 395                 400

Pro Val Leu Val Ala Thr Cys Phe Tyr Val Cys Leu Ile Tyr Ser Leu
                405                 410                 415

Leu Tyr Ala Phe Phe Phe Ala Pro Val Ile Phe Gly Glu Leu Tyr
                420                 425                 430

Gly Tyr Lys Asp Asn Leu Val Gly Leu Met Phe Ile Pro Ile Val Ile
            435                 440                 445

Gly Ala Leu Trp Ala Leu Ala Thr Thr Phe Tyr Cys Glu Asn Lys Tyr
    450                 455                 460

Leu Gln Ile Val Lys Gln Arg Lys Pro Thr Pro Glu Asp Arg Leu Leu
465                 470                 475                 480

Gly Ala Lys Ile Gly Ala Pro Phe Ala Ala Ile Ala Leu Trp Ile Leu
                485                 490                 495

Gly Ala Thr Ala Tyr Lys His Ile Ile Trp Val Gly Pro Ala Ser Ala
                500                 505                 510

Gly Leu Ala Phe Gly Phe Gly Met Val Leu Ile Tyr Tyr Ser Leu Asn
            515                 520                 525

Asn Tyr Ile Ile Asp Cys Tyr Val Gln Tyr Ala Ser Ser Ala Leu Ala
    530                 535                 540

Thr Lys Val Phe Leu Arg Ser Ala Gly Gly Ala Ala Phe Pro Leu Phe
545                 550                 555                 560

Thr Ile Gln Met Tyr His Lys Leu Asn Leu His Trp Gly Ser Trp Leu
                565                 570                 575

Leu Ala Phe Ile Ser Thr Ala Met Ile Ala Leu Pro Phe Ala Phe Ser
                580                 585                 590

Tyr Trp Gly Lys Gly Leu Arg His Lys Leu Ser Lys Lys Asp Tyr Ser
    595                 600                 605

Ile Asp Ser Val Glu Met
    610

<210> SEQ ID NO 24
<211> LENGTH: 622
<212> TYPE: PRT
<213> ORGANISM: Saccharomyces cerevisiae

<400> SEQUENCE: 24

Met Asn Arg Gln Glu Ser Ile Asn Ser Phe Asn Ser Asp Glu Thr Ser
1               5                   10                  15

Ser Leu Ser Asp Val Glu Ser Gln Gln Pro Gln Gln Tyr Ile Pro Ser
            20                  25                  30

Glu Ser Gly Ser Lys Ser Asn Met Ala Pro Asn Gln Leu Lys Leu Thr
        35                  40                  45
```

-continued

```
Arg Thr Glu Thr Val Lys Ser Leu Gln Asp Met Gly Val Ser Ser Lys
 50                  55                  60
Ala Pro Val Pro Asp Val Asn Ala Pro Gln Ser Ser Lys Asn Lys Ile
 65                  70                  75                  80
Phe Pro Glu Glu Tyr Thr Leu Glu Thr Pro Thr Gly Leu Val Pro Val
                 85                  90                  95
Ala Thr Leu His Ser Ile Gly Arg Thr Ser Thr Ala Ile Ser Arg Thr
                100                 105                 110
Arg Thr Arg Gln Ile Asp Gly Ala Ser Ser Pro Ser Ser Asn Glu Asp
                115                 120                 125
Ala Leu Glu Ser Asp Asn Asn Glu Lys Gly Lys Glu Gly Asp Ser Ser
130                 135                 140
Gly Ala Asn Asp Glu Ala Pro Asp Leu Asp Pro Glu Ile Glu Phe Val
145                 150                 155                 160
Thr Phe Val Thr Gly Asp Pro Glu Asn Pro His Asn Trp Pro Ala Trp
                165                 170                 175
Ile Arg Trp Ser Tyr Thr Val Leu Leu Ser Ile Leu Val Ile Cys Val
                180                 185                 190
Ala Tyr Gly Ser Ala Cys Ile Ser Gly Gly Leu Gly Thr Val Glu Lys
                195                 200                 205
Lys Tyr His Val Gly Met Glu Ala Ala Ile Leu Ser Val Ser Leu Met
210                 215                 220
Val Ile Gly Phe Ser Leu Gly Pro Leu Ile Trp Ser Pro Val Ser Asp
225                 230                 235                 240
Leu Tyr Gly Arg Arg Val Ala Tyr Phe Val Ser Met Gly Leu Tyr Val
                245                 250                 255
Ile Phe Asn Ile Pro Cys Ala Leu Ala Pro Asn Leu Gly Ser Leu Leu
                260                 265                 270
Ala Cys Arg Phe Leu Cys Gly Val Trp Ser Ser Ser Gly Leu Cys Leu
                275                 280                 285
Val Gly Gly Ser Ile Ala Asp Met Phe Pro Ser Glu Thr Arg Gly Lys
290                 295                 300
Ala Ile Ala Phe Phe Ala Phe Ala Pro Tyr Val Gly Pro Val Val Gly
305                 310                 315                 320
Pro Leu Val Asn Gly Phe Ile Ser Val Ser Thr Gly Arg Met Asp Leu
                325                 330                 335
Ile Phe Trp Val Asn Met Ala Phe Ala Gly Val Met Trp Ile Ile Ser
                340                 345                 350
Ser Ala Ile Pro Glu Thr Tyr Ala Pro Val Ile Leu Lys Arg Lys Ala
                355                 360                 365
Ala Arg Leu Arg Lys Glu Thr Gly Asn Pro Lys Ile Met Thr Glu Gln
370                 375                 380
Glu Ala Gln Gly Val Ser Met Gly Glu Met Met Arg Ala Cys Leu Leu
385                 390                 395                 400
Arg Pro Leu Tyr Phe Ser Val Thr Glu Pro Val Leu Val Ala Thr Cys
                405                 410                 415
Phe Tyr Val Cys Leu Ile Tyr Ser Leu Leu Tyr Ala Phe Phe Phe Ala
                420                 425                 430
Phe Pro Val Ile Phe Gly Glu Leu Tyr Gly Tyr Lys Asp Asn Leu Val
                435                 440                 445
Gly Leu Met Phe Ile Pro Ile Val Ile Gly Ala Leu Trp Ala Leu Ala
450                 455                 460
```

```
Thr Thr Phe Tyr Cys Glu Asn Lys Tyr Leu Gln Ile Val Lys Gln Arg
465                 470                 475                 480

Lys Pro Thr Pro Glu Asp Arg Leu Leu Gly Ala Lys Ile Gly Ala Pro
            485                 490                 495

Phe Ala Ala Ile Ala Leu Trp Ile Leu Gly Ala Thr Ala Tyr Lys His
            500                 505                 510

Ile Ile Trp Val Gly Pro Ala Ser Ala Gly Leu Ala Phe Gly Phe Gly
            515                 520                 525

Met Val Leu Ile Tyr Tyr Ser Leu Asn Asn Tyr Ile Ile Asp Cys Tyr
            530                 535                 540

Val Gln Tyr Ala Ser Ser Ala Leu Ala Thr Lys Val Phe Leu Arg Ser
545                 550                 555                 560

Ala Gly Gly Ala Ala Phe Pro Leu Phe Thr Ile Gln Met Tyr His Lys
            565                 570                 575

Leu Asn Leu His Trp Gly Ser Trp Leu Leu Ala Phe Ile Ser Thr Ala
            580                 585                 590

Met Ile Ala Leu Pro Phe Ala Phe Ser Tyr Trp Gly Lys Gly Leu Arg
            595                 600                 605

His Lys Leu Ser Lys Lys Asp Tyr Ser Ile Asp Ser Ile Glu
    610                 615                 620

<210> SEQ ID NO 25
<211> LENGTH: 659
<212> TYPE: PRT
<213> ORGANISM: Saccharomyces cerevisiae

<400> SEQUENCE: 25

Met Pro Ser Ser Leu Thr Lys Thr Glu Ser Asn Ser Asp Pro Arg Thr
1               5                   10                  15

Asn Ile Gln Gln Val Pro Lys Ala Leu Asp Lys Asn Val Thr Asn Ser
            20                  25                  30

Gly Asn Leu Asp Ser Thr Ser Ser Thr Gly Ser Ile Thr Glu Asp
        35                  40                  45

Glu Lys Arg Ser Glu Pro Asn Ala Asp Ser Asn Asn Met Thr Gly Gly
50                  55                  60

Glu Pro Ile Asp Pro Arg Asp Leu Asp Trp Asp Gly Pro Asp Asp Pro
65                  70                  75                  80

Asp Asn Pro His Asn Trp Ser Ser Leu Lys Lys Trp Tyr Thr Thr Met
                85                  90                  95

Thr Ser Ala Phe Leu Cys Leu Val Val Thr Met Gly Ser Ser Leu Tyr
            100                 105                 110

Val Ser Ser Val Pro Glu Leu Val Glu Arg Tyr His Val Ser Gln Thr
            115                 120                 125

Leu Ala Leu Ala Gly Leu Thr Phe Tyr Leu Gly Leu Ser Thr Val
        130                 135                 140

Ile Gly Ala Pro Leu Ser Glu Val Phe Gly Arg Lys Pro Val Tyr Leu
145                 150                 155                 160

Phe Ser Leu Pro Val Ser Met Leu Phe Thr Met Gly Val Gly Leu Ser
                165                 170                 175

Asn Gly His Met Arg Ile Ile Leu Pro Leu Arg Phe Leu Ser Gly Val
            180                 185                 190

Phe Ala Ser Pro Ala Leu Ser Val Gly Ser Gly Thr Ile Leu Asp Ile
            195                 200                 205

Phe Asp Val Asp Gln Val Ser Val Ala Met Thr Tyr Phe Val Leu Ser
            210                 215                 220
```

```
Pro Phe Leu Gly Pro Val Leu Ser Pro Ile Met Ala Gly Phe Ala Thr
225                 230                 235                 240

Glu Ala Lys Gly Trp Arg Trp Ser Glu Trp Ile Gln Leu Ile Ala Gly
            245                 250                 255

Gly Leu Ile Leu Pro Phe Ile Ala Leu Met Pro Glu Thr His Lys Gly
            260                 265                 270

Ile Ile Leu Arg Lys Arg Ala Lys Arg Asn Ile Ala Leu Lys Lys
        275                 280                 285

Phe Ser Arg Glu Ala Gln Lys Glu Phe Leu Lys Thr Thr Val Thr Ile
    290                 295                 300

Thr Ile Leu Arg Pro Leu Lys Met Leu Val Val Glu Pro Ile Val Phe
305                 310                 315                 320

Val Phe Ser Val Tyr Val Ala Phe Ile Phe Ala Ile Leu Phe Gly Phe
                325                 330                 335

Phe Glu Ala Tyr Ala Val Ile Tyr Arg Gly Val Tyr His Met Ser Met
            340                 345                 350

Gly Ile Ser Gly Leu Pro Phe Ile Gly Ile Gly Val Gly Leu Trp Ile
        355                 360                 365

Gly Ala Phe Phe Tyr Leu Tyr Ile Asp Arg Lys Tyr Leu Phe Pro Lys
370                 375                 380

Pro Pro Ala Gly Thr Gln Pro Leu Thr Glu Lys Glu Arg Thr Ser Lys
385                 390                 395                 400

Arg Thr Thr Pro Tyr Arg Gly Ala Arg Asp Ala Glu Thr Gly Glu Leu
                405                 410                 415

Leu Pro Val Val Pro Glu Lys Phe Leu Ile Ala Cys Lys Phe Gly Ser
                420                 425                 430

Val Ala Leu Pro Ile Gly Leu Phe Trp Gln Ala Trp Thr Ala Arg Ser
            435                 440                 445

Asp Val His Trp Met Ala Pro Val Ala Gly Val Pro Phe Gly Phe
    450                 455                 460

Gly Leu Ile Leu Ile Phe Phe Ser Val Leu Met Tyr Phe Ser Thr Cys
465                 470                 475                 480

Tyr Pro Pro Leu Thr Val Ala Ser Cys Leu Ala Ala Asn Asn Leu Leu
                485                 490                 495

Arg Tyr Val Met Ser Ser Val Phe Pro Leu Phe Thr Ile Gln Met Tyr
                500                 505                 510

Thr Lys Met Lys Ile Lys Trp Ala Ser Thr Leu Phe Ala Leu Val Cys
            515                 520                 525

Val Val Met Ile Pro Ile Pro Trp Val Phe Glu Lys Trp Gly Ser Lys
530                 535                 540

Leu Arg His Lys Ser Gln Phe Gly Tyr Ala Ala Met Glu Lys Glu Ala
545                 550                 555                 560

Glu Thr Glu Gly Gly Ile Asp Asp Val Asn Ala Val Asp Gly Glu Leu
                565                 570                 575

Asn Leu Thr Arg Met Thr Thr Leu Arg Thr Met Glu Thr Asp Pro Ser
            580                 585                 590

Thr Arg Glu Lys Pro Gly Glu Arg Leu Ser Leu Arg Arg Thr His Thr
            595                 600                 605

Gln Pro Val Pro Ala Ser Phe Asp Arg Glu Asp Gly Gln His Ala Gln
    610                 615                 620

Asn Arg Asn Glu Pro Ile Ser Asn Ser Leu Tyr Ser Ala Ile Lys Asp
625                 630                 635                 640
```

-continued

Asn Glu Asp Gly Tyr Ser Tyr Thr Glu Met Ala Thr Asp Ala Ser Ala
                645                 650                 655

Arg Met Val

<210> SEQ ID NO 26
<211> LENGTH: 514
<212> TYPE: PRT
<213> ORGANISM: Saccharomyces cerevisiae

<400> SEQUENCE: 26

Met Val Ala Glu Phe Gln Ile Ala Ser Ala Gln Ser Ser Ala Leu Thr
1               5                   10                  15

Ser Thr Glu Glu His Cys Ser Ile Asn Ser Asp Lys Ala Ala Lys
            20                  25                  30

Leu Asp Leu Glu Leu Thr Ser Glu Arg Lys Asn Asp Gly Lys Gln Ser
            35                  40                  45

His Glu Val Thr Phe Asn Glu Asp Ile Ala Asp Pro Glu Asp Ile Ala
        50                  55                  60

Arg His Met Ser Thr Ala Arg Arg Tyr Tyr Ile Ser Ser Leu Ile Thr
65                  70                  75                  80

Phe Thr Ser Met Val Ile Thr Met Ile Ser Ser Trp Thr Leu Pro
                85                  90                  95

Ser Thr His Ile Ile Glu His Phe His Ile Ser His Glu Val Ser Thr
            100                 105                 110

Leu Gly Ile Thr Leu Tyr Val Phe Gly Leu Gly Ile Gly Pro Leu Phe
        115                 120                 125

Leu Ser Pro Leu Ser Glu Leu Tyr Gly Arg Arg Ile Thr Phe Leu Tyr
    130                 135                 140

Ala Leu Thr Leu Ser Ile Ile Trp Gln Cys Leu Thr Ile Trp Ser Lys
145                 150                 155                 160

Thr Ile Thr Gly Val Met Phe Gly Arg Phe Leu Ser Gly Phe Gly
                165                 170                 175

Ser Ala Phe Leu Ser Val Ala Gly Gly Ala Ile Ala Asp Ile Phe Asp
            180                 185                 190

Lys Asp Gln Ile Gly Ile Pro Met Ala Ile Tyr Thr Thr Ser Ala Phe
        195                 200                 205

Leu Gly Pro Ser Leu Gly Pro Ile Ile Gly Gly Ala Leu Tyr His Gln
    210                 215                 220

Ser Tyr Lys Trp Thr Phe Ile Thr Leu Leu Ile Thr Ser Gly Cys Cys
225                 230                 235                 240

Leu Val Met Ile Ile Phe Thr Ile Pro Glu Thr Tyr Lys Pro Met Leu
                245                 250                 255

Leu Ile Arg Lys Ala Lys Arg Leu Arg Lys Glu Lys Asn Asp Gln Arg
            260                 265                 270

Tyr Tyr Ala Val Leu Glu Val Thr Arg Glu Gln Thr Ser Leu Leu Ser
        275                 280                 285

Ala Ile Phe Leu Ser Thr Lys Arg Pro Phe Gly Leu Leu Arg Asp
    290                 295                 300

Arg Met Met Gly Val Leu Cys Phe Tyr Thr Gly Leu Glu Leu Ala Ile
305                 310                 315                 320

Ile Tyr Leu Tyr Phe Val Ala Phe Pro Tyr Val Phe Lys Lys Leu Tyr
                325                 330                 335

Asn Phe Gly Pro Met Glu Ile Ala Cys Ser Tyr Ile Gly Ile Met Val
            340                 345                 350

```
Gly Met Ile Leu Ser Ala Pro Thr Cys Leu Leu Phe Gln Lys Thr Phe
            355                 360                 365

Glu Trp Arg Val Lys Arg Asn Asn Gly Val Lys Thr Pro Glu Met Arg
    370                 375                 380

Phe Glu Pro Leu Phe Tyr Gly Ala Phe Leu Thr Pro Val Gly Leu Phe
385                 390                 395                 400

Ile Phe Ala Phe Thr Cys Tyr Lys His Val His Trp Ile Ala Pro Ile
                405                 410                 415

Ile Gly Ser Ala Ile Phe Gly Ser Val Tyr Val Phe Thr Gly
            420                 425                 430

Val Phe Ala Tyr Thr Val Asp Ala Tyr Arg Arg Tyr Ala Ala Ser Gly
    435                 440                 445

Met Ala Cys Asn Thr Phe Val Arg Cys Ile Met Ala Gly Val Phe Pro
450                 455                 460

Leu Phe Gly Leu Gln Met Tyr Lys Ser Met Gly Val Asn Trp Ala Gly
465                 470                 475                 480

Phe Leu Leu Ala Met Val Thr Val Ala Met Ile Pro Val Pro Phe Leu
                485                 490                 495

Phe Thr Lys Tyr Gly Ala Arg Leu Arg Ala Lys Ser Pro Tyr Ala Trp
            500                 505                 510

Asp Asp

<210> SEQ ID NO 27
<211> LENGTH: 542
<212> TYPE: PRT
<213> ORGANISM: Saccharomyces cerevisiae

<400> SEQUENCE: 27

Met Gly Asn Gln Ser Leu Val Val Leu Thr Glu Ser Lys Gly Glu Tyr
1               5                   10                  15

Glu Asn Glu Thr Glu Leu Pro Val Lys Lys Ser Ser Arg Asp Asn Asn
            20                  25                  30

Ile Gly Glu Ser Leu Thr Ala Thr Ala Phe Thr Gln Ser Glu Asp Glu
        35                  40                  45

Met Val Asp Ser Asn Gln Lys Trp Gln Asn Pro Asn Tyr Phe Lys Tyr
    50                  55                  60

Ala Trp Gln Glu Tyr Leu Phe Ile Phe Thr Cys Met Ile Ser Gln Leu
65                  70                  75                  80

Leu Asn Gln Ala Gly Thr Thr Gln Thr Leu Ser Ile Met Asn Ile Leu
                85                  90                  95

Ser Asp Ser Phe Gly Ser Glu Gly Asn Ser Lys Ser Trp Leu Met Ala
            100                 105                 110

Ser Phe Pro Leu Val Ser Gly Ser Phe Ile Leu Ile Ser Gly Arg Leu
        115                 120                 125

Gly Asp Ile Tyr Gly Leu Lys Lys Met Leu Leu Val Gly Tyr Val Leu
    130                 135                 140

Val Ile Ile Trp Ser Leu Ile Cys Gly Ile Thr Lys Tyr Ser Gly Ser
145                 150                 155                 160

Asp Thr Phe Phe Ile Ile Ser Arg Ala Phe Gln Gly Leu Gly Ile Ala
                165                 170                 175

Phe Val Leu Pro Asn Val Leu Gly Ile Ile Gly Asn Ile Tyr Val Gly
            180                 185                 190

Gly Thr Phe Arg Lys Asn Ile Val Ile Ser Phe Val Gly Ala Met Ala
        195                 200                 205
```

```
Pro Ile Gly Ala Thr Leu Gly Cys Leu Phe Ala Gly Leu Ile Gly Thr
    210                 215                 220

Glu Asp Pro Lys Gln Trp Pro Trp Ala Phe Tyr Ala Tyr Ser Ile Ala
225                 230                 235                 240

Ala Phe Ile Asn Phe Val Leu Ser Ile Tyr Ala Ile Pro Ser Thr Ile
                245                 250                 255

Pro Thr Asn Ile His His Phe Ser Met Asp Trp Ile Gly Ser Val Leu
            260                 265                 270

Gly Val Ile Gly Leu Ile Leu Asn Phe Val Trp Asn Gln Ala Pro
        275                 280                 285

Ile Ser Gly Trp Asn Gln Ala Tyr Ile Ile Val Ile Leu Ile Ile Ser
    290                 295                 300

Val Ile Phe Leu Val Val Phe Ile Ile Tyr Glu Ile Arg Phe Ala Lys
305                 310                 315                 320

Thr Pro Leu Leu Pro Arg Ala Val Ile Lys Asp Arg His Met Ile Gln
                325                 330                 335

Ile Met Leu Ala Leu Phe Phe Gly Trp Gly Ser Phe Gly Ile Phe Thr
            340                 345                 350

Phe Tyr Tyr Phe Gln Phe Gln Leu Asn Ile Arg Gln Tyr Thr Ala Leu
        355                 360                 365

Trp Ala Gly Gly Thr Tyr Phe Met Phe Leu Ile Trp Gly Ile Ile Ala
    370                 375                 380

Ala Leu Leu Val Gly Phe Thr Ile Lys Asn Val Ser Pro Ser Val Phe
385                 390                 395                 400

Leu Phe Phe Ser Met Val Ala Phe Asn Val Gly Ser Ile Met Ala Ser
                405                 410                 415

Val Thr Pro Val His Glu Thr Tyr Phe Arg Thr Gln Leu Gly Thr Met
            420                 425                 430

Ile Ile Leu Ser Phe Gly Met Asp Leu Ser Phe Pro Ala Ser Ser Ile
        435                 440                 445

Ile Phe Ser Asp Asn Leu Pro Met Glu Tyr Gln Gly Met Ala Gly Ser
    450                 455                 460

Leu Val Asn Thr Val Val Asn Tyr Ser Met Ser Leu Cys Leu Gly Met
465                 470                 475                 480

Gly Ala Thr Val Glu Thr Gln Val Asn Ser Asp Gly Lys His Leu Leu
                485                 490                 495

Lys Gly Tyr Arg Gly Ala Gln Tyr Leu Gly Ile Gly Leu Ala Ser Leu
            500                 505                 510

Ala Cys Met Ile Ser Gly Leu Tyr Met Val Glu Ser Phe Ile Lys Gly
        515                 520                 525

Arg Arg Ala Arg Ala Ala Glu Tyr Asp Cys Thr Val Ala
    530                 535                 540

<210> SEQ ID NO 28
<211> LENGTH: 615
<212> TYPE: PRT
<213> ORGANISM: Saccharomyces cerevisiae

<400> SEQUENCE: 28

Met Ser Ser Ser Val Val Gly Ser Ser Asn Lys Lys Ser Gly Ile
1               5                   10                  15

Arg Gln Ser Cys Glu Ile Ile Glu Arg Glu His Ser Asn Asp Asp
                20                  25                  30

Thr Tyr Ser Met Thr Ser Thr Phe Lys Leu Lys Glu Asn Glu Ile
            35                  40                  45
```

```
Met Ser Ala Gln Phe Asp Ser Leu Lys Tyr Lys Ile Leu Leu Ile Ser
 50                  55                  60

Thr Ala Phe Val Cys Gly Phe Gly Ile Ser Leu Asp Tyr Thr Leu Arg
 65                  70                  75                  80

Ser Thr Tyr Thr Gly Tyr Ala Thr Asn Ser Tyr Ser Glu His Ser Leu
                 85                  90                  95

Leu Ser Thr Val Gln Val Ile Asn Ala Val Val Ser Val Gly Ser Gln
                100                 105                 110

Val Val Tyr Ser Arg Leu Ser Asp His Phe Gly Arg Leu Arg Leu Phe
            115                 120                 125

Leu Val Ala Thr Ile Phe Tyr Ile Met Gly Thr Ile Ile Gln Ser Gln
        130                 135                 140

Ala Thr Arg Leu Thr Met Tyr Ala Ala Gly Ser Val Phe Tyr Asn Cys
145                 150                 155                 160

Gly Tyr Val Gly Thr Asn Leu Leu Thr Leu Ile Leu Ser Asp Phe
                165                 170                 175

Ser Ser Leu Lys Trp Arg Met Phe Tyr Gln Tyr Ala Ser Tyr Trp Pro
            180                 185                 190

Tyr Ile Ile Ile Pro Trp Ile Ser Gly Asn Ile Ile Thr Ala Ala Asn
            195                 200                 205

Pro Gln Lys Asn Trp Ser Trp Asn Ile Ala Met Trp Ala Phe Ile Tyr
        210                 215                 220

Pro Leu Ser Ala Leu Pro Ile Ile Phe Leu Ile Leu Tyr Met Lys Tyr
225                 230                 235                 240

Lys Ser Ser Lys Thr Ala Glu Trp Arg Ser Leu Lys Glu Gln Ala Arg
                245                 250                 255

Lys Glu Arg Thr Gly Gly Leu Phe Glu Asn Leu Val Phe Leu Phe Trp
            260                 265                 270

Lys Leu Asp Ile Val Gly Ile Leu Leu Ile Thr Val Ser Leu Gly Cys
        275                 280                 285

Ile Leu Val Pro Leu Thr Leu Ala Asn Glu Thr Ser Gln Lys Trp His
290                 295                 300

Asn Ser Lys Ile Ile Ala Thr Leu Val Ser Gly Gly Cys Leu Phe Phe
305                 310                 315                 320

Ile Phe Leu Tyr Trp Glu Ala Lys Phe Ala Lys Ser Pro Leu Leu Pro
                325                 330                 335

Phe Lys Leu Leu Ser Asp Arg Gly Ile Trp Ala Pro Leu Gly Val Thr
            340                 345                 350

Phe Phe Asn Phe Phe Thr Phe Phe Ile Ser Cys Asp Tyr Leu Tyr Pro
        355                 360                 365

Val Leu Leu Val Ser Met Lys Glu Ser Ser Thr Ser Ala Ala Arg Ile
        370                 375                 380

Val Asn Leu Pro Asp Phe Val Ala Ala Thr Ala Ser Pro Phe Tyr Ser
385                 390                 395                 400

Leu Leu Val Ala Lys Thr Arg Lys Leu Lys Leu Ser Val Ile Gly Gly
                405                 410                 415

Cys Ala Ala Trp Met Val Cys Met Gly Leu Phe Tyr Lys Tyr Arg Gly
            420                 425                 430

Gly Ser Gly Ser His Glu Gly Val Ile Ala Ala Ser Val Ile Met Gly
        435                 440                 445

Leu Ser Gly Leu Leu Cys Ser Asn Ser Val Ile Val Ile Leu Gln Ala
    450                 455                 460
```

```
Met Thr Thr His Ser Arg Met Ala Val Ile Thr Gly Ile Gln Tyr Thr
465                 470                 475                 480

Phe Ser Lys Leu Gly Ala Ala Ile Gly Ala Ser Val Ser Gly Ala Ile
            485                 490                 495

Trp Thr Gln Thr Met Pro Asn Gln Leu Tyr Lys Asn Leu Gly Asn Asp
        500                 505                 510

Thr Leu Ala Glu Ile Ala Tyr Ala Ser Pro Tyr Thr Phe Ile Ser Asp
        515                 520                 525

Tyr Pro Trp Gly Ser Pro Glu Arg Asp Ala Val Val Glu Ser Tyr Arg
    530                 535                 540

Tyr Val Gln Arg Ile Ile Met Thr Val Gly Leu Ala Cys Thr Val Pro
545                 550                 555                 560

Phe Phe Ala Phe Thr Met Phe Met Arg Asp Pro Glu Leu Ile Asp Lys
                565                 570                 575

Ala Thr His Glu Glu Phe Thr Glu Asp Gly Leu Val Val Leu Pro Asp
            580                 585                 590

Glu Glu Asn Ile Phe Ser Gln Ile Lys Ala Leu Phe Arg His Asn Arg
            595                 600                 605

Ser Asn Lys Lys Leu Gly Cys
            610                 615

<210> SEQ ID NO 29
<211> LENGTH: 613
<212> TYPE: PRT
<213> ORGANISM: Saccharomyces cerevisiae

<400> SEQUENCE: 29

Met Lys Gly Glu Pro Lys Thr Tyr Ser Met Ser Asp Leu Ser Tyr Tyr
1               5                   10                  15

Gly Glu Lys Ala Gln Gln Asn Glu Lys Gln Lys Gln Tyr Val
            20                  25                  30

Val Arg Arg Asn Ser Thr Gln Ser Thr Ser Lys Gln Asn Val Ser Val
            35                  40                  45

Val Leu Glu Asp Asn Ala Ser Glu Ser Asn Glu Leu Pro Lys Gly Phe
50                  55                  60

Ile Leu Tyr Ala Ser Leu Ile Ala Leu Ala Leu Ser Leu Phe Leu Ala
65                  70                  75                  80

Ala Leu Asp Ile Met Ile Val Ser Thr Ile Glu Glu Val Ala Lys
            85                  90                  95

Gln Phe Gly Ser Tyr Ser Glu Ile Gly Trp Leu Phe Thr Gly Tyr Ser
            100                 105                 110

Leu Pro Asn Ala Leu Leu Ala Leu Ile Trp Gly Arg Ile Ala Thr Pro
            115                 120                 125

Ile Gly Phe Lys Glu Thr Met Leu Phe Ala Ile Val Ile Phe Glu Ile
    130                 135                 140

Gly Ser Leu Ile Ser Ala Leu Ala Asn Ser Met Ser Met Leu Ile Gly
145                 150                 155                 160

Gly Arg Val Ile Ala Gly Val Gly Cys Gly Ile Gln Ser Leu Ser
            165                 170                 175

Phe Val Ile Gly Ser Thr Leu Val Glu Glu Ser Gln Arg Gly Ile Leu
            180                 185                 190

Ile Ala Val Leu Ser Cys Ser Phe Ala Ile Ala Ser Val Val Gly Pro
    195                 200                 205

Phe Leu Gly Gly Val Phe Thr Ser Ser Val Thr Trp Arg Trp Cys Phe
    210                 215                 220
```

Tyr Val Asn Leu Pro Ile Gly Gly Leu Ala Phe Phe Leu Phe Leu Phe
225                 230                 235                 240

Phe Tyr Asn Pro Gly Leu Ser Thr Phe Gln Glu Thr Met Asp Asn Ile
            245                 250                 255

Arg Lys Phe Pro Ser Gln Phe Ile Glu Ile Val Arg Asn Val Ala Tyr
        260                 265                 270

His Leu Leu Lys Ile Lys Gly Phe Ser Lys Leu Asn Gly Trp Arg Lys
    275                 280                 285

Pro Phe Met Glu Leu Ile Phe Met Tyr Asp Ile Ile Glu Phe Val Phe
290                 295                 300

Cys Ser Ala Gly Phe Thr Cys Ile Leu Leu Ala Phe Thr Phe Gly Gly
305                 310                 315                 320

Asn Arg Tyr Ala Trp Asn Ser Ala Ser Ile Ile Ile Leu Phe Ile Ile
            325                 330                 335

Gly Ile Val Leu Val Leu Ala Gly Ile Tyr Asp Phe Leu Val Phe
        340                 345                 350

Pro Lys Phe Asn Ile Val Lys Ala Thr Pro His Tyr Gln Pro Leu Met
        355                 360                 365

Ser Trp Thr Asn Ile Lys Lys Pro Gly Ile Phe Thr Val Asn Ile Ala
370                 375                 380

Leu Phe Leu Thr Cys Ala Gly Tyr Ile Ser Gln Phe Thr Tyr Ile Val
385                 390                 395                 400

Gln Tyr Phe Gln Leu Ile Tyr Asn Asp Ser Ala Trp Arg Ala Ala Val
            405                 410                 415

His Leu Val Ala Cys Ile Ile Ser Thr Val Val Thr Ala Ile Leu Cys
            420                 425                 430

Gly Ala Ile Thr Asp Lys Thr Arg Gln Ile Lys Pro Ile Ile Val Ile
            435                 440                 445

Ser Ser Ile Phe Gly Val Val Gly Ala Gly Ile Leu Thr Leu Leu Asn
450                 455                 460

Asn Asn Ala Asn Asn Ser Ala His Ile Gly Leu Leu Ile Leu Pro Gly
465                 470                 475                 480

Val Ala Phe Gly Gly Leu Ala Gln Ser Ser Met Leu Ala Ser Gln Ile
            485                 490                 495

Gln Leu Asp Lys Lys Ser Pro Thr Phe Arg Ser Asp Phe Val Ser Ile
        500                 505                 510

Thr Thr Phe Asn Thr Phe Cys Lys Asn Leu Gly Gln Ala Leu Gly Gly
            515                 520                 525

Val Ile Ser Asn Thr Val Phe Ser Ala Ala Ile Lys Lys Leu Thr
        530                 535                 540

Lys Ala Asn Ile Gln Leu Pro Asp Gly Thr Thr Val Asp Asn Leu Val
545                 550                 555                 560

Ile Tyr Arg Gln Thr Asn Phe Asp Gly Ser His Ser Lys Leu Gly Asn
            565                 570                 575

Ile Ile Ser Glu Ser Leu Thr Asp Val Phe Tyr Met Ala Leu Gly Phe
            580                 585                 590

Tyr Ala Leu Ser Leu Ile Phe Ala Val Phe Ala Ser Asn Lys Lys Val
            595                 600                 605

Thr Ala Ser Leu Arg
    610

<210> SEQ ID NO 30
<211> LENGTH: 543

<212> TYPE: PRT
<213> ORGANISM: Saccharomyces cerevisiae

<400> SEQUENCE: 30

```
Met Lys Ser Thr Leu Ser Leu Thr Leu Cys Val Ile Ser Leu Leu Leu
1               5                   10                  15

Thr Leu Phe Leu Ala Ala Leu Asp Ile Val Ile Val Thr Leu Tyr
            20                  25                  30

Asp Thr Ile Gly Ile Lys Phe His Asp Phe Gly Asn Ile Gly Trp Leu
            35                  40                  45

Val Thr Gly Tyr Ala Leu Ser Asn Ala Val Phe Met Leu Leu Trp Gly
        50                  55                  60

Arg Leu Ala Glu Ile Leu Gly Thr Lys Glu Cys Leu Met Ile Ser Val
65              70                  75                  80

Ile Val Phe Glu Ile Gly Ser Leu Ile Ser Ala Leu Ser Asn Ser Met
                85                  90                  95

Ala Thr Leu Ile Ser Gly Arg Val Val Ala Gly Phe Gly Gly Ser Gly
            100                 105                 110

Ile Glu Ser Leu Ala Phe Val Val Gly Thr Ser Ile Val Arg Glu Asn
        115                 120                 125

His Arg Gly Ile Met Ile Thr Ala Leu Ala Ile Ser Tyr Val Ile Ala
    130                 135                 140

Glu Gly Val Gly Pro Phe Ile Gly Gly Ala Phe Asn Glu His Leu Ser
145                 150                 155                 160

Trp Arg Trp Cys Phe Tyr Ile Asn Leu Pro Ile Gly Ala Phe Ala Phe
                165                 170                 175

Ile Ile Leu Ala Phe Cys Asn Thr Ser Gly Glu Pro His Gln Lys Met
            180                 185                 190

Trp Leu Pro Ser Lys Ile Lys Lys Ile Met Asn Tyr Asp Tyr Gly Glu
        195                 200                 205

Leu Leu Lys Ala Ser Phe Trp Lys Asn Thr Phe Glu Val Leu Val Phe
210                 215                 220

Lys Leu Asp Met Val Gly Ile Ile Leu Ser Ser Ala Gly Phe Thr Leu
225                 230                 235                 240

Leu Met Leu Gly Leu Ser Phe Gly Gly Asn Asn Phe Pro Trp Asn Ser
                245                 250                 255

Gly Ile Ile Ile Cys Phe Phe Thr Val Gly Pro Ile Leu Leu Leu Leu
            260                 265                 270

Phe Cys Ala Tyr Asp Phe His Phe Leu Ser Leu Ser Gly Leu His Tyr
        275                 280                 285

Asp Asn Lys Arg Ile Lys Pro Leu Leu Thr Trp Asn Ile Ala Ser Asn
290                 295                 300

Cys Gly Ile Phe Thr Ser Ser Ile Thr Gly Phe Leu Ser Cys Phe Ala
305                 310                 315                 320

Tyr Glu Leu Gln Ser Ala Tyr Leu Val Gln Leu Tyr Gln Leu Val Phe
                325                 330                 335

Lys Lys Lys Pro Thr Leu Ala Ser Ile His Leu Trp Glu Leu Ser Ile
            340                 345                 350

Pro Ala Met Ile Ala Thr Met Ala Ile Ala Tyr Leu Asn Ser Lys Tyr
        355                 360                 365

Gly Ile Ile Lys Pro Ala Ile Val Phe Gly Val Leu Cys Gly Ile Val
    370                 375                 380

Gly Ser Gly Leu Phe Thr Leu Ile Asn Gly Glu Leu Ser Gln Ser Ile
385                 390                 395                 400
```

-continued

```
Gly Tyr Ser Ile Leu Pro Gly Ile Ala Phe Gly Ser Ile Phe Gln Ala
                405                 410                 415

Thr Leu Leu Ser Ser Gln Val Gln Ile Thr Ser Asp Asp Pro Asp Phe
            420                 425                 430

Gln Asn Lys Phe Ile Glu Val Thr Ala Phe Asn Ser Phe Ala Lys Ser
        435                 440                 445

Leu Gly Phe Ala Phe Gly Gly Asn Met Gly Ala Met Ile Phe Thr Ala
    450                 455                 460

Ser Leu Lys Asn Gln Met Arg Ser Ser Gln Leu Asn Ile Pro Gln Phe
465                 470                 475                 480

Thr Ser Val Glu Thr Leu Leu Ala Tyr Ser Thr Glu His Tyr Asp Gly
                485                 490                 495

Pro Gln Ser Ser Leu Ser Lys Phe Ile Asn Thr Ala Ile His Asp Val
            500                 505                 510

Phe Tyr Cys Ala Leu Gly Cys Tyr Ala Leu Ser Phe Phe Phe Gly Ile
        515                 520                 525

Phe Thr Ser Ser Lys Lys Thr Thr Ile Ser Ala Lys Lys Gln Gln
    530                 535                 540
```

<210> SEQ ID NO 31
<211> LENGTH: 628
<212> TYPE: PRT
<213> ORGANISM: Saccharomyces cerevisiae

<400> SEQUENCE: 31

```
Met Asp Pro Gly Ile Ala Asn His Thr Leu Pro Glu Glu Phe Glu Glu
1               5                   10                  15

Val Val Val Pro Glu Met Leu Glu Lys Glu Val Gly Ala Lys Val Asp
                20                  25                  30

Val Lys Pro Thr Leu Thr Thr Ser Pro Ala Pro Ser Tyr Ile Glu
            35                  40                  45

Leu Ile Asp Pro Gly Val His Asn Ile Glu Ile Tyr Ala Glu Met Tyr
    50                  55                  60

Asn Arg Pro Ile Tyr Arg Val Ala Leu Phe Phe Ser Leu Phe Leu Ile
65                  70                  75                  80

Ala Tyr Ala Tyr Gly Leu Asp Gly Asn Ile Arg Tyr Thr Phe Gln Ala
                85                  90                  95

Tyr Ala Thr Ser Ser Tyr Ser Gln His Ser Leu Leu Ser Thr Val Asn
            100                 105                 110

Cys Ile Lys Thr Val Ile Ala Ala Val Gly Gln Ile Phe Phe Ala Arg
        115                 120                 125

Leu Ser Asp Ile Phe Gly Arg Phe Ser Ile Met Ile Val Ser Ile Ile
    130                 135                 140

Phe Tyr Ser Met Gly Thr Ile Ile Glu Ser Gln Ala Val Asn Ile Thr
145                 150                 155                 160

Arg Phe Ala Val Gly Gly Cys Phe Tyr Gln Leu Gly Leu Thr Gly Ile
                165                 170                 175

Ile Leu Ile Leu Glu Val Ile Ala Ser Asp Phe Ser Asn Leu Asn Trp
            180                 185                 190

Arg Leu Leu Ala Leu Phe Ile Pro Ala Leu Pro Phe Ile Asn Thr
        195                 200                 205

Trp Ile Ser Gly Asn Val Thr Ser Ala Ile Asp Ala Asn Trp Lys Trp
    210                 215                 220

Gly Ile Gly Met Trp Ala Phe Ile Leu Pro Leu Ala Cys Ile Pro Leu
```

```
           225                 230                 235                 240
       Gly Ile Cys Met Leu His Met Arg Tyr Leu Ala Arg Lys His Ala Lys
                       245                 250                 255

Asp Arg Leu Lys Pro Glu Phe Glu Ala Leu Asn Lys Leu Lys Trp Lys
                       260                 265                 270

Ser Phe Cys Ile Asp Ile Ala Phe Trp Lys Leu Asp Ile Ile Gly Met
                       275                 280                 285

Leu Leu Ile Thr Val Phe Phe Gly Cys Val Leu Val Pro Phe Thr Leu
                       290                 295                 300

Ala Gly Gly Leu Lys Glu Glu Trp Lys Thr Ala His Ile Ile Val Pro
       305                 310                 315                 320

Glu Val Ile Gly Trp Val Val Leu Pro Leu Tyr Met Leu Trp Glu
                       325                 330                 335

Ile Lys Tyr Ser Arg His Pro Leu Thr Pro Trp Asp Leu Ile Gln Asp
                       340                 345                 350

Arg Gly Ile Phe Phe Ala Leu Leu Ile Ala Phe Phe Ile Asn Phe Asn
                       355                 360                 365

Trp Tyr Met Gln Gly Asp Tyr Met Tyr Thr Val Leu Val Val Ala Val
                       370                 375                 380

His Glu Ser Ile Lys Ser Ala Thr Arg Ile Thr Ser Leu Tyr Ser Phe
       385                 390                 395                 400

Val Ser Val Ile Val Gly Thr Ile Leu Gly Phe Ile Leu Ile Lys Val
                       405                 410                 415

Arg Arg Thr Lys Pro Phe Ile Ile Phe Gly Ile Ser Cys Trp Ile Val
                       420                 425                 430

Ser Phe Gly Leu Leu Val His Tyr Arg Gly Asp Ser Gly Ala His Ser
                       435                 440                 445

Gly Ile Ile Gly Ser Leu Cys Leu Leu Gly Phe Ala Gly Ser Phe
                       450                 455                 460

Thr Tyr Val Thr Gln Ala Ser Ile Gln Ala Ser Ala Lys Thr His Ala
       465                 470                 475                 480

Arg Met Ala Val Val Thr Ser Leu Tyr Leu Ala Thr Tyr Asn Ile Gly
                       485                 490                 495

Ser Ala Phe Gly Ser Ser Val Ser Gly Ala Val Trp Thr Asn Ile Leu
                       500                 505                 510

Pro Lys Glu Ile Ser Lys Arg Ile Ser Asp Pro Thr Leu Ala Ala Gln
                       515                 520                 525

Ala Tyr Gly Ser Pro Phe Thr Phe Ile Thr Thr Tyr Thr Trp Gly Thr
                       530                 535                 540

Pro Glu Arg Ile Ala Leu Val Met Ser Tyr Arg Tyr Val Gln Lys Ile
       545                 550                 555                 560

Leu Cys Ile Ile Gly Leu Val Phe Cys Phe Pro Leu Leu Gly Cys Ala
                       565                 570                 575

Phe Met Leu Arg Asn His Lys Leu Thr Asp Ser Ile Ala Leu Glu Gly
                       580                 585                 590

Asn Asp His Leu Glu Ser Lys Asn Thr Phe Glu Ile Glu Glu Lys Glu
                       595                 600                 605

Glu Ser Phe Leu Lys Asn Lys Phe Phe Thr His Phe Thr Ser Ser Lys
                       610                 615                 620

Asp Arg Lys Asp
       625

<210> SEQ ID NO 32
```

<211> LENGTH: 606
<212> TYPE: PRT
<213> ORGANISM: Saccharomyces cerevisiae

<400> SEQUENCE: 32

```
Met Leu Glu Thr Asp His Ser Arg Asn Asp Asn Leu Asp Asp Lys Ser
1               5                   10                  15

Thr Val Cys Tyr Ser Glu Lys Thr Asp Ser Asn Val Glu Lys Ser Thr
            20                  25                  30

Thr Ser Gly Leu Arg Arg Ile Asp Ala Val Asn Lys Val Leu Ser Asp
        35                  40                  45

Tyr Ser Ser Phe Thr Ala Phe Gly Val Thr Phe Ser Ser Leu Lys Thr
    50                  55                  60

Ala Leu Leu Val Ala Leu Phe Leu Gln Gly Tyr Cys Thr Gly Leu Gly
65                  70                  75                  80

Gly Gln Ile Ser Gln Ser Ile Gln Thr Tyr Ala Ala Asn Ser Phe Gly
                85                  90                  95

Lys His Ser Gln Val Gly Ser Ile Asn Thr Val Lys Ser Ile Val Ala
            100                 105                 110

Ser Val Val Ala Val Pro Tyr Ala Arg Ile Ser Asp Arg Phe Gly Arg
        115                 120                 125

Ile Glu Cys Trp Ile Phe Ala Leu Val Leu Tyr Thr Ile Gly Glu Ile
    130                 135                 140

Ile Ser Ala Ala Thr Pro Thr Phe Ser Gly Leu Phe Ala Gly Ile Val
145                 150                 155                 160

Ile Gln Gln Phe Gly Tyr Ser Gly Phe Arg Leu Leu Ala Thr Ala Leu
                165                 170                 175

Thr Gly Asp Leu Ser Gly Leu Arg Asp Arg Thr Phe Ala Met Asn Ile
            180                 185                 190

Phe Leu Ile Pro Val Ile Ile Asn Thr Trp Val Ser Gly Asn Ile Val
        195                 200                 205

Ser Ser Val Ala Gly Asn Val Ala Pro Tyr Lys Trp Arg Trp Gly Tyr
    210                 215                 220

Gly Ile Phe Cys Ile Ile Val Pro Ile Ser Thr Leu Ile Leu Val Leu
225                 230                 235                 240

Pro Tyr Val Tyr Ala Gln Tyr Ile Ser Trp Arg Ser Gly Lys Leu Pro
                245                 250                 255

Pro Leu Lys Leu Lys Glu Lys Gly Gln Thr Leu Arg Gln Thr Leu Trp
            260                 265                 270

Lys Phe Ala Asp Asp Ile Asn Leu Ile Gly Val Ile Leu Phe Thr Ala
        275                 280                 285

Phe Leu Val Leu Val Leu Leu Pro Leu Thr Ile Ala Gly Gly Ala Thr
    290                 295                 300

Ser Lys Trp Arg Glu Gly His Ile Ile Ala Met Ile Val Val Gly Gly
305                 310                 315                 320

Cys Leu Gly Phe Ile Phe Leu Ile Trp Glu Leu Lys Phe Ala Lys Asn
                325                 330                 335

Pro Phe Ile Pro Arg Val Tyr Leu Gly Asp Pro Thr Ile Tyr Val Ala
            340                 345                 350

Leu Leu Met Glu Phe Val Trp Arg Leu Gly Leu Gln Ile Glu Leu Glu
        355                 360                 365

Tyr Leu Val Thr Val Leu Met Val Ala Phe Gly Glu Ser Thr Leu Ser
    370                 375                 380

Ala Gln Arg Ile Ala Gln Leu Tyr Asn Phe Leu Gln Ser Cys Thr Asn
```

-continued

```
                385                 390                 395                 400
        Ile Val Val Gly Ile Met Leu His Phe Tyr Pro His Pro Lys Val Phe
                        405                 410                 415
        Val Val Ala Gly Ser Leu Leu Gly Val Ile Gly Met Gly Leu Leu Tyr
                        420                 425                 430
        Lys Tyr Arg Val Val Tyr Asp Gly Ile Ser Gly Leu Ile Gly Ala Glu
                        435                 440                 445
        Ile Val Val Gly Ile Ala Gly Gly Met Ile Arg Phe Pro Met Trp Thr
                        450                 455                 460
        Leu Val His Ala Ser Thr Thr His Asn Glu Met Ala Thr Val Thr Gly
        465                 470                 475                 480
        Leu Leu Met Ser Val Tyr Gln Ile Gly Asp Ala Val Gly Ala Ser Ile
                        485                 490                 495
        Ala Gly Ala Ile Trp Thr Gln Arg Leu Ala Lys Glu Leu Ile Gln Arg
                        500                 505                 510
        Leu Gly Ser Ser Leu Gly Met Ala Ile Tyr Lys Ser Pro Leu Asn Tyr
                        515                 520                 525
        Leu Lys Lys Tyr Pro Ile Gly Ser Glu Val Arg Val Gln Met Ile Glu
                        530                 535                 540
        Ser Tyr Ser Lys Ile Gln Arg Leu Leu Ile Ile Val Ser Ile Ser Phe
        545                 550                 555                 560
        Ala Ala Phe Asn Ala Val Leu Cys Phe Phe Leu Arg Gly Phe Thr Val
                        565                 570                 575
        Asn Lys Lys Gln Ser Leu Ser Ala Glu Glu Arg Glu Lys Glu Lys Leu
                        580                 585                 590
        Lys Ile Lys Gln Gln Ser Trp Leu Arg Arg Val Ile Gly Tyr
                        595                 600                 605

<210> SEQ ID NO 33
<211> LENGTH: 615
<212> TYPE: PRT
<213> ORGANISM: Saccharomyces cerevisiae

<400> SEQUENCE: 33

Met Ser Ser Ser Val Val Gly Ala Ser Ser Asn Lys Lys Ser Gly Ile
1               5                   10                  15

Arg Gln Ser Cys Glu Ile Ile Glu Arg Glu Arg His Ser Asn Asp Asp
                20                  25                  30

Thr Tyr Ser Met Thr Ser Thr Phe Phe Lys Leu Lys Glu Asn Glu Ile
            35                  40                  45

Met Ser Ala Gln Phe Asp Ser Leu Lys Tyr Lys Ile Leu Leu Ile Ser
        50                  55                  60

Thr Ala Phe Val Cys Gly Phe Gly Ile Ser Leu Asp Tyr Thr Leu Arg
65                  70                  75                  80

Ser Thr Tyr Thr Gly Tyr Ala Thr Asn Ser Tyr Ser Glu His Ser Leu
                85                  90                  95

Leu Ser Thr Val Gln Val Ile Asn Ala Val Val Ser Val Gly Ser Gln
                100                 105                 110

Val Val Tyr Ser Arg Leu Ser Asp His Phe Gly Arg Leu Arg Leu Phe
                115                 120                 125

Leu Val Ala Thr Ile Phe Tyr Ile Met Gly Thr Ile Ile Gln Ser Gln
            130                 135                 140

Ala Thr Arg Leu Thr Met Tyr Ala Ala Gly Ser Val Phe Tyr Asn Cys
145                 150                 155                 160
```

```
Gly Tyr Val Gly Thr Asn Leu Leu Thr Leu Ile Leu Ser Asp Phe
            165                 170                 175

Ser Ser Leu Lys Trp Arg Met Phe Tyr Gln Tyr Ala Ser Tyr Trp Pro
        180                 185                 190

Tyr Ile Ile Ile Pro Trp Ile Ser Gly Asn Ile Ile Thr Ala Ala Asn
    195                 200                 205

Pro Gln Lys Asn Trp Ser Trp Asn Ile Ala Met Trp Ala Phe Ile Tyr
        210                 215                 220

Pro Leu Ser Thr Leu Pro Ile Ile Phe Leu Ile Leu Tyr Met Lys Tyr
225                 230                 235                 240

Lys Ser Ser Lys Thr Ala Glu Trp Arg Ser Leu Lys Glu Gln Ala Arg
                245                 250                 255

Lys Glu Arg Thr Gly Gly Leu Phe Glu Asn Leu Val Phe Leu Phe Trp
            260                 265                 270

Lys Leu Asp Ile Val Gly Ile Leu Leu Ile Thr Val Ser Leu Gly Cys
        275                 280                 285

Ile Leu Val Pro Leu Thr Leu Ala Asn Glu Thr Ser Gln Lys Trp His
    290                 295                 300

Asn Ser Lys Ile Ile Ala Thr Leu Val Ser Gly Gly Cys Leu Phe Phe
305                 310                 315                 320

Ile Phe Leu Tyr Trp Glu Ala Lys Phe Ala Lys Ser Pro Leu Leu Pro
                325                 330                 335

Phe Lys Leu Leu Ser Asp Arg Gly Ile Trp Ala Pro Leu Gly Val Thr
            340                 345                 350

Phe Phe Asn Phe Phe Thr Phe Phe Ile Ser Cys Asp Tyr Leu Tyr Pro
        355                 360                 365

Val Leu Leu Val Ser Met Lys Glu Ser Ser Thr Ser Ala Ala Arg Ile
370                 375                 380

Val Asn Leu Pro Asp Phe Val Ala Ala Thr Ala Ser Pro Phe Tyr Ser
385                 390                 395                 400

Leu Leu Val Ala Lys Thr Arg Lys Leu Lys Leu Ser Val Ile Gly Gly
            405                 410                 415

Cys Ala Ala Trp Met Val Cys Met Gly Leu Phe Tyr Lys Tyr Arg Gly
        420                 425                 430

Gly Ser Gly Ser His Glu Gly Val Ile Ala Ala Ser Val Ile Met Gly
    435                 440                 445

Leu Ser Gly Leu Leu Cys Ser Asn Ser Val Ile Val Ile Leu Gln Ala
    450                 455                 460

Met Thr Thr His Ser Arg Met Ala Val Ile Thr Gly Ile Gln Tyr Thr
465                 470                 475                 480

Phe Ser Lys Leu Gly Ala Ala Ile Gly Ala Ser Val Ser Gly Ala Ile
            485                 490                 495

Trp Thr Gln Thr Met Pro Asn Gln Leu Tyr Lys Asn Leu Gly Asn Asp
        500                 505                 510

Thr Leu Ala Glu Ile Ala Tyr Ala Ser Pro Tyr Thr Phe Ile Ser Asp
    515                 520                 525

Tyr Pro Trp Gly Ser Pro Glu Arg Asp Ala Val Val Glu Ser Tyr Arg
    530                 535                 540

Tyr Val Gln Arg Ile Ile Met Thr Val Gly Leu Ala Cys Thr Val Pro
545                 550                 555                 560

Phe Phe Thr Phe Thr Met Phe Met Arg Asn Pro Glu Leu Ile Asp Lys
            565                 570                 575

Ala Thr His Glu Glu Phe Thr Glu Asp Gly Leu Val Val Leu Pro Asp
```

```
                    580             585             590
Glu Glu Asn Ile Phe Ser Gln Ile Lys Ala Leu Phe Arg His Asn Arg
        595                 600                 605

Ser Asn Lys Lys Ser Gly Cys
    610                 615

<210> SEQ ID NO 34
<211> LENGTH: 946
<212> TYPE: DNA
<213> ORGANISM: Saccharomyces cerevisiae
<220> FEATURE:
<221> NAME/KEY: misc_feature
<223> OTHER INFORMATION: pCCW12

<400> SEQUENCE: 34
gaaacttaat acgttatgcc gtaatgaagg gctaccaaaa acgataatct caactgtaaa      60
caggtacaat gcggacccct tgccacaaa acatacatca ttcattgccg gaaaagaaa      120 gaagtgaaga cagcagtgca gccagccatg ttgcgccaat ctaattatag atgctggtgc     180
cctgaggatg tatctggagc cagccatggc atcatgcgct accgccggat gtaaaatccg     240
acacgcaaaa gaaaaccttc gaggttgcgc acttcgccca cccatgaacc acacggttag     300
tccaaaaggg gcagttcaga ttccagatgc gggaattagc ttgctgccac cctcacctca     360
ctaacgctgc ggtgtgcgga tacttcatgc tatttataga cgcgcgtgtc ggaatcagca     420
cgcgcaagaa ccaaatggga aaatcggaat gggtccagaa ctgctttgag tgctggctat     480
tggcgtctga tttccgtttt gggaatcctt gccgcgcgc cctctcaaa actccgcaca     540 agtcccagaa agcgggaaag aaataaaacg ccaccaaaaa aaaaaataaa agccaatcct     600
cgaagcgtgg gtggtaggcc ctggattatc ccgtacaagt atttctcagg agtaaaaaaa     660
ccgtttgttt tggaattccc catttcgcgg ccacctacgc cgctatcttt gcaacaacta     720
tctgcgataa ctcagcaaat tttgcatatt cgtgttgcag tattgcgata atgggagtct     780
tacttccaac ataacggcag aaagaaatgt gagaaaattt tgcatccttt gcctccgttc     840
aagtatataa agtcggcatg cttgataatc tttctttcca tcctacattg ttctaattat     900
tcttattctc ctttattctt tcctaacata ccaagaaatt aatctt                    946

<210> SEQ ID NO 35
<211> LENGTH: 300
<212> TYPE: DNA
<213> ORGANISM: Saccharomyces cerevisiae
<220> FEATURE:
<221> NAME/KEY: misc_feature
<223> OTHER INFORMATION: tRPL15A

<400> SEQUENCE: 35
gctggttgat ggaaaatata attttattgg gcaaactttt gtttatctga tgtgttttat      60
actattatct ttttaattaa tgattctata tacaaacctg tatatttttt ctttaaccaa     120
tttttttttt tatagaccta gagctgtact tttattctgc tatcaagcaa accoctaccc     180 cctcttctca atcctccect caggcagaac ttatctacct gtatcaagga gcggacgagg     240
gagtcctaat tgttctacgt ataccaatgc tagcagctta cataggtggt ggcactacca     300
```

PHLOROGLUCINOL-RESISTANT CELL, IN PARTICULAR YEAST

FIELD OF THE INVENTION

The present invention lies in the fields of cellular biochemistry and more particularly in the field of the synthesis of phloroglucinol by living cells, preferably recombinant host cells. It relates to the use (i) of transmembrane transporters of the ABC family, in particular transmembrane transporters of the PDR subfamily, or (ii) of transcription factors which control the expression of transmembrane transporters of the PDR subfamily, or else (iii) of transmembrane transporters of the MFS family, in particular the use of such transporters or transcription factors derived from yeasts, more particularly from *Saccharomyces* yeasts, for conferring phloroglucinol resistance.

PRIOR ART

Phloroglucinol or benzene-1,3,5-triol is an aromatic organic compound used in the synthesis of numerous pharmaceutical products or else explosives. Given the broad field of application of phloroglucinol, manufacturers are always searching for means and tools which make it possible to produce this compound in large amount in an economically cost-effective system. To this effect, certain challenges remain to be resolved, in particular because one of the principal difficulties to be overcome lies in the fact that phloroglucinol has antibiotic properties and that it is thus complicated to set up a high-yield industrial in vivo production system.

Interestingly, Cao et al. have shown, in bacteria of *Escherichia coli* type, that overexpression of the marA gene, a transcriptional activator of genes involved in resistance to multiple antibiotics, makes it possible to increase the resistance of said bacteria to phloroglucinol (Cao et al., 2011). However, these toxic effects of phloroglucinol currently remain barely studied in the literature.

Thus, there remains at the current time the need to identify new means and tools capable of providing increased resistance with respect to the toxicity conferred by phloroglucinol.

All organisms have developed transport mechanisms by which endogenous and exogenous toxic substances can be secreted. The two main classes of transport proteins are the ABC transporters (Decottignies, 1997) and the MFS ("major facilitator superfamily") transporters (Del Sorbo, 2000). The members of the two classes exhibit a broad substrate specificity.

In *S. cerevisiae*, about thirty ABC proteins have been identified and classified into five phylogenetic subfamilies (Decottignies, 1997). These proteins exhibit a very conserved structural organization including two transmembrane domains and two cytoplasmic domains delivering the energy required for transport. The structural organization is the basis of the classification of the proteins into families denoted ABC-A to ABC-G. The overexpression of PDRs ("pleiotropic drug resistance") frequently correlates with multiresistance (Holland, 2003). In *S. cerevisiae*, the PDR proteins constitute a subfamily of ABC transporters, involved in resistance to xenobiotics (E. Balzi, 1995; Kolaczkowski, 1998). The most important PDRs are Pdr5 and Yor1, which show a broad substrate specificity (Mahé, 1996). Certain members of the PDR subfamily, such as Pdr10p and Pdr15p, are also linked to the general response to stress (Wolfger, 2004). Pdr12p plays an essential role in the response and adaptation to unfavourable conditions (stress) (Piper, 1998).

MFSs are also transmembrane proteins involved in the transport of molecules (oligosaccharides, xenobiotics, amino acids) using chemiosmotic concentration gradients (Marger, 1993). The MFS transporters can be divided into three main groups, as a function of the mode of transport: uniporters which allow movement of a single molecule or of a single ion in one direction through the membrane; symporters which allow movement of two different molecules or of a molecule and a coupling ion (typically protons) in one and the same direction through the membrane; and antiporters which allow movement of two molecules or of a molecule and an ion in opposite directions through the membrane, such that the binding of one depends on the prior release of the other (Forrest, 2011). MFSs are classified into 74 subfamilies based on the phylogenetic analysis, the substrate specificity, and the mode of transport. The substrate specificity is determined essentially by the side chains of the amino acid residues lining the central cavity hollowed out by the transporter in the lipid bilayer of the membrane (Yan, 2013).

The inventors have sought means and tools for increasing the tolerance of yeasts to phloroglucinol. In the context of their work, they have studied the overexpression of proteins belonging to the PDR transporter subfamily. They have in particular studied the twelve transporters present on the cytoplasmic membrane of yeast (Yor1p, Pdr5p, Pdr10p, Pdr12p, Pdr15p, Snq2, Pdr11p, Pdr18p, Aus1p, Adp1p, Yol075cp and Ste6p), and also two transcription factors (Pdr1p and Pdr3p). Ten of the twelve transporters selected belong to the family G, the leading member of which is BCRP ("breast cancer resistance protein"); the other two proteins belong to the families ABC-B and ABC-C, the leading members of which are respectively MDR1 and MRP1, widely involved in resistance to anticancer drugs in human beings. The inventors have also studied 19 sequences of transporters of the MFS family that are located at the cytoplasmic membrane.

Unexpectedly, the inventors have demonstrated the effect (i) of the transmembrane transporters of the ABC family, in particular of the transmembrane transporters of the PDR subfamily, or (ii) of the transcription factors which control the expression of the transmembrane transporters of the PDR subfamily, or else (iii) of the transmembrane transporters of the MFS family, in particular of the SNQ2, STE6, PDR3, AQR1, DTR1, FLR1, QDR1, YHK8 or ATR1 proteins and in particular of the SNQ2 membrane transporter, on the phloroglucinol resistance of yeasts, in particular of yeasts of *Saccharomyces* type, in particular of yeasts of *Saccharomyces cerevisiae* type.

SUMMARY OF THE INVENTION

The inventors have demonstrated, entirely surprisingly, that the overexpression (i) of the transmembrane transporters of the ABC family, in particular of the transmembrane transporters of the PDR subfamily, or (ii) of the transcription factors which control the expression of the transmembrane transporters of the PDR subfamily, or else (iii) of the transmembrane transporters of the MFS family, in a living cell, make it possible to increase its phloroglucinol resistance.

The first subject of the invention therefore relates to a living cell, preferably a host cell, that is phloroglucinol resistant, characterized in that it withstands a phloroglucinol concentration, in its culture medium, of greater than or equal to 1 g·l$^{-1}$.

According to the present invention, said living cell, preferably said host cell, overexpresses at least one membrane transporter, or at least one transcription factor which controls the expression of said membrane transporter, in particular selected from SNQ2, STE6, PDR3, AQR1, DTR1, FLR1, QDR1, YHK8 and ATR1 and preferably the SNQ2 transporter.

The invention also relates to a method for obtaining a phloroglucinol-resistant recombinant host cell, comprising at least the steps of:

i. providing a nucleic acid molecule which comprises at least one nucleic acid sequence encoding a polypeptide selected from the membrane transporters of the ABC family, preferably of the PDR subfamily, and the membrane transporters of the MFS family, or comprises a nucleic acid sequence encoding a transcription factor which controls the expression of a membrane transporter of the PDR subfamily, ii. cloning said nucleic acid molecule provided in step (i) in a vector capable of allowing the integration thereof and/or the expression thereof in said host cell, and iii. bringing said host cell and said vector obtained in step (ii) into contact so that said host cell is transfected with said vector and that said host cell expresses said nucleic acid molecule, said host cell thus being phloroglucinol resistant.

The present invention also relates to a method for producing phloroglucinol, comprising at least the steps:

i. of obtaining a host cell by carrying out a method according to the invention, ii. of bringing said host cell into contact with an appropriate substrate, iii. of incubating the mixture obtained in step (ii) under conditions suitable for producing phloroglucinol, and iv. optionally, of recovering the reaction medium comprising the phloroglucinol obtained after step (iii) and of purifying the phloroglucinol.

FIGURE LEGEND

FIG. 1: Growth kinetics of the ECAO50 bacterial strain, derived from *Escherichia coli* K12, in the presence of increasing concentrations of phloroglucinol.

Figure 2:
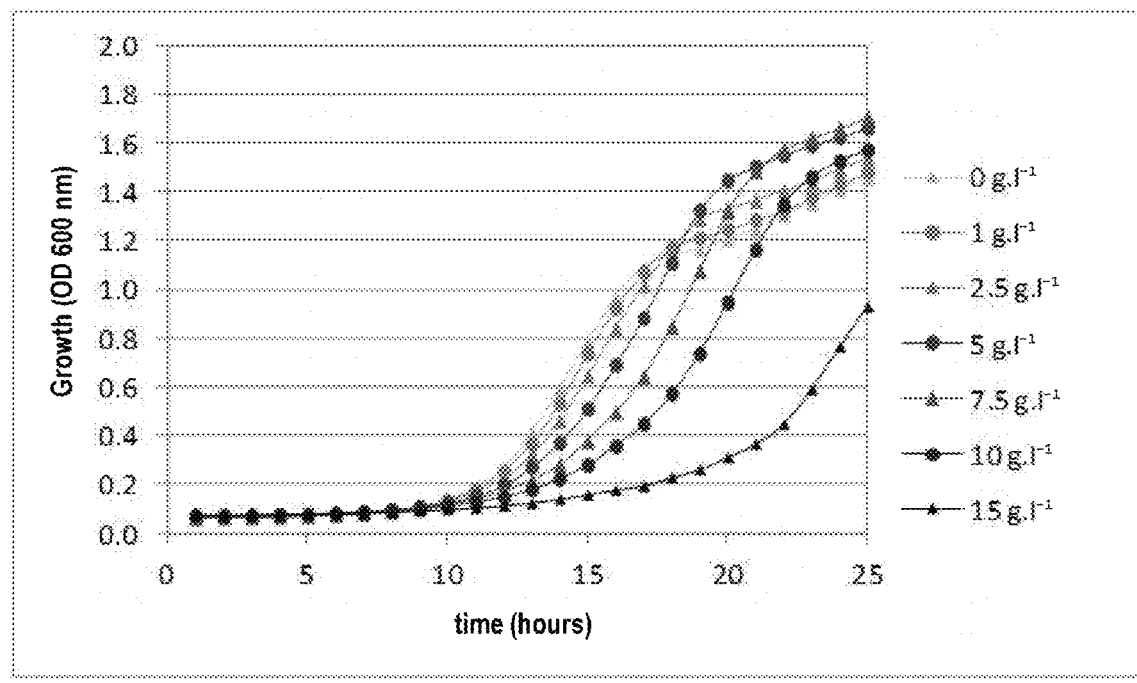

FIG. 2: Growth kinetics of the CC787-1B *S. cerevisiae* yeast strain in the presence of increasing concentrations of phloroglucinol.

Figure 3A:
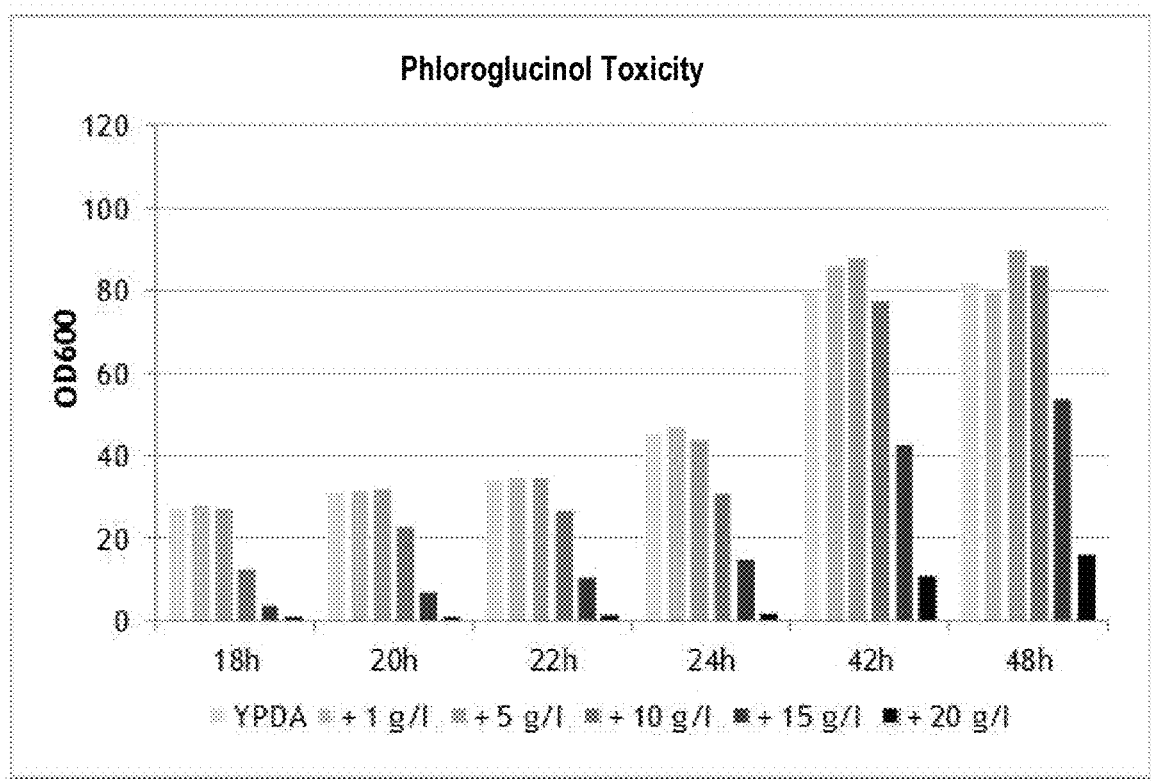

FIG. 3A: Phloroglucinol toxicity in the yeasts.

Figure 3B:
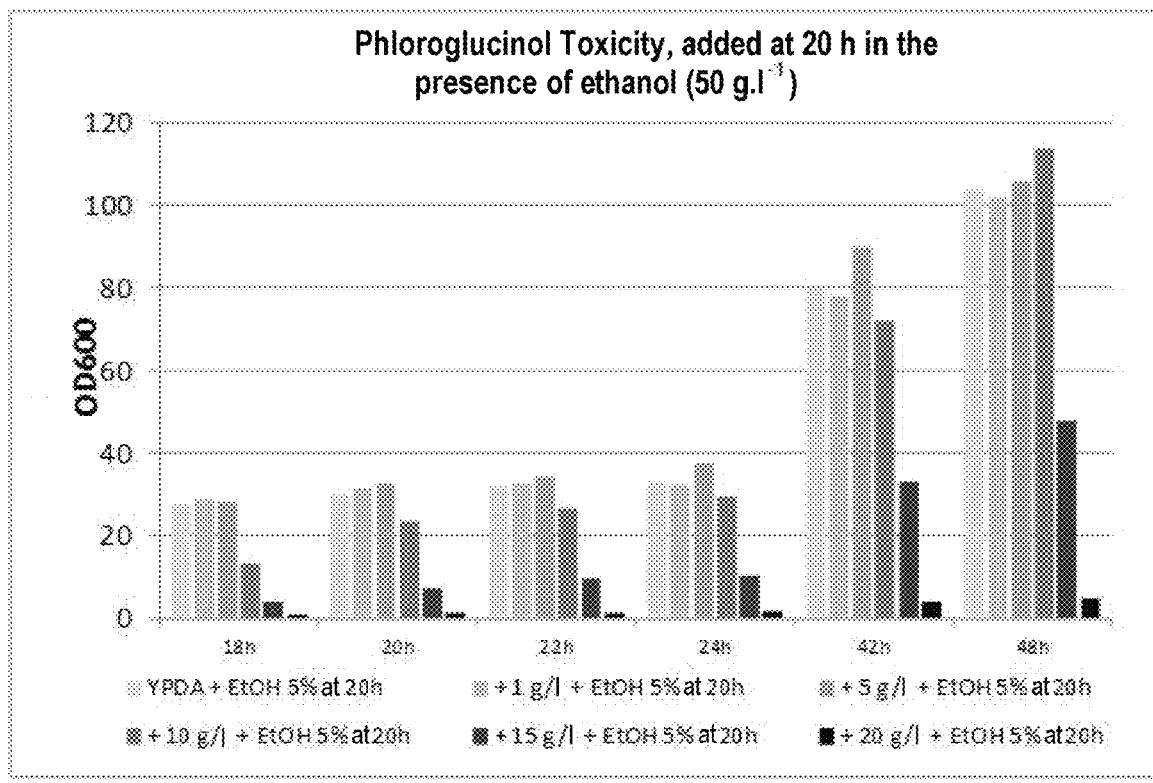

FIG. 3B: Phloroglucinol toxicity in the yeasts in the presence of ethanol added after 20 h of culture.

FIG. 4A: Structure of the cluster integrated in the genome of the yeast at the JLP1 locus, the gene encoding the transporter of the PDR subfamily or the transcription factor which controls the expression of a transporter of the PDR subfamily being under the control of the pCCW12 promoter.

FIG. 4B: For each gene, a strain was constructed bearing the number YA and two independent clones were kept for the analyses.

Figure 5:
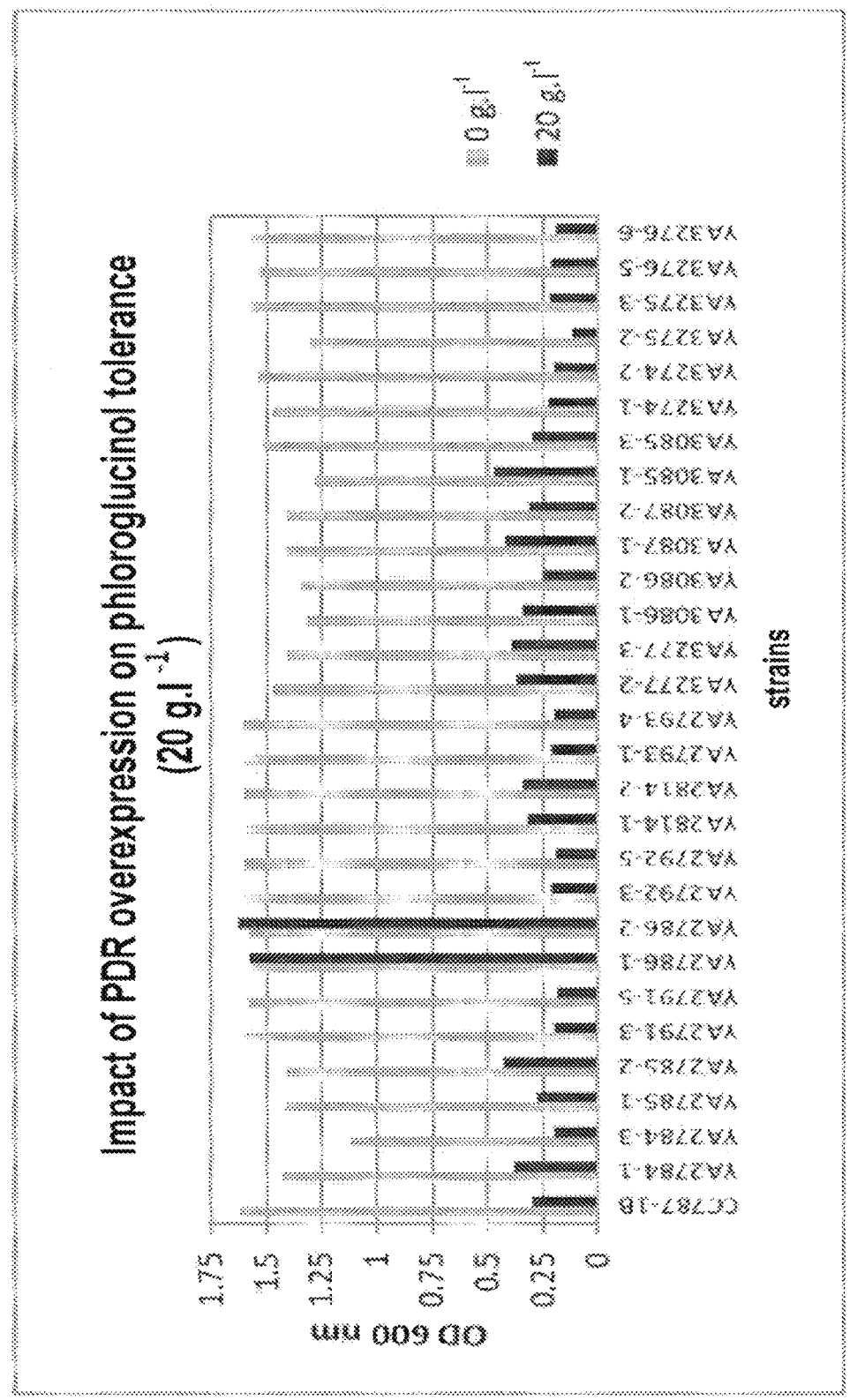

FIG. 5: Effect of the overexpression of PDRs on phloroglucinol toxicity (20 g·l$^{-1}$). The graph indicates the OD$_{600\ nm}$ at 24 h of the cultures of the various strains, each overexpressing a different PDR transporter or a different transcription factor which regulates the expression of a PDR transporter, in the absence or presence of 20 g·l$^{-1}$ of phloroglucinol.

FIG. 6A: Structure of the cluster integrated in the genome of the yeast at the JLP1 locus, the gene encoding the transporter of the MFS family being under the control of the pCCW12 promoter.

FIG. 6B: For each transporter, a strain was constructed bearing the number YA and two independent clones were kept for the analyses.

Figure 7:
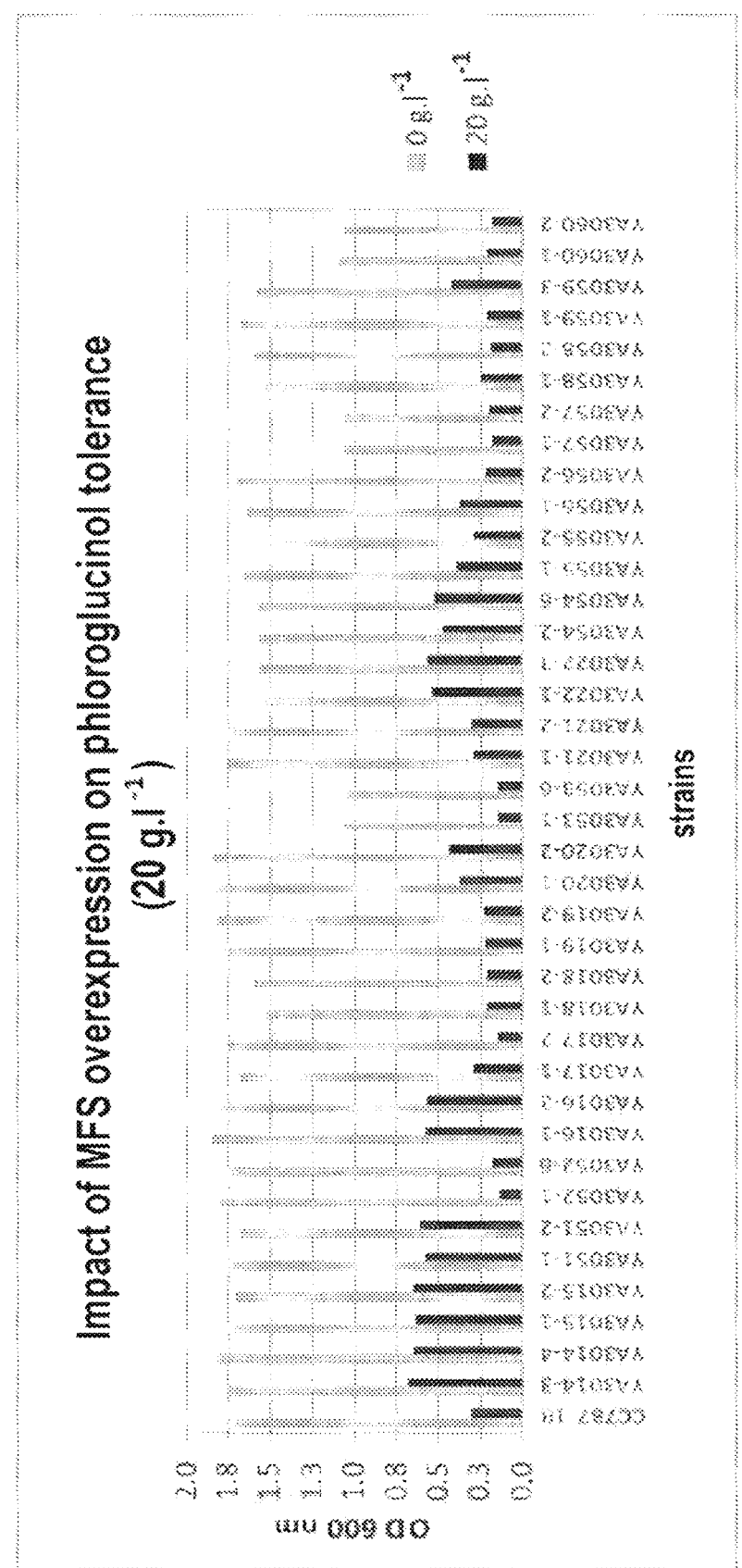

FIG. 7: Effect of the overexpression of MFSs on phloroglucinol toxicity (20 g·l$^{-1}$). The graph indicates the OD$_{600\ nm}$ at 24 h of the cultures of the various strains, each overexpressing a different PDR transporter, in the absence or presence of 20 g·l$^{-1}$ of phloroglucinol.

DETAILED DESCRIPTION OF THE INVENTION

Definitions

The term "phloroglucinol" is intended to mean an aromatic organic compound benzene-1,3,5-triol having the following chemical formula (Formula I):

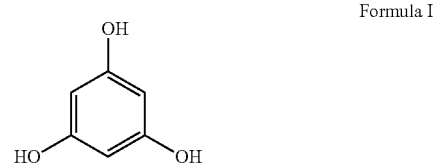

The term "phloroglucinol synthase" is intended to mean a multifunctional enzyme or an enzymatic complex belonging to the type III polyketide synthase family and catalysing the synthesis of phloroglucinol. A phloroglucinol synthase catalyses the condensation of three malonyl-CoA molecules so as to form one phloroglucinol molecule.

The term "type III polyketide synthase" is intended to mean a multifunctional enzyme or an enzymatic complex which produces polyketides and which does not use an acyl carrier protein (or ACP) domain.

The term "polyketide" is intended to mean a large family of secondary metabolites in bacteria, mycetes, plants and certain animal lines, which originate from the repeated condensation of acetyl or malonyl subunits by polyketide synthase enzymes. Polyketides also serve as starting materials for the production of a wide range of natural and semi-synthetic products.

The term "enzymatic activity" or "catalytic activity" or else "activity" of an enzyme is intended to mean the efficiency of an enzyme to convert a substrate into product in a given environment. The efficiency of the enzyme takes into account here the rate of conversion of the substrate into product by the enzyme and the degree of conversion of the substrate into product by the enzyme. The expression "degree of conversion of the substrate into product by the enzyme" is intended here to mean the ratio between the amount of final product obtained relative to the initial amount of substrate for a defined amount of enzyme. For example, an enzymatic activity for the purposes of the invention can be expressed in amount of phloroglucinol produced in a given volume (in g/l or g·l$^{-1}$).

The term "bacterium" is intended to mean a microscopic and prokaryotic organism present in a given medium.

The term "yeast" is intended to mean a microscopic and eukaryotic organism, some species of which are capable of causing the fermentation of organic matter.

The term "nucleic acid molecule" is intended to mean a polymer of any length of deoxyribonucleic acid (DNA), or polydeoxyribonucleotides, including in particular complementary DNA or cDNA, genomic DNA, plasmids, vectors, viral genomes, isolated DNA, probes, primers and any mixture thereof; or a polymer of any length of ribonucleic acid (RNA), or polyribonucleotides, including in particular messenger RNA or mRNA, antisense RNA; or mixed polyribo-polydeoxyribonucleotides. They encompass single-stranded or double-stranded, linear or circular, natural or synthetic polynucleotides. In addition, a polynucleotide may contain unnatural nucleotides and may be interrupted with non-nucleotide components.

In the context of the present invention, the terms "nucleic acid", "nucleic acid molecule", "polynucleotide" and "nucleotide sequence" are used interchangeably.

The term "isolated" is intended to mean a molecule, in particular a protein, a polypeptide, a peptide, a nucleic acid molecule, a plasmid vector, a viral vector or a host cell, which is extracted from its natural environment (i.e. separated from at least one other component with which it is naturally associated).

The terms "polypeptide", "protein" and "peptide" are intended to mean polymers of amino acid residues which comprise at least nine amino acids bonded by peptide bonds. The polymer may be linear, branched or cyclic. The polymer may comprise natural amino acids and/or amino acid analogues and it may be interrupted with non-amino-acid residues. As a general indication, and without however being bound by said indication, in the present application, if the amino acid polymer contains more than 50 amino acid residues, it is preferably called a polypeptide or a protein, whereas if the polymer consists of 50 amino acids or less, it is preferably called a peptide. The term "vector" is intended to mean a carrier, preferably a nucleic acid molecule or a viral particle, which contains the elements required for allowing the administration, the propagation and/or the expression of one or more nucleic acid molecule(s) in a host cell or an organism.

From a functional point of view, this term encompasses maintenance vectors (cloning vectors), vectors for expression in various host cells or organisms (expression vectors), extrachromosomal vectors (for example multicopy plasmids) or integration vectors (for example designed to integrate into the genome of a host cell and to produce additional copies of the nucleic acid molecule that it contains, when the host cell replicates). This term encompasses shuttle vectors (for example, operating both in prokaryotic and/or eukaryotic hosts) and transfer vectors (for example for the transfer of nucleic acid molecule(s) into the genome of a host cell).

From a structural point of view, the vectors can be natural, synthetic or artificial genetic sources, or a combination of natural and artificial genetic elements.

Thus, in the context of the invention, the term "vector" should be understood in the broad sense, including plasmid vectors (or plasmids) and viral vectors.

A "plasmid" as used herein denotes a replicable DNA construct. Usually, plasmid vectors contain selectable marker genes which enable the host cells carrying the plasmid to be identified and/or positively or negatively selected in the presence of the compound corresponding to the selectable marker. A variety of positive and negative selectable marker genes are known in the art. By way of illustration, an antibiotic resistance gene can be used as a positive selectable marker gene for selecting a host cell in the presence of the corresponding antibiotic.

The term "viral vector" as used herein refers to a nucleic acid vector which comprises at least one element of a genome of the virus and can be packaged in a viral particle. Viral vectors can be replication-competent or selective (for example, designed to replicate better or selectively in specific host cells), or can be genetically deactivated so as to be replication-defective or replication-deficient.

The term "living cell" is intended to mean a wild-type cell, that is to say a cell which exists in the natural state not genetically modified by human beings, or a cell of recombinant type, that is to say genetically modified by human beings. In the latter case, the term preferentially used will be host cell.

The living cell can consist of a single type of cells or of a group of different types of cells. The living cell can belong to cultured cell lines, to primary cells, to stem cells or to proliferative cells. In the context of the invention, the term "living cells" comprises prokaryotic cells, bacteria or cyanobacteria, eukaryotic cells such as yeast cells, fungal cells, algal cells, insect cells, plants and mammalian cells (for example human or non-human, preferably non-human, cells).

The term "host cell" is intended to mean a cell containing at least one exogenous nucleic acid molecule. Advantageously, the host cell has resistance with respect to phloroglucinol-induced toxicity.

In particular, the host cell is capable of expressing or overexpressing a polypeptide encoding an enzyme involved in phloroglucinol biosynthesis, preferably a polypeptide with phloroglucinol synthase activity, more preferentially a polypeptide encoding a type III polyketide synthase and is thus capable of synthesizing phloroglucinol.

The term "host cell" more broadly comprises cells which contain or have contained the nucleic acid molecule, and also the progeny of such cells.

The host cell can for example be isolated or organized in a tissue, or in an organ, or else can be within a whole organism. In the case where the host cell is within a whole organism, said organism is not human.

It is thus clear that a "host cell" according to the present invention is a recombinant host cell, i.e. a cell housing an exogenous genetic material. Thus, a host cell is not a cell which exists in the natural state, but is a molecular biology tool obtained by genetic manipulation techniques.

The term "exogenous" genetic material or sequence is intended to mean that said genetic material or said sequence originates from another organism, which may or may not belong to the same cell line.

The term "transfected" or "transfection" is intended to mean the introduction of exogenous genetic material into eukaryotic cells, in particular those of the invention. The term "transformed" or "transformation" is intended to mean the introduction of exogenous genetic material into prokaryotic cells, in particular those of the invention. Nevertheless, in the context of the present invention, the terms "transfection" and "transformation" are equivalent and can be used interchangeably.

The term "identity" is intended to mean an exact sequence correspondence between two polypeptides, between two proteins, between two peptides or two amino acid molecules. The "percentage identity" between two sequences is a function of the number of identical residues common to the two sequences, and takes into account the number of intervals which must be introduced for an optimal alignment and the length of each interval. Various computer programs and mathematical algorithms are available in the prior art for determining the percentage identity between amino acid sequences, such as for example the Blast program available on the NCBI base or the ALIGN base (Atlas of Protein Sequence and Structure, Dayhoff (ed.), 1981, Suppl. 3 482-489). Programs for determining the homology between nucleotide sequences are also available in a specialized database (for example Genbank, the Wisconsin Sequence Analysis Package, the BESTFIT, FASTA and GAP programs). By way of illustration, the expression "at least 80% sequence identity", as used herein, represents 80%, 81%, 82%, 83%, 84%, 85%, 86%, 87%, 88%, 89%, 90%, 91%, 92%, 93%, 94%, 95%, 96%, 97%, 98%, 99% or 100%.

In the detailed description which follows, the embodiments may be taken alone or combined in an appropriate manner by those skilled in the art.

Phloroglucinol-Resistant Living Cell

The first subject of the invention thus relates to a living cell, preferably a host cell, that is phloroglucinol resistant, characterized in that it withstands a phloroglucinol concentration, in its culture medium, of greater than or equal to 1 g·l$^{-1}$.

The term "phloroglucinol resistant" is intended to mean a living cell, preferably a host cell, which is not sensitive to phloroglucinol-induced toxicity. This living cell, preferably this host cell, is thus capable of living, growing and multiplying despite the presence of phloroglucinol in its culture medium, in particular despite a phloroglucinol concentration of at least 1 g·l$^{-1}$ in its culture medium. In one particular embodiment, said living cell, preferably said host cell, is phloroglucinol resistant if it is capable of living, growing and multiplying in the presence of a phloroglucinol concentration in its culture medium of greater than or equal to 1 g·l$^{-1}$, preferably greater than or equal to 2.5 g·l$^{-1}$, preferably greater than or equal to 5 g·l$^{-1}$, preferably greater than or equal to 7.5 g·l$^{-1}$, preferably greater than or equal to 10 g·l$^{-1}$, and more preferably greater than or equal to 15 g·l$^{-1}$. In one preferred embodiment, said living cell, preferably said host cell, is phloroglucinol resistant if it is capable of living, growing and multiplying in the presence of a phloroglucinol concentration in its culture medium of greater than or equal to 20 g·l$^{-1}$.

In practice, the phloroglucinol resistance of a living cell, preferably of a host cell, can be measured by any appropriate method known to those skilled in the art, in particular by the method described in Example 1.

In one preferred embodiment, said living cell, preferably said host cell, is a microorganism selected from bacteria, yeast, fungi, algae and cyanobacteria, preferably a yeast, said yeast being in particular selected from the genera *Saccharomyces, Candida, Ashbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* and *Malassezia*; more particularly from the species *Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa* and *Torulaspora glabrata*; even more particularly, the yeast being of the *Saccharomyces* genus, preferably of the *Saccharomyces cerevisiae* species.

Surprisingly, the inventors have been able to demonstrate that some of the transporters of the ABC family, and in particular some transporters of the PDR subfamily, like some transporters of the MFS family, are capable of conferring on the living cell resistance with respect to phloroglucinol-induced toxicity. Moreover, some transcription factors involved in the regulation of said transporters are also capable of conferring on the living cell resistance with respect to phloroglucinol-induced toxicity.

Thus, the present invention relates to a host cell characterized in that it overexpresses at least one membrane transporter, or at least one transcription factor which controls the expression of said membrane transporter.

Among the transporters of interest identified in the context of the present invention, mention may in particular be made of the transporters of the PDR subfamily: PDR5, SNQ2, PDR10, PDR11, PDR12, PDR15, PDR18, ADP1, AUS1, STE6, YOL075C and YOR1. Among the transcription factors of interest identified in the context of the present invention, mention may in particular be made of PDR1 and PDR3 which are involved in the regulation of the expression of the transporters of the PDR subfamily.

Thus, in one particular embodiment, said host cell is characterized in that said membrane transporter or said transcription factor which controls its expression belongs to the ABC transporter family and preferably to the PDR subfamily.

Among the transporters of interest identified in the context of the present invention, mention may also be made of the transporters of the MFS subfamily, in particular AQR1, DTR1, FLR1, HOL1, QDR1, QDR2, QDR3, TPO1, TPO2, TPO3, TPO4, YHK8, ATR1, GEX1, AZR1, SGE1, SIT1, ENB1 and GEX2.

Thus, in one particular embodiment, said host cell is characterized in that said membrane transporter belongs to the MFS transporter family.

The invention thus also relates to a phloroglucinol-resistant host cell characterized in that it overexpresses at least one transporter or one transcription factor selected from SNQ2, STE6, PDR3, AQR1, DTR1, FLR1, QDR1, YHK8 and ATR1.

In one preferred embodiment, said host cell is characterized in that it overexpresses the SNQ2 transporter.

Thus, the PDR transporters, the transcription factors which regulate the expression of the PDR transporters, and the MFS transporters, in particular SNQ2, can be derived from any organism having a sequence encoding said transporters or transcription factors.

In one embodiment, the PDR transporters, the transcription factors which regulate the expression of the PDR transporters, and the MFS transporters are derived from yeasts, which yeasts are in particular selected from yeasts of the *Saccharomyces* genus, and more particularly from the species *Saccharomyces cerevisiae, Saccharomyces boulardii, Saccharomyces douglasii, Saccharomyces bayanus, Zigosaccharomyces bairn, Schizosaccharomyces pombe, Dekkera brucelensis, Dekkera intermedia, Brettanomycces custersii, Brettanomycces intermedius, Kluyveromyces themotolerens, Torulaspora globosa* and *Torulaspora glabrata*; even more particularly, said yeasts being of the *Saccharomyces cerevisiae* species.

In another embodiment, said phloroglucinol-resistant host cell is a yeast, preferably of the *Saccharomyces cerevisiae* species, characterized in that it overexpresses the SNQ2 transporter. In one preferred embodiment, said phloroglucinol-resistant host cell is a yeast, preferably of the *Saccharomyces cerevisiae* species, characterized in that it overexpresses a polypeptide comprising at least one amino acid sequence having at least 70%, preferably at least 80%, identity with SEQ ID No. 2.

In one preferred embodiment among all, said phloroglucinol-resistant host cell is a yeast, preferably of the *Saccha-

*romyces cerevisiae* species, characterized in that it overexpresses the SNQ2 transporter of *Saccharomyces cerevisiae* of sequence SEQ ID No. 2.

Polypeptides

The present invention uses isolated polypeptides selected from (i) transmembrane transporters of the ABC family, in particular transmembrane transporters of the PDR subfamily, or (ii) transcription factors which control the expression of the transmembrane transporters of the PDR subfamily, or else (iii) transmembrane transporters of the MFS family; in particular from (i) transmembrane transporters of the ABC family from yeasts, in particular transmembrane transporters of the PDR subfamily from yeasts, or (ii) transcription factors which control the expression of the transmembrane transporters of the PDR subfamily from yeasts, or else (iii) transmembrane transporters of the MFS family from yeasts, in particular those from *Saccharomyces* yeasts, even more particularly of the *Saccharomyces cerevisiae* species.

The present invention uses isolated polypeptides selected from (i) transmembrane transporters of the ABC family, in particular transmembrane transporters of the PDR subfamily, or (ii) transcription factors which control the expression of the transmembrane transporters of the PDR subfamily, or else (iii) transmembrane transporters of the MFS family; in particular from (i) transmembrane transporters of the ABC family from yeasts, in particular transmembrane transporters of the PDR subfamily from yeasts, or (ii) transcription factors which control the expression of the transmembrane transporters of the PDR subfamily from yeasts, or else (iii) transmembrane transporters of the MFS family from yeasts, in particular those from *Saccharomyces* yeasts, even more particularly of the *Saccharomyces cerevisiae* species, as means for reducing in vivo phloroglucinol toxicity.

Advantageously, said polypeptide comprises at least one amino acid sequence having at least 70% identity with a sequence selected from SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32 and SEQ ID No. 33.

Advantageously, said polypeptide is selected from yeast PDR transporters, transcription factors which regulate the expression of yeast PDR transporters, and yeast MFS transporters, said yeast being in particular selected from yeasts of the *Saccharomyces* genus, and more particularly from the species *Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa* and *Torulaspora glabrata*; even more particularly, said yeast being of the *Saccharomyces cerevisiae* species.

According to one embodiment, said polypeptide comprises at least one amino acid sequence preferably having at least 70% identity, more preferably at least 75% identity, more preferably at least 80% identity, even more preferably at least 85% identity, still more preferably at least 90% identity, even more preferentially at least 95% identity, even more preferentially at least 96% identity, more preferably at least 97% identity, more preferably at least 98% identity, even more preferably at least 99% identity, preferably among all 100% identity, with a sequence selected from SEQ ID No. 1, SEQ ID No. 2, SEQ ID No. 3, SEQ ID No. 4, SEQ ID No. 5, SEQ ID No. 6, SEQ ID No. 7, SEQ ID No. 8, SEQ ID No. 9, SEQ ID No. 10, SEQ ID No. 11, SEQ ID No. 12, SEQ ID No. 13, SEQ ID No. 14, SEQ ID No. 15, SEQ ID No. 16, SEQ ID No. 17, SEQ ID No. 18, SEQ ID No. 19, SEQ ID No. 20, SEQ ID No. 21, SEQ ID No. 22, SEQ ID No. 23, SEQ ID No. 24, SEQ ID No. 25, SEQ ID No. 26, SEQ ID No. 27, SEQ ID No. 28, SEQ ID No. 29, SEQ ID No. 30, SEQ ID No. 31, SEQ ID No. 32 and SEQ ID No. 33. According to one particularly advantageous embodiment, said polypeptide comprises at least one amino acid sequence selected from SEQ ID No. 2, SEQ ID No. 10, SEQ ID No. 14, SEQ ID No. 15, SEQ ID No. 16, SEQ ID No. 17, SEQ ID No. 19, SEQ ID No. 26 and SEQ ID No. 27.

In one preferred embodiment, the isolated polypeptide capable of conferring on the living cell resistance with respect to phloroglucinol-induced toxicity has an amino acid sequence preferably having at least 70% identity, more preferably at least 75% identity, more preferably at least 80% identity, even more preferably at least 85% identity, still more preferably at least 90% identity, even more preferentially at least 95% identity, even more preferentially at least 96% identity, more preferably at least 97% identity, more preferably at least 98% identity, even more preferably at least 99% identity, preferably among all 100% identity, with SEQ ID No. 2, SEQ ID No. 10, SEQ ID No. 14, SEQ ID No. 15, SEQ ID No. 16, SEQ ID No. 17, SEQ ID No. 19, SEQ ID No. 26 or SEQ ID No. 27. In a more preferred embodiment, the isolated polypeptide capable of conferring on the living cell resistance with respect to phloroglucinol-induced toxicity has an amino acid sequence preferably having at least 70% identity, more preferably at least 75% identity, more preferably at least 80% identity, even more preferably at least 85% identity, still more preferably at least 90% identity, even more preferentially at least 95% identity, even more preferentially at least 96% identity, more preferably at least 97% identity, more preferably at least 98% identity, even more preferably at least 99% identity, preferably among all 100% identity, with SEQ ID No. 2.

Isolated Nucleic Acids

The present invention uses isolated nucleic acid molecules encoding at least one polypeptide selected from the transporters of the PDR subfamily, the transcription factors which control the expression of the transporters of the PDR subfamily, and the transporters of the MFS family, in particular those from yeasts, in particular those from *Saccharomyces* yeasts, more particularly those from *Saccharomyces cerevisiae*.

Advantageously, said polypeptide is as defined above.

Thus, the present invention uses isolated nucleic acid molecules encoding at least one isolated polypeptide selected from SNQ2, STE6, PDR3, AQR1, DTR1, FLR1, QDR1, YHK8 and ATR1, and preferably SNQ2.

The present invention thus uses isolated nucleic acid molecules encoding at least one isolated polypeptide having an amino acid sequence selected from SEQ ID No. 2, SEQ ID No. 10, SEQ ID No. 14, SEQ ID No. 15, SEQ ID No. 16, SEQ ID No. 17, SEQ ID No. 19, SEQ ID No. 26 and SEQ ID No. 27, preferably SEQ ID No. 2.

In one embodiment, the present invention uses isolated nucleic acid molecules encoding at least one isolated polypeptide, the amino acid sequence of which preferably has at least 70% identity, more preferably at least 75% identity, more preferably at least 80% identity, even more preferably at least 85% identity, still more preferably at least 90% identity, even more preferentially at least 95% identity, even more preferentially at least 96% identity, more preferably at least 97% identity, more preferably at least 98% identity, even more preferably at least 99% identity, preferably among all 100% identity, with SEQ ID No. 2, SEQ ID No. 10, SEQ ID No. 14, SEQ ID No. 15, SEQ ID No. 16, SEQ ID No. 17, SEQ ID No. 19, SEQ ID No. 26 or SEQ ID No. 27, preferably SEQ ID No. 2.

According to one embodiment, the isolated nucleic acid molecule comprises a promoter which controls the expression of at least one nucleic acid sequence encoding a polypeptide as defined above. Thus, according to one embodiment, the isolated nucleic acid molecule comprises at least one nucleic acid sequence encoding a polypeptide selected from (i) transmembrane transporters of the ABC family, in particular transmembrane transporters of the PDR subfamily, (ii) transcription factors which control the expression of the transmembrane transporters of the PDR subfamily, and (iii) transmembrane transporters of the MFS family, as defined above, and also comprises a promoter which controls the expression of at least one, preferably of said, nucleic acid sequence. According to one preferred embodiment, the isolated nucleic acid molecule comprises at least one nucleic acid sequence encoding a polypeptide selected from SNQ2, STE6, PDR3, AQR1, DTR1, FLR1, QDR1, YHK8 and ATR1, preferably SNQ2, and also comprises a promoter which controls the expression of at least one, preferably of said, nucleic acid sequence.

Advantageously, the promoter is an exogenous promoter, in particular a yeast promoter, preferably a promoter selected from ADH2 (pADH2) and CCW12 (pCCW12), more preferably a promoter selected from ADH2 (pADH2) of Saccharomyces cerevisiae (S. cerevisiae) and CCW12 (pCCW12) of S. cerevisiae, more preferably the CCW12 promoter of SEQ ID No. 34.

According to one embodiment, the isolated nucleic acid molecule comprises a transcription terminator for at least one nucleic acid sequence encoding a polypeptide as defined above. Thus, according to one embodiment, the isolated nucleic acid molecule comprises at least one nucleic acid sequence encoding a polypeptide selected from (i) transmembrane transporters of the ABC family, in particular transmembrane transporters of the PDR subfamily, (ii) transcription factors which control the expression of the transmembrane transporters of the PDR subfamily, and (iii) transmembrane transporters of the MFS family, as defined above, and also comprises a terminator which controls the expression of at least one, preferably of said, nucleic acid sequence. According to one preferred embodiment, the isolated nucleic acid molecule comprises at least one nucleic acid sequence encoding a polypeptide selected from SNQ2, STE6, PDR3, AQR1, DTR1, FLR1, QDR1, YHK8 and ATR1, preferably SNQ2, and also comprises a terminator which controls the expression of at least one, preferably of said, nucleic acid sequence.

Advantageously, the terminator is an exogeneous terminator, in particular a yeast terminator, preferably the RPL3 terminator (tRPL15A), more preferably the RPL15A terminator of S. cerevisiae, more preferably the RPL15A terminator of SEQ ID No. 35.

According to one embodiment, the isolated nucleic acid molecule comprises both a promoter and a terminator which are as defined above. Thus, according to one embodiment, the isolated nucleic acid molecule comprises at least one nucleic acid sequence encoding a polypeptide selected from (i) transmembrane transporters of the ABC family, in particular transmembrane transporters of the PDR subfamily, (ii) transcription factors which control the expression of the transmembrane transporters of the PDR subfamily, and (iii) transmembrane transporters of the MFS family, as defined above, and also comprises a promoter and a terminator which control the expression of at least one, preferably of said, nucleic acid sequence.

According to one preferred embodiment, the isolated nucleic acid molecule comprises at least one nucleic acid sequence encoding a polypeptide selected from SNQ2, STE6, PDR3, AQR1, DTR1, FLR1, QDR1, YHK8 and ATR1, preferably SNQ2, and also comprises a promoter and a terminator which control the expression of said at least one nucleic acid sequence.

According to one embodiment, the nucleic acid molecule is isolated from homologous strains, in culture, in particular from strains selected from the yeasts of the Saccharomyces genus, preferably selected from Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa and Torulaspora glabrata; even more particularly, the yeast of the Saccharomyces cerevisiae species.

According to one embodiment, the nucleic acid molecule is isolated from a vector or from a host cell comprising said molecule, said vector or said host cell being as defined above and as described hereinafter in the sections "Host cells" or "Vectors".

According to one embodiment, the isolated nucleic acid molecule is synthesized in-vitro by nucleic synthesis techniques that those skilled in the art are fully aware of or will know how to determine without difficulty from their general knowledge.

According to one embodiment, the isolated nucleic acid molecule is recombinant.

Vectors

The present invention uses vectors comprising at least one nucleic acid molecule as defined above. Advantageously, the vector is a plasmid.

The vectors that are suitable in the context of the present invention comprise, without limitation, bacteriophage, plasmid or cosmid vectors for expression in prokaryotic host cells such as bacteria (for example E. coli, or bacteria of the Pseudomonas genus); vectors for expression in yeast (for example Saccharomyces cerevisiae, Schyzosaccharomyces pombe, Pichia pastoris); baculovirus vectors for expression in insect cell systems (for example Sf9 cells); viral and plasmid vectors for expression in plant cell systems (for example the Ti plasmid, the cauliflower mosaic virus, CaMV, the tobacco mosaic virus TMV); and also viral and plasmid vectors for expression in higher eukaryotic cells or organisms.

The vectors that are suitable in the context of the present invention may be of integrating type or of replicating type. Vectors of integrating type do not have a sequence referred to as "origin of replication" and must thus be integrated directly into the genome of the host cell in order to be expressed. This integration can be carried out by means of dedicated genetic tools well known to those skilled in the art. By way of non-limiting example, this integration can be carried out by homologous recombination or else via the CRE-LOX recombination system. Vectors of replicating type have an origin of autonomous replication. These vectors thus replicate independently with respect to the host cell genome. Thus, contrary to integrating vectors, replicating vectors do not need to be integrated into the host cell genome.

These vectors are generally commercially available (for example, from suppliers such as Invitrogen, Stratagene, Amersham Biosciences, Promega, etc.), available from depositing institutions such as American Type Culture Collection (ATCC, Rockville, Md.), or have been the subject of numerous publications describing their sequence, their structures and their methods of production, so that those skilled in the art can apply them without difficulty.

Representative examples of suitable plasmid vectors include, without limitation, pREP4, pCEP4, (Invitrogen), pCI (Promega), pYES2 (ThermoFisher) and pgWiz (Gene Therapy System Inc).

Host Cells

The present invention relates to host cells that are phloroglucinol resistant because they comprise at least one nucleic acid molecule or at least one vector as defined above.

According to various embodiments, said host cell may be a prokaryotic cell, a lower eukaryotic cell such as a yeast cell, and another eukaryotic cell such as an insect cell, a plant cell and a mammalian cell (for example human or non-human, preferably non-human).

Advantageously, the host cell is a microorganism selected from bacteria, yeasts, fungi, algae and cyanobacteria.

The host cell is preferably a yeast, said yeast being in particular selected from the genera *Saccharomyces, Candida, Ashbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* and *Malassezia.*

Even more particularly, the yeast is selected from the species *Saccharomyces cerevisiae, Saccharomyces boulardii, Saccharomyces douglasii, Saccharomyces bayanus, Zigosaccharomyces bairn, Schizosaccharomyces pombe, Dekkera brucelensis, Dekkera intermedia, Brettanomycces custersii, Brettanomycces intermedius, Kluyveromyces themotolerens, Torulaspora globosa* and *Torulaspora glabrata.*

Even more particularly, the yeast is of the *Saccharomyces* genus, preferably of the *Saccharomyces cerevisiae* species.

According to one embodiment, the host cell comprises at least one copy of the nucleic acid molecule as defined above, integrated into its genome.

According to one embodiment, the host cell comprises a single copy of the nucleic acid molecule as defined above, integrated into its genome.

Thus, the present invention relates to a host cell comprising at least one copy of a nucleic acid molecule encoding a polypeptide selected from SNQ2, STE6, PDR3, AQR1, DTR1, FLR1, QDR1, YHK8 and ATR1, preferably SNQ2.

The present invention relates to a host cell comprising at least one copy of a nucleic acid molecule encoding a polypeptide having an amino acid sequence selected from SEQ ID No. 2, SEQ ID No. 10, SEQ ID No. 14, SEQ ID No. 15, SEQ ID No. 16, SEQ ID No. 17, SEQ ID No. 19, SEQ ID No. 26 and SEQ ID No. 27, preferably SEQ ID No. 2.

In one embodiment, the present invention relates to a host cell comprising at least one copy of a nucleic acid molecule encoding a polypeptide having an amino acid sequence preferably having at least 70% identity, more preferably at least 75% identity, more preferably at least 80% identity, even more preferably at least 85% identity, still more preferably at least 90% identity, even more preferentially at least 95% identity, even more preferentially at least 96% identity, more preferably at least 97% identity, more preferably at least 98% identity, even more preferably at least 99% identity, preferably among all 100% identity, with SEQ ID No. 2, SEQ ID No. 10, SEQ ID No. 14, SEQ ID No. 15, SEQ ID No. 16, SEQ ID No. 17, SEQ ID No. 19, SEQ ID No. 26 or SEQ ID No. 27, preferably SEQ ID No. 2.

When the host cell is a yeast cell, the copy or copies of the nucleic acid molecule can be integrated at different loci, preferentially at the URA3 locus, at the JLP1 locus, at the LEU2 locus, at the SAM2 locus, at the MET14 locus, and/or at the TRP1 locus of the genome of said yeast cell. When the host cell is a yeast cell and several copies of the nucleic acid molecule are integrated, the various copies can be integrated at the same locus, or else at different loci, preferentially at any one of the combinations of the URA3, JLP1, LEU2, SAM2, MET14 and/or TRP1 loci.

Preferably, the copy or copies of the nucleic acid molecule is (are) integrated at the JLP1 locus. Advantageously, the codons used in the nucleic acid molecule have been adapted for an optimal expression in the host cell selected.

An optimal expression can in particular be obtained when the codons selected are those preferentially used by the organism of origin of the host cell. The codons preferentially used are known for most organisms commonly used in the field. Those skilled in the art will be able to easily determine the most advantageous codons to be used as a function of the host cell chosen. To this effect, those skilled in the art know which technique to use in order to modify the codons of the nucleic acid molecule. The codons may be for example modified by in vitro site directed mutagenesis using a sample of the nucleic acid molecule of which the codons are to be adapted, by means of a polymerase chain reaction (PCR) amplification. Alternatively, the nucleic acid molecule can be synthesized in vitro directly with the optimized codons.

The host cells can be cultured in aerobic or anaerobic bioreactors, on a small and large scale, in flasks or Petri dishes. The culturing can be carried out at a temperature, at a pH, in a culture medium and at an oxygen content that are suitable for a given host cell.

Advantageously, the host cells as described above can be cultured in media comprising high phloroglucinol concentrations, in particular concentrations greater than or equal to 1 g·l$^{-1}$, preferably greater than or equal to 2.5 g·l$^{-1}$, preferably greater than or equal to 5 g·l$^{-1}$, preferably greater than or equal to 7.5 g·l$^{-1}$, preferably greater than or equal to 10 g·l$^{-1}$, preferably greater than or equal to 15 g·l$^{-1}$, and more preferably greater than or equal to 20 g·l$^{-1}$.

Thus, in one advantageous embodiment, the host cell comprises at least one copy of a nucleic acid molecule encoding a polypeptide of which an amino acid sequence has at least 70% identity, more preferably at least 75% identity, more preferably at least 80% identity, even more preferably at least 85% identity, still more preferably at least 90% identity, even more preferentially at least 95% identity, even more preferentially at least 96% identity, more preferably at least 97% identity, more preferably at least 98% identity, even more preferably at least 99% identity, preferably among all 100% identity, with SEQ ID No. 2. This host cell exhibits phloroglucinol resistance; it can in particular be cultured in media comprising high phloroglucinol concentrations, in particular a phloroglucinol concentration greater than or equal to 20 g·l$^{-1}$.

Thus, in one particularly advantageous embodiment, the host cell comprises at least one copy of a nucleic acid molecule encoding a polypeptide having the amino acid sequence of the membrane transporter of the PDR subfamily: SNQ2. This host cell exhibits phloroglucinol resistance; it can in particular be cultured in media comprising high phloroglucinol concentrations, in particular a phloroglucinol concentration greater than or equal to 20 g·l$^{-1}$.

In one particular embodiment, the invention relates to a living cell, or respectively a host cell, as defined above, characterized in that it expresses, respectively overexpresses, at least one enzyme involved in phloroglucinol biosynthesis, preferably at least one type III polyketide synthase, more preferentially at least one phloroglucinol synthase.

To this end, use may in particular be made of any known sequence encoding a type III polyketide synthase, preferably any known sequence encoding a phloroglucinol synthase, in particular that encoded by the PHLD gene in *Pseudomonas fluorescens* (Achkar et al., 2005; Zha et al., 2006) or else that encoded by the PKS1 gene in Ectocarpus siliculosus (Meslet-Cladiere et al., 2013). Use may also be made of the sequences described in International Patent Applications WO 2019/002798 and WO 2019/002799.

Those skilled in the art will know how to adjust the means and methods developed above for the purposes of expressing or overexpressing said at least one enzyme involved in phloroglucinol biosynthesis and preferably a phloroglucinol synthase.

Method for Obtaining a Phloroglucinol-Resistant Host Cell and Use

The present invention also relates to a method for obtaining a phloroglucinol-resistant host cell. According to one embodiment, the method for obtaining a phloroglucinol-resistant recombinant host cell comprises at least the steps of:
i. providing a nucleic acid molecule which comprises at least one nucleic acid sequence encoding a polypeptide selected from the membrane transporters of the ABC family, preferably of the PDR subfamily, and the membrane transporters of the MFS family, or which comprises at least one nucleic acid sequence encoding a transcription factor which controls the expression of a membrane transporter of the PDR subfamily,
ii. cloning said nucleic acid molecule provided in step (i) in a vector capable of allowing the integration and/or the expression of said molecule in said host cell, and
iii. bringing said host cell and said vector obtained in step (ii) into contact so that said host cell is transfected with said vector and that said host cell expresses said nucleic acid molecule, said host cell thus being phloroglucinol resistant.

According to one preferred embodiment, said polypeptide provided in step (i) is selected from SNQ2, STE6, PDR3, AQR1, DTR1, FLR1, QDR1, YHK8 and ATR1.

According to a more preferred embodiment, said polypeptide provided in step (i) is SNQ2.

According to one advantageous embodiment, said polypeptide provided in step (i) comprises at least one amino acid sequence having at least 70% identity, more preferably at least 75% identity, more preferably at least 80% identity, even more preferably at least 85% identity, still more preferably at least 90% identity, even more preferentially at least 95% identity, even more preferentially at least 96% identity, more preferably at least 97% identity, more preferably at least 98% identity, even more preferably at least 99% identity, preferably among all 100% identity, with SEQ ID No. 2.

In one embodiment, said nucleic acid molecule is not integrated in step (iii) into the genome of said host cell.

In an alternative and preferred embodiment, said nucleic acid molecule is integrated in step (iii) into the genome of said host cell.

According to one particular embodiment, the method for obtaining a phloroglucinol-resistant recombinant host cell is characterized in that said host cell also overexpresses at least one enzyme involved in phloroglucinol biosynthesis, preferably a type III polyketide synthase, even more preferentially at least one phloroglucinol synthase.

Thus, the method for obtaining a phloroglucinol-resistant recombinant host cell comprises at least the steps of:
i. providing a nucleic acid molecule which comprises at least one nucleic acid sequence encoding a polypeptide selected from the membrane transporters of the ABC family, preferably of the PDR subfamily, and the membrane transporters of the MFS family, or comprises at least one nucleic acid sequence encoding a transcription factor which controls the expression of a membrane transporter of the PDR subfamily,
ii. providing a nucleic acid molecule comprising at least one nucleic acid sequence encoding a type III polyketide synthase, in particular a type III polyketide synthase having phloroglucinol synthase activity,
iii. cloning said nucleic acid molecules provided in steps (i) and (ii) in at least one vector capable of allowing the integration and/or the expression of said molecules in said host cell, and
iv. bringing said host cell and said at least one vector obtained in step (iii) into contact so that said host cell is transfected by said vector(s) and that said host cell expresses said nucleic acid molecules, said host cell thus being phloroglucinol resistant.

According to one preferred embodiment, said polypeptide provided in step (i) is selected from SNQ2, STE6, PDR3, AQR1, DTR1, FLR1, QDR1, YHK8 and ATR1.

According to a more preferred embodiment, said polypeptide provided in step (i) is SNQ2. According to one advantageous embodiment, said polypeptide provided in step (i) comprises at least one amino acid sequence having at least 70% identity, more preferably at least 75% identity, more preferably at least 80% identity, even more preferably at least 85% identity, still more preferably at least 90% identity, even more preferentially at least 95% identity, even more preferentially at least 96% identity, more preferably at least 97% identity, more preferably at least 98% identity, even more preferably at least 99% identity, preferably among all 100% identity, with SEQ ID No. 2.

In one embodiment, the nucleic acid molecules provided in steps (i) and (ii) are cloned in step (iii) in one and the same vector.

In a distinct and alternative embodiment, the nucleic acid molecules provided in steps (i) and (ii) are cloned in step (iii) in two different vectors.

In one embodiment, said nucleic acid molecules are not integrated in step (iv) into the genome of said host cell.

In one embodiment, at least one of said nucleic acid molecules is integrated in step (iv) into the genome of said host cell.

In an alternative and preferred embodiment, said nucleic acid molecules are integrated in step (iv) into the genome of said host cell.

Advantageously, the host cell is a microorganism selected from bacteria, yeasts, fungi, algae and cyanobacteria.

The host cell is preferably a yeast, said yeast being in particular selected from the genera *Saccharomyces, Candida*, Ashbya, Dekkera, *Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* and *Malassezia*.

Even more particularly, the yeast is selected from the species *Saccharomyces cerevisiae, Saccharomyces boulardii, Saccharomyces douglasii, Saccharomyces bayanus, Zigosaccharomyces bairn, Schizosaccharomyces pombe,*

Dekkera brucelensis, Dekkera intermedia, Brettanomycces custersii, Brettanomycces intermedius, Kluyveromyces themotolerens, Torulaspora globosa and Torulaspora glabrata.

Even more particularly, the yeast is of the Saccharomyces genus, preferably of the Saccharomyces cerevisiae species.

Also described herein is the use of a living cell, preferably of a host cell as defined above or of a host cell resulting from the method for obtaining said host cell described above, for the production of phloroglucinol.

Advantageously, the host cell is a microorganism selected from bacteria, yeasts, fungi, algae and cyanobacteria.

The host cell is preferably a yeast, said yeast being in particular selected from the genera Saccharomyces, Candida, Ashbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus and Malassezia.

Even more particularly, the yeast is selected from the species Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa and Torulaspora glabrata.

Even more particularly, the yeast is of the Saccharomyces genus, preferably of the Saccharomyces cerevisiae species.

Method for Producing Phloroglucinol

Another subject of the invention relates to a method for producing phloroglucinol, comprising at least the steps:
i. of obtaining a host cell by carrying out a method of production as defined above,
ii. of bringing said host cell into contact with an appropriate substrate,
iii. of incubating the mixture obtained in step (ii) under conditions suitable for producing phloroglucinol; and
iv. optionally, of recovering the reaction medium comprising the phloroglucinol obtained after step (iii) and of purifying the phloroglucinol.

Advantageously, the host cell is as described above. In one preferred embodiment, it is in particular a yeast cell, in particular of the Saccharomyces genus and preferably of the Saccharomyces cerevisiae species.

Those skilled in the art, by virtue of their general knowledge, will know how to identify the culture conditions suitable for producing phloroglucinol according to step (iii). They will in particular know how to adjust the temperature, the pH, the amounts of $O_2$ and $CO_2$ and other parameters, as a function of the cell type used in implementing the method of production described above.

In particular, for the purposes of the production method described above, the substrate is a carbon source. Advantageously, the carbon source is a pure carbon source or an industrial coproduct (such as molasses or green syrup, for example from the sugar industry). Preferably, the substrate in the pure carbon source or the industrial coproduct is a simple sugar, such as glucose (or dextrose), fructose, galactose, mannose, sucrose, lactose or maltose; a complex sugar, such as a monosaccharide, a disaccharide or a trisaccharide, or else a polysaccharide such as starch; an alcohol, such as ethanol; an acid; a fatty acid and the ester derivative thereof; or a mixture of sugars, alcohols, acids and/or fatty acids or the ester derivatives thereof.

Preferably, the substrate is glucose or sucrose. Alternatively, the substrate is ethanol.

The examples which follow serve to illustrate the present invention without any limitation.

EXAMPLES

Example 1: Method for Assaying Phloroglucinol

The method for assaying phloroglucinol was developed as detailed below. It comprises in particular a step of extracting the phloroglucinol, followed by a step of assaying by chromatography.

1.1 Phloroglucinol Extraction

The method was developed by using resorcinol as internal standard (IS). Various tests led to the development of a method of liquid-liquid extraction carried out at pH 4.0 in the presence of ethyl acetate as solvent, and with the aqueous phase being saturated with NaCl. The extraction is carried out for 30 min with circular shaking. The organic phase is removed and the ethyl acetate solvent is evaporated off under a stream of nitrogen $N_2$ at 30° C. The dry extract obtained after complete evaporation is then taken up in a given volume of a 50%-50% ethanol/$H_2O$ mixture.

The extraction yield (YLD) was measured by mass spectroscopy after high pressure chromatography on a C18 column (dimensions: 100 mm×2.1 mm; particle size: 1.7 µm) using a 0.03% methanoic acid (HCOOH)/acetonitrile (ACN) gradient.

The YLDs were determined using solutions of phloroglucinol and resorcinol, prepared in the culture medium used for the growth of the yeasts. The phloroglucinol concentrations correspond to the low (20 µg·ml$^{-1}$) and high (200 µg·ml$^{-1}$) points of the assay range. The resorcinol concentration corresponds to the concentration added as internal standard during the assays (200 µg·ml$^{-1}$). The results are shown in Table 1.

TABLE 1

Extraction yield (YLD) of phloroglucinol (20 and 200 µg · ml$^{-1}$) and of resorcinol (200 µg · ml$^{-1}$), extracted with ethyl acetate, according to the method described.

| Product | Phloroglucinol | | Resorcinol (IS) |
|---|---|---|---|
| Phloroglucinol or resorcinol concentration in the culture medium (µg · ml$^{-1}$) | 20 | 200 | 200 |
| YLD (%) | 76 | 89 | 82 |

1.2 Chromatography Measurement Method: A UPLC/UV and UPLC/MS Analysis Method

A method of analysis by UPLC chromatography and measurement of absorbance by UV (ultraviolet radiation) was developed. The extract is subjected to chromatography on a propyl-pentafluorophenyl (PFP) column having dimensions of 100 mm×2.1 mm; particle size: 1.8 µm according to a gradient of 0.1% HCOOH/ACN—0.1% HCOOH. The phloroglucinol is detected by UV at 230 nm. A UPLC-mass spectrometry (UPLC/Mass) method was also developed.

The quantification is carried out using a range of 20 to 200 µg·ml$^{-1}$ of phloroglucinol diluted in yeast culture medium (Yeast Extract 1%, BactoPeptone 2%) in the presence of a fixed amount of resorcinol, used as internal control. The amount of phloroglucinol is determined by calculating the ratios of the areas of the phloroglucinol/resorcinol chromatography peaks.

This assay method thus makes it possible to reliably measure, qualitatively and quantitatively, the phloroglucinol present in a culture medium.

Example 2: Evaluation of the Toxicity of Phloroglucinol on the Bacterial or Yeast Cells In order to know the threshold of phloroglucinol tolerance of bacteria or of yeasts, growth kinetics were prepared in the presence of various concentrations of phloroglucinol. These preliminary experiments aimed to evaluate their $EC_{50}$.

The experiment was carried out in the following way. The phloroglucinol was dissolved at the concentration of 15 g·l$^{-1}$ in complete medium (Yeast Extract 1%+BactoPeptone 2%) containing 2% glucose as carbon source (YPD medium). The culture media containing lower phloroglucinol concentrations were obtained by diluting this first medium in the same YPD medium containing 2% glucose.

In order to carry out the experiment, the wild-type yeast or bacterial cells were inoculated at an $OD_{600\,nm}$ of 0.05 into the various media, thus containing, as soon as the cultures were started, either 0 (positive control for growth indicated C+), 1, 2.5, 5, 7.5, 10 or 15 g·l$^{-1}$ of phloroglucinol. The cultures were carried out in 48-well microplates, at 28° C. for the yeasts, at 37° C. for the bacterial strain, with vigorous shaking for 24 h. Two yeast strains (*Saccharomyces cerevisiae*) and one bacterial strain (*Escherichia coli*) were tested. The results obtained are presented below.

2.1 Results in the Bacterium

The results demonstrate that the $EC_{50}$ of phloroglucinol on a bacterial strain of *Escherichia coli* is around 0.75 g·l$^{-1}$, very considerable inhibition of the growth being observed as early as the concentration of 1 g·l$^{-1}$, total inhibition of the growth being measured for all the concentrations greater than or equal to 2.5 g·l$^{-1}$ (FIG. 1).

2.2 Results in the Yeast

The results demonstrate that the $EC_{50}$ of phloroglucinol on the CC787-1B yeast strain is greater than 10 g·l$^{-1}$, significant inhibition of the growth of the yeast cells being observed only in the medium containing 15 g·l$^{-1}$ of phloroglucinol (FIG. 2).

2.3 Continuation of the Toxicity Studies in the Presence of Ethanol

During the method for producing phloroglucinol by the yeast, it is possible for ethanol to be a coproduct depending on the fermentative system selected for this method. Ethanol is capable of increasing the soluble fraction of phloroglucinol in the growth medium and is therefore capable of increasing the toxicity of phloroglucinol with respect to yeast cells. The toxicity of phloroglucinol in the presence of ethanol added after 20 h of culture was tested.

The experiments were carried out in an Erlenmeyer flask with vigorous stirring in complete medium containing 2% glucose as carbon source. The yeast cells were inoculated at an $OD_{600\,nm}$ of 0.05 from precultures in complete medium. The cultures are completed with increasing concentrations of phloroglucinol (0, 1, 5, 10, 15, 20 g/l) and incubated for 48 h. Two series of Erlenmeyer flasks were prepared. In the second series, 50 g·l$^{-1}$ of ethanol are added at 20 h. The growth is monitored by taking samples at 18 h, 20 h, 22 h, 24 h, 42 h and 48 h, and measuring the $OD_{600\,nm}$. The results obtained are presented below.

Under these conditions, two effects are observed (FIGS. 3A and 3B):

a. In the YPDA culture without phloroglucinol, the addition of ethanol at 20 h induces a break in the growth curve linked to the change in metabolic regime, then the ethanol consumed is used as carbon source, resulting in an $OD_{600\,nm}$ at 48 h greater than that without ethanol.

b. In the presence of ethanol, the phloroglucinol inhibition is slightly greater at 48 h, in the presence of 20 g/l of phloroglucinol.

Example 3: Overexpression of PDRs and Measurement of the Effect on the Phloroglucinol tolerance of the yeasts 3.1 Integration of Genes Encoding the Various PDRs in the *Saccharomyces cerevisiae* Yeast The genes encoding the PDR proteins were amplified from yeast (W303-1A) genomic DNA by PCR ("polymerase chain reaction") and cloned in plasmids. The accuracy of the sequence was verified by sequencing. The various genes encoding the PDRs were integrated into the genome at the JLP1 locus according to the structure described in FIG. 4A. Each strain constructed bears a YA number, and a library of 28 yeast strains overexpressing a PDR transporter was thus created, in a proportion of two clones per transporter.

TABLE 2

Protein sequences of the PDR membrane transporters and transcription factors cloned

| Protein | NCBI Ref. | SEQ ID No. |
|---|---|---|
| PDR5 | NP_014796.3 | SEQ ID No. 1 |
| SNQ2 | NP_010294.1 | SEQ ID No. 2 |
| PDR10 | PTN22535.1 | SEQ ID No. 3 |
| PDR11 | NP_012252.1 | SEQ ID No. 4 |
| PDR 12 | NP_015267.1 | SEQ ID No. 5 |
| PDR15 | NP_010694.1 | SEQ ID No. 6 |
| PDR18 | NP_014468.3 | SEQ ID No. 7 |
| ADP1 | NP_009937.2 | SEQ ID No. 8 |
| AUS1 | NP_014654.1 | SEQ ID No. 9 |
| STE6 | NP_012713.1 | SEQ ID No. 10 |
| YOL075C | NP_014567.2 | SEQ ID No. 11 |
| YOR1 | NP_011797.3 | SEQ ID No. 12 |
| PDR1 | NP_011502.1 | SEQ ID No. 13 |
| PDR3 | NP_009548.1 | SEQ ID No. 14 |

TABLE 3

Nucleotide sequences of the promoters and terminators used for the clonings

| Name | SEQ ID No. |
|---|---|
| pCCW12 | SEQ ID No. 34 |
| tRPL15A | SEQ ID No. 35 |

3.2 Effect of PDR Overexpression on the Phloroglucinol Tolerance of the Strains

In order to test the impact of the PDR overexpression on the phloroglucinol tolerance at high phloroglucinol concentration (>15 g·l$^{-1}$), the strains were cultured as follows.

The phloroglucinol was dissolved at the concentration of 20 g·l$^{-1}$ in YPD medium containing 2% glucose as carbon source. In order to carry out the experiment, the yeasts expressing each PDR were inoculated at an $OD_{600\,nm}$ of 0.05. The cultures were carried out in 48-well microplates, incubated with agitation at 28° C. for 24 h. After 24 h, the $OD_{600\,nm}$ is measured. FIG. 5 represents the $OD_{600\,nm}$ values obtained at the end of the culture.

The results clearly show that, among all the PDRs tested, only the overexpression of SNQ2 makes it possible to lift the toxicity of phloroglucinol when it is present in the medium in an amount of 20 g·l$^{-1}$. The results are confirmed in the two clones isolated YA2786-1 and YA2786-2. Moreover, the overexpression of PDR3 and also of STE6 makes it possible, for at least one of the two clones of each transgenic line, to increase the phloroglucinol resistance of the yeasts compared to the corresponding non-transgenic line. With regard to the other members of the PDR subfamily tested herein, it is noted that their overexpression has no impact on the growth of the yeast. Thus, the results indicate that phloroglucinol is a substrate for SNQ2. Little data is available in the literature regarding the spectrum of molecules transported by SNQ2.

The experiments were repeated according to the same protocol in the presence of 40 g·l$^{-1}$ of ethanol. The results obtained were comparable to those presented in FIG. 5. The addition of ethanol (40 g·l$^{-1}$) which increases the soluble fraction of phloroglucinol in the medium has no impact on the phloroglucinol resistance conferred by the overexpression of SNQ2.

Example 4: Overexpression of MFSs and Measurement of the Effect on the Phloroglucinol Tolerance of the Yeasts 4.1 Integration of the Genes Encoding the Various MFSs in the *Saccharomyces cerevisiae* Yeast The genes encoding the MFS proteins were amplified from yeast (W303-1A) genomic DNA by PCR ("polymerase chain reaction") and cloned in plasmids. The accuracy of the sequence was verified by sequencing. The various genes encoding the MFSs were integrated into the genome at the JLP1 locus according to the structure described in FIG. 6A. Each strain constructed bears a YA number, and a library of 38 yeast strains overexpressing an MFS transporter was thus created, in a proportion of two clones per transporter.

TABLE 4

Protein sequences of the MFS membrane transporters cloned

| Protein | NCBI Ref. | SEQ ID No. |
| --- | --- | --- |
| AQR1 | NP_014334.3 | SEQ ID No. 15 |
| DTR1 | NP_009739.1 | SEQ ID No. 16 |
| FLR1 | NP_009562.1 | SEQ ID No. 17 |
| HOL1 | NP_014453.3 | SEQ ID No. 18 |
| QDR1 | KZV10493.1 | SEQ ID No. 19 |
| QDR2 | EGA61893.1 | SEQ ID No. 20 |
| QDR3 | NP_009599.2 | SEQ ID No. 21 |
| TPO1 | NP_013072.1 | SEQ ID No. 22 |
| TPO2 | AJS07311.1 | SEQ ID No. 23 |
| TPO3 | NP_015482.1 | SEQ ID No. 24 |
| TPO4 | NP_014916.1 | SEQ ID No. 25 |
| YHK8 | NP_011914.1 | SEQ ID No. 26 |
| ATR1 | NP_013591.1 | SEQ ID No. 27 |
| GEX1 | NP_009863.2 | SEQ ID No. 28 |
| AZR1 | NP_011740.3 | SEQ ID No. 29 |
| SGE1 | NP_015524.1 | SEQ ID No. 30 |
| SIT1 | NP_010849.3 | SEQ ID No. 31 |
| ENB1 | NP_014484.1 | SEQ ID No. 32 |
| GEX2 | NP_013032.1 | SEQ ID No. 33 |

4.2 Effect of the Overexpression of the MFSs on the Phloroglucinol Tolerance of the Strains In order to test the impact of the overexpression of the MFSs on the phloroglucinol tolerance at high phloroglucinol concentration (>15 g·l$^{-1}$), the strains were cultured as follows.

The phloroglucinol was dissolved at the concentration of 20 g·l$^{-1}$ in YPD medium containing 2% glucose as carbon source. In order to carry out the experiment, the yeasts expressing each MFS were inoculated at an OD$_{600\ nm}$ of 0.05. The cultures were carried out in 48-well microplates, incubated with agitation at 28° C. for 24 h. After 24 h, the OD$_{600\ nm}$ is measured. FIG. 7 represents the OD$_{600\ nm}$ values obtained at the end of the culture.

The results clearly show that, among all the MFS transporters tested, the overexpression of AQR1, DTR1, FLR1, QDR1, YHK8 and also ATR1 makes it possible, for each of the two clones of each transgenic line, to considerably increase the phloroglucinol resistance of the yeasts compared with the corresponding non-transgenic line. With regard to the other members of the PDR subfamily tested herein, it is noted that their overexpression has no impact on the growth of the yeast.

Contrary to what was observed for the PDR transporters, none of the MFS transporters tested makes it possible to totally lift the phloroglucinol toxicity.

CONCLUSION

The results obtained demonstrate that phloroglucinol is toxic in the bacterium like in the yeast. The phloroglucinol toxicity on yeast cells is apparent starting from a phloroglucinol concentration of 15 g·l$^{-1}$.

Two libraries, containing respectively 28 and 38 transgenic yeast strains, were created and the results of the phloroglucinol toxicity study show that the overexpression of the PDR3 transcription factor, and also of the STE6, AQR1, DTR1, FLR1, QDR1, YHK8 and ATR1 transporters, makes it possible to increase the phloroglucinol resistance of the yeasts. Interestingly, the overexpression of the SNQ2 transporter confers resistance to phloroglucinol in an amount of 20 g·l$^{-1}$ in the medium, this being in the presence of 40 g·l$^{-1}$ of ethanol, the latter increasing the soluble fraction in the medium of the phloroglucinol and therefore its toxicity.

The invention claimed is:

1. An isolated living microorganism that is phloroglucinol resistant, wherein the isolated living microorganism withstands a phloroglucinol concentration, in a culture medium of the isolated living microorganism, of greater than or equal to 1 g·l$^{-1}$, and wherein the isolated living microorganism overexpresses at least one membrane transporter belonging to the PDR subfamily or to the MFS transporter family, or at least one transcription factor which controls the expression of said membrane transporter, said membrane transporter or said transcription factor being selected from SNQ2, STE6, PDR3, AQR1, DTR1,FLR1, QDR1, YHK8 and ATR1.

2. The isolated living microorganism according to claim 1, wherein the isolated living microorganism withstands a phloroglucinol concentration, in the culture medium, of greater than or equal to 20 g·l$^{-1}$.

3. The isolated living microorganism according to claim 1, wherein said membrane transporter is SNQ2.

4. The isolated living microorganism Living cell, preferably host cell, according to claim 1, wherein the isolated living microorganism overexpresses a polypeptide comprising SEQ ID No. 2.

5. The isolated living microorganism according to claim 1, wherein the isolated living microorganism overexpresses at least one enzyme involved in phloroglucinol biosynthesis.

6. The isolated living microorganism according to claim 1, wherein said microorganism is selected from bacteria, yeasts, fungi, algae, and cyanobacteria.

7. A method for obtaining a phloroglucinol-resistant recombinant microorganism, comprising at least the steps of:
  i. providing a nucleic acid molecule which comprises at least one nucleic acid sequence encoding a polypeptide selected from SNQ2, STE6, PDR3, AQR1, DTR1, FLR1, QDR1, YHK8 and ATR1,
  ii. cloning said nucleic acid molecule provided in step (i) in a vector capable of allowing the integration and/or the expression of said molecule in said microorganism,
  iii. bringing into contact said microorganism and said vector obtained in step (ii) in order for said microorganism to be transfected with said vector and for said host cell to express said nucleic acid molecule, said microorganism thus being phloroglucinol resistant.

8. The method according to claim 7, wherein said nucleic acid molecule encodes SNQ2.

9. The method according to claim 7, wherein said polypeptide comprises SEQ ID No. 2.

10. The method according to claim 7, wherein said microorganism also overexpresses at least one enzyme involved in phloroglucinol biosynthesis.

11. A method for producing phloroglucinol, comprising at least the steps of:
  i. obtaining a microorganism by carrying out the method according to claim 7,
  ii. bringing said microorganism into contact with an appropriate substrate,
  iii. incubating the mixture obtained in step (ii) under conditions suitable for producing phloroglucinol; and
  iv. optionally, recovering the reaction medium comprising the phloroglucinol obtained
after step (iii) and of purifying the phloroglucinol.

12. The method according to claim 7, wherein said microorganism is a yeast cell.

13. The isolated living microorganism according to claim 5, wherein the isolated living microorganism overexpresses at least one phloroglucinol synthase.

14. The isolated living microorganism according to claim 6, wherein said microorganism is a yeast.

15. The isolated living microorganism according to claim 14, wherein said yeast is selected from the genera *Saccharomyces, Candida, Ashbya, Dekkera, Pichia (Hansenula), Debaryomyces, Clavispora, Lodderomyces, Yarrowia, Zigosaccharomyces, Schizosaccharomyces, Torulaspora, Kluyveromyces, Brettanomycces, Cryptococcus* and *Malassezia*.

16. The isolated living microorganism according to claim 15, wherein said yeast is selected from the species *Saccharomyces cerevisiae, Saccharomyces boulardii, Saccharomyces douglasii, Saccharomyces bayanus, Zigosaccharomyces bailii, Schizosaccharomyces pombe, Dekkera brucelensis, Dekkera intermedia, Brettanomycces custersii, Brettanomycces intermedius, Kluyveromyces themotolerens, Torulaspora globosa* and *Torulaspora glabrata*.

17. The isolated living microorganism according to claim 16, whrein said yeast is of the *Saccharomyces cerevisiae* species.

* * * * *